United States Patent
Goldfarb et al.

(10) Patent No.: US 8,029,518 B2
(45) Date of Patent: Oct. 4, 2011

(54) METHODS AND DEVICES FOR CAPTURING AND FIXING LEAFLETS IN VALVE REPAIR

(75) Inventors: Eric A. Goldfarb, San Francisco, CA (US); Kent D. Dell, Redwood City, CA (US); Sylvia Wen-Chin Fan, San Francisco, CA (US); Brian B. Martin, Boulder Creek, CA (US); Ferolyn T. Powell, San Francisco, CA (US); Alfred H. Raschdorf, San Francisco, CA (US); Troy L. Thornton, San Francisco, CA (US)

(73) Assignee: Evalve, Inc., Menlo Park, CA (US)

( * ) Notice: Subject to any disclaimer, the term of this patent is extended or adjusted under 35 U.S.C. 154(b) by 1008 days.

(21) Appl. No.: 11/928,403

(22) Filed: Oct. 30, 2007

(65) Prior Publication Data

US 2008/0183194 A1  Jul. 31, 2008

Related U.S. Application Data

(63) Continuation of application No. 10/803,444, filed on Mar. 17, 2004, now Pat. No. 7,563,273, which is a continuation of application No. 09/894,463, filed on Jun. 27, 2001, now Pat. No. 6,752,813, which is a continuation-in-part of application No. 09/544,930, filed on Apr. 7, 2000, now Pat. No. 6,629,534.

(60) Provisional application No. 60/128,690, filed on Apr. 9, 1999.

(51) Int. Cl.
*A61B 17/10* (2006.01)
*A61B 17/04* (2006.01)

(52) U.S. Cl. .......................... 606/139; 606/232

(58) Field of Classification Search .................. 606/139, 606/151, 213, 215–217, 232; 623/2.11; 128/831, 128/898
See application file for complete search history.

(56) References Cited

U.S. PATENT DOCUMENTS

| 2,097,018 A | 10/1937 | Chamberlain |
| 2,108,206 A | 2/1938 | Meeker |

(Continued)

FOREIGN PATENT DOCUMENTS

DE  3504292  7/1986

(Continued)

OTHER PUBLICATIONS

Abe et al., "Updated: De Vega's annuloplasty for acquired tricuspid disease: Early and late results in 110 patients" Ann. Thorac. Surg. (1996) 62:1876-1877.

(Continued)

*Primary Examiner* — Julian Woo
(74) *Attorney, Agent, or Firm* — Sughrue Mion, PLLC; Jonathan Feuchtwang

(57) ABSTRACT

The present invention provides methods and devices for grasping, and optional repositioning and fixation of the valve leaflets to treat cardiac valve regurgitation, particularly mitral valve regurgitation. Such grasping will typically be atraumatic providing a number of benefits. For example, atraumatic grasping may allow repositioning of the devices relative to the leaflets and repositioning of the leaflets themselves without damage to the leaflets. However, in some cases it may be necessary or desired to include grasping which pierces or otherwise permanently affects the leaflets. In some of these cases, the grasping step includes fixation.

9 Claims, 48 Drawing Sheets

U.S. PATENT DOCUMENTS

| | | | |
|---|---|---|---|
| 3,296,668 A | 1/1967 | Aiken | |
| 3,378,010 A | 4/1968 | Codling et al. | |
| 3,671,979 A | 6/1972 | Moulopoulos | |
| 3,675,639 A * | 7/1972 | Cimber | 128/831 |
| 3,874,388 A | 4/1975 | King et al. | |
| 4,007,743 A | 2/1977 | Blake | |
| 4,056,854 A | 11/1977 | Boretos et al. | |
| 4,064,881 A | 12/1977 | Meredith | |
| 4,112,951 A | 9/1978 | Hulka et al. | |
| 4,235,238 A | 11/1980 | Ogiu et al. | |
| 4,297,749 A | 11/1981 | Davis et al. | |
| 4,425,908 A | 1/1984 | Simon | |
| 4,484,579 A | 11/1984 | Meno et al. | |
| 4,487,205 A | 12/1984 | Di Giovanni et al. | |
| 4,498,476 A | 2/1985 | Cerwin et al. | |
| 4,510,934 A | 4/1985 | Batra | |
| 4,578,061 A | 3/1986 | Lemelson | |
| 4,686,965 A | 8/1987 | Bonnet et al. | |
| 4,777,951 A | 10/1988 | Cribier et al. | |
| 4,809,695 A | 3/1989 | Gwathmey et al. | |
| 4,917,089 A | 4/1990 | Sideris | |
| 4,944,295 A | 7/1990 | Gwathmey et al. | |
| 4,969,890 A | 11/1990 | Sugita et al. | |
| 4,994,077 A | 2/1991 | Dobben | |
| 5,015,249 A | 5/1991 | Nakao et al. | |
| 5,019,096 A | 5/1991 | Fox, Jr. et al. | |
| 5,042,707 A | 8/1991 | Taheri | |
| 5,047,041 A | 9/1991 | Samuels | |
| 5,049,153 A | 9/1991 | Nakao et al. | |
| 5,061,277 A | 10/1991 | Carpentier et al. | |
| 5,069,679 A | 12/1991 | Taheri | |
| 5,108,368 A | 4/1992 | Hammerslag et al. | |
| 5,125,758 A | 6/1992 | DeWan | |
| 5,171,252 A | 12/1992 | Friedland | |
| 5,171,259 A | 12/1992 | Inoue | |
| 5,190,554 A | 3/1993 | Coddington, III et al. | |
| 5,195,968 A | 3/1993 | Lundquist et al. | |
| 5,209,756 A | 5/1993 | Seedhom et al. | |
| 5,226,429 A | 7/1993 | Kuzmak | |
| 5,226,911 A | 7/1993 | Chee et al. | |
| 5,234,437 A | 8/1993 | Sepetka | |
| 5,250,071 A | 10/1993 | Palermo | |
| 5,251,611 A | 10/1993 | Zehel et al. | |
| 5,254,130 A | 10/1993 | Poncet et al. | |
| 5,261,916 A | 11/1993 | Engelson | |
| 5,275,578 A | 1/1994 | Adams | |
| 5,282,845 A | 2/1994 | Bush et al. | |
| 5,304,131 A | 4/1994 | Paskar | |
| 5,306,283 A | 4/1994 | Conners | |
| 5,306,286 A | 4/1994 | Stack et al. | |
| 5,312,415 A | 5/1994 | Palermo | |
| 5,314,424 A | 5/1994 | Nicholas | |
| 5,318,525 A | 6/1994 | West et al. | |
| 5,320,632 A | 6/1994 | Heidmueller | |
| 5,325,845 A | 7/1994 | Adair | |
| 5,330,442 A | 7/1994 | Green et al. | |
| 5,332,402 A | 7/1994 | Teitelbaum | |
| 5,342,393 A * | 8/1994 | Stack | 606/213 |
| 5,350,397 A | 9/1994 | Palermo et al. | |
| 5,350,399 A | 9/1994 | Erlebacher et al. | |
| 5,359,994 A | 11/1994 | Krauter et al. | |
| 5,368,564 A | 11/1994 | Savage | |
| 5,368,601 A | 11/1994 | Sauer et al. | |
| 5,383,886 A | 1/1995 | Kensey et al. | |
| 5,391,182 A * | 2/1995 | Chin | 606/213 |
| 5,403,312 A | 4/1995 | Yates et al. | |
| 5,403,326 A | 4/1995 | Harrison et al. | |
| 5,411,552 A | 5/1995 | Anderson et al. | |
| 5,417,699 A | 5/1995 | Klein et al. | |
| 5,417,700 A | 5/1995 | Egan | |
| 5,423,857 A | 6/1995 | Rosenman et al. | |
| 5,423,858 A | 6/1995 | Bolanos et al. | |
| 5,423,882 A | 6/1995 | Jackman et al. | |
| 5,431,666 A | 7/1995 | Sauer et al. | |
| 5,437,551 A | 8/1995 | Chalifoux | |
| 5,437,681 A | 8/1995 | Meade et al. | |
| 5,447,966 A | 9/1995 | Hermes et al. | |
| 5,450,860 A | 9/1995 | O'Connor | |
| 5,456,400 A | 10/1995 | Shichman et al. | |
| 5,456,684 A | 10/1995 | Schmidt et al. | |
| 5,462,527 A | 10/1995 | Stevens-Wright et al. | |
| 5,472,044 A | 12/1995 | Hall et al. | |
| 5,476,470 A | 12/1995 | Fitzgibbons, Jr. | |
| 5,477,856 A | 12/1995 | Lundquist | |
| 5,478,309 A | 12/1995 | Sweezer et al. | |
| 5,478,353 A | 12/1995 | Yoon | |
| 5,487,746 A | 1/1996 | Yu et al. | |
| 5,496,332 A * | 3/1996 | Sierra et al. | 606/213 |
| 5,507,725 A | 4/1996 | Savage et al. | |
| 5,507,757 A | 4/1996 | Sauer et al. | |
| 5,520,701 A | 5/1996 | Lerch | |
| 5,522,873 A | 6/1996 | Jackman et al. | |
| 5,527,313 A | 6/1996 | Scott et al. | |
| 5,527,321 A | 6/1996 | Hinchliffe | |
| 5,527,322 A | 6/1996 | Klein et al. | |
| 5,536,251 A | 7/1996 | Evard et al. | |
| 5,540,705 A | 7/1996 | Meade et al. | |
| 5,542,949 A | 8/1996 | Yoon | |
| 5,554,185 A | 9/1996 | Block et al. | |
| 5,562,678 A | 10/1996 | Booker | |
| 5,569,274 A | 10/1996 | Rapacki et al. | |
| 5,571,085 A | 11/1996 | Accisano, III | |
| 5,571,137 A | 11/1996 | Marlow et al. | |
| 5,571,215 A | 11/1996 | Sterman et al. | |
| 5,575,802 A | 11/1996 | McQuilkin et al. | |
| 5,582,611 A | 12/1996 | Tsuruta et al. | |
| 5,593,424 A | 1/1997 | Northrup III | |
| 5,593,435 A | 1/1997 | Carpentier et al. | |
| 5,609,598 A | 3/1997 | Laufer et al. | |
| 5,618,306 A | 4/1997 | Roth et al. | |
| 5,620,452 A | 4/1997 | Yoon | |
| 5,620,461 A * | 4/1997 | Muijs Van De Moer et al. | 606/213 |
| 5,626,588 A | 5/1997 | Sauer et al. | |
| 5,634,932 A | 6/1997 | Schmidt | |
| 5,636,634 A | 6/1997 | Kordis et al. | |
| 5,639,277 A | 6/1997 | Mariant et al. | |
| 5,640,955 A | 6/1997 | Ockuly et al. | |
| 5,649,937 A | 7/1997 | Bito et al. | |
| 5,662,681 A | 9/1997 | Nash et al. | |
| 5,669,917 A | 9/1997 | Sauer et al. | |
| 5,690,671 A | 11/1997 | McGurk et al. | |
| 5,695,504 A | 12/1997 | Gifford, III et al. | |
| 5,695,505 A | 12/1997 | Yoon | |
| 5,702,825 A | 12/1997 | Keital et al. | |
| 5,706,824 A | 1/1998 | Whittier | |
| 5,709,707 A | 1/1998 | Lock et al. | |
| 5,713,910 A | 2/1998 | Gordon et al. | |
| 5,713,911 A | 2/1998 | Racene et al. | |
| 5,715,817 A | 2/1998 | Stevens-Wright et al. | |
| 5,716,367 A | 2/1998 | Koike et al. | |
| 5,718,725 A | 2/1998 | Sterman et al. | |
| 5,719,725 A | 2/1998 | Nakao | |
| 5,722,421 A | 3/1998 | Francese et al. | |
| 5,725,542 A | 3/1998 | Yoon | |
| 5,725,556 A | 3/1998 | Moser et al. | |
| 5,738,649 A | 4/1998 | Macoviak | |
| 5,741,280 A | 4/1998 | Fleenor | |
| 5,749,828 A | 5/1998 | Solomon et al. | |
| 5,769,812 A | 6/1998 | Stevens et al. | |
| 5,769,863 A | 6/1998 | Garrison | |
| 5,772,578 A | 6/1998 | Heimberger et al. | |
| 5,782,845 A | 7/1998 | Shewchuk | |
| 5,797,927 A | 8/1998 | Yoon | |
| 5,797,960 A | 8/1998 | Stevens et al. | |
| 5,810,847 A | 9/1998 | Laufer et al. | |
| 5,810,849 A | 9/1998 | Kontos | |
| 5,810,853 A | 9/1998 | Yoon | |
| 5,810,876 A | 9/1998 | Kelleher | |
| 5,814,029 A | 9/1998 | Hassett | |
| 5,820,592 A | 10/1998 | Hammerslag | |
| 5,820,631 A | 10/1998 | Nobles | |
| 5,823,955 A | 10/1998 | Kuck et al. | |
| 5,823,956 A | 10/1998 | Roth et al. | |
| 5,824,065 A | 10/1998 | Gross | |
| 5,827,237 A | 10/1998 | Macoviak et al. | |
| 5,829,447 A | 11/1998 | Stevens et al. | |

| | | | |
|---|---|---|---|
| 5,833,671 A | 11/1998 | Macoviak et al. | |
| 5,836,955 A | 11/1998 | Buelna et al. | |
| 5,840,081 A | 11/1998 | Anderson et al. | |
| 5,843,031 A | 12/1998 | Hermann et al. | |
| 5,849,019 A | 12/1998 | Yoon | |
| 5,853,422 A | 12/1998 | Huebsch et al. | |
| 5,855,271 A | 1/1999 | Eubanks et al. | |
| 5,855,614 A | 1/1999 | Stevens et al. | |
| 5,860,990 A | 1/1999 | Nobles et al. | |
| 5,861,003 A * | 1/1999 | Latson et al. | 606/213 |
| 5,868,733 A | 2/1999 | Ockuly et al. | |
| 5,876,399 A | 3/1999 | Chia et al. | |
| 5,879,307 A | 3/1999 | Chio et al. | |
| 5,885,271 A | 3/1999 | Hamilton et al. | |
| 5,891,160 A | 4/1999 | Williamson, IV et al. | |
| 5,916,147 A | 6/1999 | Boury | |
| 5,928,224 A | 7/1999 | Laufer | |
| 5,944,733 A | 8/1999 | Engelson | |
| 5,947,363 A | 9/1999 | Bolduc et al. | |
| 5,954,732 A | 9/1999 | Hart et al. | |
| 5,957,949 A | 9/1999 | Leonhard et al. | |
| 5,972,020 A | 10/1999 | Carpentier et al. | |
| 5,972,030 A | 10/1999 | Garrison et al. | |
| 5,980,455 A | 11/1999 | Daniel et al. | |
| 5,989,284 A | 11/1999 | Laufer | |
| 6,015,417 A | 1/2000 | Reynolds, Jr. | |
| 6,019,722 A | 2/2000 | Spence et al. | |
| 6,022,360 A | 2/2000 | Reimels et al. | |
| 6,033,378 A | 3/2000 | Lundquist et al. | |
| 6,036,699 A | 3/2000 | Andreas et al. | |
| 6,048,351 A | 4/2000 | Gordon et al. | |
| 6,059,757 A | 5/2000 | Macoviak et al. | |
| 6,060,628 A | 5/2000 | Aoyama et al. | |
| 6,060,629 A | 5/2000 | Pham et al. | |
| 6,063,106 A | 5/2000 | Gibson | |
| 6,066,146 A | 5/2000 | Carroll et al. | |
| 6,068,628 A | 5/2000 | Fanton et al. | |
| 6,068,629 A | 5/2000 | Haissaguerre et al. | |
| 6,077,214 A | 6/2000 | Mortier et al. | |
| 6,086,600 A | 7/2000 | Kortenbach | |
| 6,088,889 A | 7/2000 | Luther et al. | |
| 6,099,553 A | 8/2000 | Hart et al. | |
| 6,110,145 A | 8/2000 | Macoviak | |
| 6,117,144 A | 9/2000 | Nobles et al. | |
| 6,117,159 A | 9/2000 | Huebsch et al. | |
| 6,123,699 A | 9/2000 | Webster, Jr. | |
| 6,126,658 A | 10/2000 | Baker | |
| 6,132,447 A | 10/2000 | Dorsey | |
| 6,136,010 A | 10/2000 | Modesitt et al. | |
| 6,143,024 A | 11/2000 | Campbell et al. | |
| 6,159,240 A | 12/2000 | Sparer et al. | |
| 6,162,233 A | 12/2000 | Williamson, IV et al. | |
| 6,165,164 A | 12/2000 | Hill et al. | |
| 6,165,183 A | 12/2000 | Kuehn et al. | |
| 6,165,204 A | 12/2000 | Levinson et al. | |
| 6,168,614 B1 | 1/2001 | Andersen et al. | |
| 6,171,320 B1 | 1/2001 | Monassevitch | |
| 6,182,664 B1 | 2/2001 | Cosgrove | |
| 6,187,003 B1 | 2/2001 | Buysse et al. | |
| 6,190,408 B1 | 2/2001 | Melvin | |
| 6,203,531 B1 | 3/2001 | Ockuly et al. | |
| 6,203,553 B1 | 3/2001 | Robertson et al. | |
| 6,206,893 B1 | 3/2001 | Klein et al. | |
| 6,206,907 B1 | 3/2001 | Marino et al. | |
| 6,210,419 B1 | 4/2001 | Mayenberger et al. | |
| 6,210,432 B1 | 4/2001 | Solem et al. | |
| 6,245,079 B1 | 6/2001 | Nobles et al. | |
| 6,267,746 B1 | 7/2001 | Bumbalough | |
| 6,267,781 B1 | 7/2001 | Tu | |
| 6,269,819 B1 | 8/2001 | Oz et al. | |
| 6,277,555 B1 | 8/2001 | Duran et al. | |
| 6,283,127 B1 | 9/2001 | Sterman et al. | |
| 6,283,962 B1 | 9/2001 | Tu et al. | |
| 6,299,637 B1 | 10/2001 | Shaolian et al. | |
| 6,306,133 B1 | 10/2001 | Tu et al. | |
| 6,312,447 B1 | 11/2001 | Grimes | |
| 6,319,250 B1 | 11/2001 | Falwell et al. | |
| 6,322,559 B1 | 11/2001 | Daulton et al. | |
| 6,332,893 B1 | 12/2001 | Mortier et al. | |
| 6,352,708 B1 | 3/2002 | Duran et al. | |
| 6,355,030 B1 | 3/2002 | Aldrich et al. | |
| 6,358,277 B1 | 3/2002 | Duran | |
| 6,368,326 B1 | 4/2002 | Dakin et al. | |
| 6,387,104 B1 * | 5/2002 | Pugsley et al. | 606/139 |
| 6,402,780 B2 | 6/2002 | Williamson et al. | |
| 6,402,781 B1 | 6/2002 | Langberg et al. | |
| 6,406,420 B1 | 6/2002 | McCarthy et al. | |
| 6,419,669 B1 | 7/2002 | Frazier et al. | |
| 6,461,366 B1 | 10/2002 | Seguin | |
| 6,464,707 B1 | 10/2002 | Bjerken | |
| 6,482,224 B1 | 11/2002 | Michler et al. | |
| 6,485,489 B2 | 11/2002 | Teirstein et al. | |
| 6,508,828 B1 | 1/2003 | Akerfeldt et al. | |
| 6,533,796 B1 | 3/2003 | Sauer et al. | |
| 6,537,314 B2 | 3/2003 | Langberg et al. | |
| 6,540,755 B2 | 4/2003 | Ockuly et al. | |
| 6,551,331 B2 | 4/2003 | Nobles et al. | |
| 6,562,037 B2 | 5/2003 | Paton et al. | |
| 6,562,052 B2 | 5/2003 | Nobles et al. | |
| 6,575,971 B2 | 6/2003 | Hauck et al. | |
| 6,585,761 B2 | 7/2003 | Taheri | |
| 6,599,311 B1 | 7/2003 | Biggs et al. | |
| 6,616,684 B1 | 9/2003 | Vidlund et al. | |
| 6,619,291 B2 | 9/2003 | Hlavka et al. | |
| 6,626,899 B2 | 9/2003 | Houser et al. | |
| 6,626,930 B1 | 9/2003 | Allen et al. | |
| 6,629,534 B1 | 10/2003 | St. Goar et al. | |
| 6,641,592 B1 | 11/2003 | Sauer et al. | |
| 6,656,221 B2 | 12/2003 | Taylor et al. | |
| 6,669,687 B1 | 12/2003 | Saadat | |
| 6,685,648 B2 | 2/2004 | Flaherty et al. | |
| 6,689,164 B1 | 2/2004 | Seguin | |
| 6,695,866 B1 | 2/2004 | Kuehn et al. | |
| 6,701,929 B2 | 3/2004 | Hussein | |
| 6,702,825 B2 | 3/2004 | Frazier et al. | |
| 6,702,826 B2 | 3/2004 | Liddicoat et al. | |
| 6,709,382 B1 | 3/2004 | Horner | |
| 6,709,456 B2 | 3/2004 | Langberg et al. | |
| 6,718,985 B2 | 4/2004 | Hlavka et al. | |
| 6,719,767 B1 | 4/2004 | Kimblad | |
| 6,723,038 B1 | 4/2004 | Schroeder et al. | |
| 6,726,716 B2 | 4/2004 | Marquez | |
| 6,740,107 B2 | 5/2004 | Loeb et al. | |
| 6,746,471 B2 | 6/2004 | Mortier et al. | |
| 6,752,813 B2 | 6/2004 | Goldfarb et al. | |
| 6,755,777 B2 | 6/2004 | Schweich et al. | |
| 6,764,510 B2 | 7/2004 | Vidlund et al. | |
| 6,767,349 B2 | 7/2004 | Ouchi | |
| 6,770,083 B2 | 8/2004 | Seguin | |
| 6,797,001 B2 | 9/2004 | Mathis et al. | |
| 6,797,002 B2 | 9/2004 | Spence et al. | |
| 6,860,179 B2 | 3/2005 | Hopper et al. | |
| 6,875,224 B2 | 4/2005 | Grimes | |
| 6,926,715 B1 | 8/2005 | Hauck et al. | |
| 6,945,978 B1 | 9/2005 | Hyde | |
| 6,949,122 B2 | 9/2005 | Adams et al. | |
| 6,966,914 B2 | 11/2005 | Abe | |
| 6,986,775 B2 | 1/2006 | Morales et al. | |
| 7,004,970 B2 | 2/2006 | Cauthen, III et al. | |
| 7,011,669 B2 | 3/2006 | Kimblad | |
| 7,048,754 B2 | 5/2006 | Martin et al. | |
| 7,112,207 B2 | 9/2006 | Allen et al. | |
| 7,226,467 B2 | 6/2007 | Lucatero et al. | |
| 7,288,097 B2 | 10/2007 | Séguin | |
| 7,381,210 B2 | 6/2008 | Zarbatany et al. | |
| 7,464,712 B2 | 12/2008 | Oz et al. | |
| 7,497,822 B1 | 3/2009 | Kugler et al. | |
| 7,533,790 B1 | 5/2009 | Knodel et al. | |
| 7,563,267 B2 | 7/2009 | Goldfarb et al. | |
| 7,563,273 B2 | 7/2009 | Goldfarb et al. | |
| 7,604,646 B2 | 10/2009 | Goldfarb et al. | |
| 7,635,329 B2 | 12/2009 | Goldfarb et al. | |
| 2001/0004715 A1 | 6/2001 | Duran et al. | |
| 2001/0005787 A1 | 6/2001 | Oz et al. | |
| 2001/0018611 A1 | 8/2001 | Solem et al. | |
| 2001/0022872 A1 | 9/2001 | Marui | |
| 2001/0037084 A1 | 11/2001 | Nardeo | |
| 2001/0039411 A1 | 11/2001 | Johansson et al. | |

| | | |
|---|---|---|
| 2001/0044568 A1 | 11/2001 | Langberg et al. |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055774 A1 | 5/2002 | Liddicoat |
| 2002/0055775 A1 | 5/2002 | Carpentier et al. |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0147456 A1 | 10/2002 | Diduch et al. |
| 2002/0156526 A1 | 10/2002 | Hlavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0183766 A1 | 12/2002 | Seguin |
| 2002/0183835 A1 | 12/2002 | Taylor et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0208231 A1 | 11/2003 | Williamson, IV et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St. Goar et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0088047 A1 | 5/2004 | Spence et al. |
| 2004/0092962 A1 | 5/2004 | Thorton et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Laiska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225300 A1 | 11/2004 | Goldfarb et al. |
| 2004/0236354 A1 | 11/2004 | Seguin |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St. Goar et al. |
| 2005/0021057 A1 | 1/2005 | St. Goar et al. |
| 2005/0021058 A1 | 1/2005 | Negro |
| 2005/0033446 A1 | 2/2005 | Deem et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0149014 A1 | 7/2005 | Hauck et al. |
| 2005/0159810 A1 | 7/2005 | Filsoufi |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0273160 A1 | 12/2005 | Lashinski et al. |
| 2005/0287493 A1 | 12/2005 | Novak et al. |
| 2006/0004247 A1 | 1/2006 | Kute et al. |
| 2006/0015003 A1 | 1/2006 | Moaddes et al. |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0089671 A1 | 4/2006 | Goldfarb et al. |
| 2006/0089711 A1 | 4/2006 | Dolan |
| 2006/0135993 A1 | 6/2006 | Seguin |
| 2006/0184203 A1 | 8/2006 | Martin et al. |
| 2006/0195012 A1 | 8/2006 | Mortier et al. |
| 2006/0229708 A1 | 10/2006 | Powell et al. |
| 2006/0252984 A1 | 11/2006 | Rahdert et al. |
| 2007/0038293 A1 | 2/2007 | St.Goar et al. |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0198082 A1 | 8/2007 | Kapadia et al. |
| 2008/0039935 A1 | 2/2008 | Buch et al. |
| 2008/0051703 A1 | 2/2008 | Thorton et al. |
| 2008/0051807 A1 | 2/2008 | St. Goar et al. |
| 2008/0097489 A1 | 4/2008 | Goldfarb et al. |
| 2008/0167714 A1 | 7/2008 | St. Goar et al. |
| 2009/0156995 A1 | 6/2009 | Martin et al. |
| 2009/0163934 A1 | 6/2009 | Raschdorf, Jr. et al. |
| 2009/0177266 A1 | 7/2009 | Powell et al. |
| 2009/0198322 A1 | 8/2009 | Deem et al. |
| 2009/0270858 A1 | 10/2009 | Hauck et al. |
| 2009/0326567 A1 | 12/2009 | Goldfarb et al. |
| 2010/0016958 A1 | 1/2010 | St. Goar et al. |
| 2010/0022823 A1 | 1/2010 | Goldfarb et al. |

FOREIGN PATENT DOCUMENTS

| | | |
|---|---|---|
| EP | 0 179 562 B1 | 7/1989 |
| EP | 179562 | 7/1989 |
| EP | 558031 | 9/1993 |
| EP | 684012 A2 | 2/1995 |
| EP | 0 727 239 | 8/1996 |

| | | |
|---|---|---|
| EP | 1674040 | 6/2006 |
| FR | 2768324 | 3/1999 |
| GB | 1598111 | 9/1981 |
| GB | 2151142 | 7/1985 |
| JP | 11-89937 | 6/1999 |
| WO | WO 81/00668 | 3/1981 |
| WO | WO 91/01689 | 2/1991 |
| WO | WO 91/18881 | 12/1991 |
| WO | WO 92/12690 | 8/1992 |
| WO | WO 94/18881 | 9/1994 |
| WO | WO 94/18893 | 9/1994 |
| WO | WO 95/15715 A1 | 6/1995 |
| WO | WO 96/14032 A1 | 5/1996 |
| WO | WO 96/22735 | 8/1996 |
| WO | WO 96/30072 A1 | 10/1996 |
| WO | WO 97/25927 A1 | 7/1997 |
| WO | WO 97/26034 A1 | 7/1997 |
| WO | WO 97/38748 A2 | 10/1997 |
| WO | WO 97/39688 | 10/1997 |
| WO | WO 97/48436 A2 | 12/1997 |
| WO | WO 98/07375 | 2/1998 |
| WO | WO 98/24372 | 6/1998 |
| WO | WO 98/30153 | 7/1998 |
| WO | WO 98/32382 | 7/1998 |
| WO | WO 98/35638 | 8/1998 |
| WO | WO 99/00059 | 1/1999 |
| WO | WO 99/01377 | 1/1999 |
| WO | WO 99/07354 | 2/1999 |
| WO | WO 99/13777 A1 | 3/1999 |
| WO | WO 99/66967 A1 | 12/1999 |
| WO | WO 00/02489 | 1/2000 |
| WO | WO 00/03651 A1 | 1/2000 |
| WO | WO 00/03759 | 1/2000 |
| WO | WO 00/12168 A1 | 3/2000 |
| WO | WO 00/44313 A1 | 8/2000 |
| WO | WO 00/59382 A1 | 10/2000 |
| WO | WO 00/60995 | 10/2000 |
| WO | WO 01/00111 | 1/2001 |
| WO | WO 01/00114 A1 | 1/2001 |
| WO | WO 01/03651 A2 | 1/2001 |
| WO | WO 01/26557 | 4/2001 |
| WO | WO 01/26586 | 4/2001 |
| WO | WO 01/26587 A1 | 4/2001 |
| WO | WO 01/26588 A2 | 4/2001 |
| WO | WO 01/26703 A1 | 4/2001 |
| WO | WO 01/28432 | 4/2001 |
| WO | WO 01/28455 | 4/2001 |
| WO | WO 01/47438 A1 | 7/2001 |
| WO | WO 01/49213 A2 | 7/2001 |
| WO | WO 01/49213 A3 | 7/2001 |
| WO | WO 01/50985 A1 | 7/2001 |
| WO | WO 01/54618 | 8/2001 |
| WO | WO 01/56512 A1 | 8/2001 |
| WO | WO 01/66001 | 9/2001 |
| WO | WO 01/70320 A1 | 9/2001 |
| WO | WO 01/89440 A2 | 11/2001 |
| WO | WO 01/95831 A2 | 12/2001 |
| WO | WO 01/95832 A2 | 12/2001 |
| WO | WO 01/97741 A2 | 12/2001 |
| WO | WO 02/00099 A2 | 1/2002 |
| WO | WO 02/01999 A2 | 1/2002 |
| WO | WO 02/03892 | 1/2002 |
| WO | WO 02/34167 A2 | 5/2002 |
| WO | WO 02/34167 A3 | 5/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 03/001893 | 1/2003 |
| WO | WO 03/003930 A1 | 1/2003 |
| WO | WO 03/020179 | 3/2003 |
| WO | WO 03/028558 | 4/2003 |
| WO | WO 03/037171 | 5/2003 |
| WO | WO 03/047467 | 6/2003 |
| WO | WO 03/049619 | 6/2003 |
| WO | WO 03/073910 | 9/2003 |
| WO | WO 03/073913 | 9/2003 |
| WO | WO 03/105667 A3 | 12/2003 |
| WO | WO 2004/004607 | 1/2004 |
| WO | WO 2004/012583 | 2/2004 |
| WO | WO 2004/012789 A2 | 2/2004 |
| WO | WO 2004/014282 A2 | 2/2004 |
| WO | WO 2004/019811 | 3/2004 |
| WO | WO 2004/030570 | 4/2004 |
| WO | WO 2004/082538 A2 | 4/2004 |
| WO | WO 2004/037317 | 5/2004 |
| WO | WO 2004/045370 | 6/2004 |
| WO | WO 2004/045378 A2 | 6/2004 |
| WO | WO 2004/045463 | 6/2004 |
| WO | WO 2004/047679 | 6/2004 |
| WO | WO 2004/062725 | 7/2004 |
| WO | WO 2004/082523 A2 | 9/2004 |
| WO | WO 2004/082538 | 9/2004 |
| WO | WO 2004/093730 | 11/2004 |
| WO | WO 2004/112585 | 12/2004 |
| WO | WO 2004/112651 | 12/2004 |
| WO | WO 2005/002424 | 1/2005 |
| WO | WO 2005/018507 | 3/2005 |
| WO | WO 2005/027797 A1 | 3/2005 |
| WO | WO 2005/032421 A2 | 4/2005 |
| WO | WO 2005/062931 A2 | 7/2005 |
| WO | WO 2005/112792 | 12/2005 |
| WO | WO 2006/105008 | 10/2006 |
| WO | WO 2006/105009 | 10/2006 |
| WO | WO 2006/115875 | 11/2006 |
| WO | WO 2006/115876 | 11/2006 |

OTHER PUBLICATIONS

Alfieri, et al., "An effective technique to correct anterior mitral leaflet prolapse," J Card Surg, 1999; 14(6):468-470.

Alfieri et al., "The edge to edge technique," The European Association for Cardio-Thoracic Surgry 14th Annual Meeting, Oct. 7-11, 2000, Book of Proceedings.

Alvarez et al., "Repairing the degenerative mitral valve: Ten- to fifteen-year follow-up" J. Thorac. Cardiovasc. Surg. (1996) 112:238-247.

Bach et al., "Early improvement in congestive heart failure after correction of secondary mitral regurgitation in end-stage cardiomyopathy" Am. Heart J. (1995) 129:1165-1170.

Bach et al., "Improvement following correction of secondary mitral regurgitation in end-stage cardiomyopathy with mitral annuloplasty" Am. J. Cardiol. (1996) 78:966-969.

Bailey, "Surgery of the Heart" Chapter 20 (1995) pp. 686-737.

Bernal et al., "The 'Valve Racket': a new and different concept of atrioventricular valve repair," Eur. J. Cardio-thoracic Surgery 29:1026-29 (2006).

Bolling et al., "Surgery for acquired heart disease" (1995) 109:676-683.

Borghetti V. et al., "Preliminary observations on haemodynamics during physiological stress conditions following 'double-orifice' mitral valve repair," European Journal of Cardio-thoracic Surgery, Apr. 18, 2001, 20:262-269.

Dec et al., "Idiopathic dilated cardiomyopathy" N. Engl. J. Med. (1994) 331:1564-1575.

Derwent citing German language patent EP 684012 published Nov. 12, 1995 for: "Thread for constructing surgical seam has flexible section with two ends, with lower fastening part on thread first end having hollow cylinder with continuous hole through which surgical needle threads" 2 pgs.

Derwent citing Japanese language patent JP 11089937 published Jun. 4, 1999 for: "Catheter for mitral regurgitation test—includes jet nozzles provided on rear side of large diametered spindle shaped portion attached to end of narrow diametered tube" 1 pg.

Dottori et al., "Echocardiographic imaging of the Alfieri type mitral valve repair," Ital Heart J, Jan. 24, 2001, 2(4):319-320.

Falk et al., "Computer-enhanced mitral valve surgery: toward a total endoscopic procedure," Seminars in thoracic and cardiovascular surgery, Jul. 1999; 11(3):224-249.

Filsoufi et al., "Restoring Optimal Surface of Coaptation With a Mini Leaflet Prosthesis: A New Surgical Concept for the Correction of Mitral Valve Prolapse," Int'l. Soc. for Minimally Invasive Cardiothoracic Surgery 1(4):186-87 (2006).

Fucci et al., "Improved results with mitral valve repair using new surgical techniques," Eur J Cardio-thorac Surg, 1995; 9:621-627.

Fundaro et al., "Chordal plication and free edge remodeling for mitral anterior leaflet prolapse repair: 8-year follow-up," Annals of Thoracic Surgery, 2001; 72:1515-1519.

Garcia-Rinaldi et al., "Left ventricular volume reduction and reconstruction is ischemic cardiomyopathy," Journal of Cardiac Surgery, 1999; 14:199-210.

Gillinov et al., "Is minimally invasive heart valve surgery a paradigm for the future?," Current Cardiology Reports, 1999; 1:318-322.

Gundry, "Facile mitral valve repair utilizing leaflet edge approximation: midterm results of the Alfieri figure of eight repair," Presented at the Meeting of The Western Thoracic Surgical Association, 1999.

Ikeda et al., "Batista's operation with coronary artery bypass grafting and mitral valve plasty for ischemic dilated cardiomyopathy," The Japanese Journal of Thoracic and Cardiovascular Surgery, Nov. 2000; 48:746-749.

Izzat et al., "Early experience with partial left ventriculectomy in the Asia-Pacific Region," Annuals of Thoracic Surgery, 1999; 67:1703-1707.

Källner et al., "Transaortic approach for the Alfieri Stitch," Ann Thorac Surg, 2001; 71:378-380.

Kameda et al., "Annuloplasty for severe mitral regurgitation due to dilated cardiomyopathy" Am. Thorac. Surg. (1996) 61:1829-1832.

Kavarna t al., "Transaortic repair of mitral regurgitation," Presented at the third annual New Era Cardiac Care conference, San Diego, CA Jan. 13-16, 2000, http://www.hsforum.com/vol3/issue1/2000-2389print.html.

Khan et al., "Blade atrial septostomy: Experience with the first 50 procedures" Cathet. Cardiovasc. Diagn. (1991) 23:257-262.

Konertz et al., "Results after partial left ventriculectomy in a European heart failure population," Journal of Cardiac Surgery, 1999; 14(2):129-135.

Krüger et al, "Edge to edge technique in complex mitral valve repair," Thorac Cardiovasc Surg, 2000, Thema: Poster, http://www.thieme.de/thoracic/abstracts/abstracts/p_73.html.

Langer et al., "Posterior mitral leaflet extensions: An adjunctive repair option for ischemic mitral regurgitation?," J. Thorac. Cardiovasc. Surf. 131:868-77 (2006).

Lorusso et al., "The double-orifice technique for mitral valve construction: predictors of postoperative outcome," Eur J. Cardiothorac Surg, May 23, 2001; 20(3):583-589.

Lorusso e al., "Double-Orifice technique to repair extensive mitral valve excision following acute endocarditis," J Card Surg, 1998; 13:24-26.

Maisano et al., "The edge-to-edge technique: A simplified method to correct mitral insufficiency" Eur. J. Cardiothorac. Surg. (1998) 13:240-246.

Maisano t al., "The double orifice technique as a standardized approach to treat mitral regurgitation due to severe myxomatous disease: surgical technique," European Journal of Cardiothoracic Surgery, Jan. 18, 2000; 17:201-215.

Maisano et al., "The double orifice repair for Barlow Disease: a simple solution for a complex repair," Supplement I Circulation, 1999; 100(18):I-94.

Maisano, F. et al., "The hemodynamic effects of double-orifice valve repair for mitral regurgitation: a 3D computational model," European Journal of Cardio-thoracic Surgery, 1999; 15:419-425.

Maisano t al., "Valve repair for traumatic tricuspid regurgitation," Eur J. Cardio-thorac Surg, 1996; 10:867-873.

Mantovani et al., "Edge-to-edge repair of congenital familiar tricuspid regurgitation: case report," J. Heart Valve Dis, Sep. 2000; 9(5):641-643.

McCarthy et al. "Tricuspid valve repair with the Cosgrove-Edwards annuloplasty system" Am. Thorac. Surg. (1997) 64:267-268.

McCarthy et al., "Partial left ventriculectomy and mitral valve repair for end-stage congestive heart failure," European Journal of Cardio-thoracic Surgery, 1998; 13:337-343.

Morales et al., "Development of an off bypass mitral valve repair," The Heart Surgery Forum #1999-4963, 1999; 2(2):115-120.

Nakanishi et al., "Early outcome with the Alfieri mitral valve repair," J Cardiol, May 2001; 37(5):263-266, (Abstract in English; Article in Japanese.).

Nielsen et al., "The edge-to-edge mitral repair: tension on the approximating suture and leaflet deformation during acute ischemic mitral regurgitation in the ovine heart," Circulation, 2001;104 [ suppl I]:I-29-I-35.

Osawa et al., "Partial left ventriculectomy in a 3 year old boy with dilated cardiomyopathy," Japanese Journal of Thoracic and Cardiovascular Surgery, Sep. 2000, 48(9):590-593.

Park et al., "Clinical use of a blade atrial septostomy" Circulation (1978) 58:600-608.

Reul et al., Mitral Valve Reconstruction for Mitral Insufficiency, Progress in Cardiovascular Diseases, No. 6, May/Jun. 1997, pp. 567-599, vol. XXXIX.

Ricchi et al. "Linear segmental annuloplasty for mitral valve repair" Ann. Thorac. Surg. (1997) 63:1805-1806.

Tager et al., "Long-term follow-up of Rheumatic patients undergoing left-sided valve replacement with tricuspid annuloplasty—Validity of preoperative echocardiographic criteria in the decision to perform tricuspid annulopasty" Am. J. Cardiol. (1998) 81:1013-1016.

Timek et al., "Edge-to-edge mitral repair: gradients and three-dimensional annular dynamics in vivo during inotropic stimulation," European Journal of Cardiothoracic Surgery, Jan. 9, 2001; 19:431-437.

Totaro et al., "Mitral valve repair for isolated prolapse of the anterior leaflet: an 11 year follow-up," European Journal of Cardio-Thoracic Surgery, 1999; 15:119-126.

Uchida et al., "Percutaneous cardiomyotomy and valvultomy with angioscopic guidance" Am. Heart J. (1991) 121:1221-1224.

Umana et al., "'Bow-tie' mitral valve repair successfully addresses subvalvular dysfunction in ischemic mitral regurgitation" (1997) Surgical Forum pp. 279-280.

Umana et al., "'Bow-tie' mitral valve repair: An adjuvant technique for ischemic mitral regurgitation" Ann. Thorac. Surg. (1998) 66:1640-1646.

Abe et al., "De Vega's annuloplasty for acquired tricuspid disease: Early and late results in 110 patients" Ann. Thorac. Surg. (1989) 48:670-676.

Agricola et al., "Mitral valve reserve in double orifice technique: an exercise echocardiographic study," Journal of Heart Valve Disease, (2002)11(5):637 643.

Alfieri et al., "Novel suture device for beating heart mitral leaflet approximation," Annals of Thoracic Surgery, (2002)74:1488 1493.

Alfieri et al., "The double orifice technique in mitral valve repair: a simple solution for complex problems," Journal of Thoracic Cardiovascular Surgery, (2001)122:674 681.

Alfieri , "The edge-to-edge repair of the mitral valve," [Abstract] 6th Annual NewEra Cardiac Care: Innovation & Technology, Heart Surgery Forum, (2003) pp. 103.

Arisi et al., "Mitral valve repair with Alfieri technique in mitral regurgitation of diverse etiology: early echocardiographic results," Circulation Supplement II, (2001) 104(17):3240.

Bhudia et al., "Edge-to-edge (Alfieri) mitral repair: results in diverse clinical settings," Ann Thorac Surg, 77: 1598-1606, (2004).

Castedo, "Edge-to-edge tricuspid repair for redeveloped valve incompetence after DeVega's annuloplasty," AnnThora Surg, (2003) 75;605-6.

Downing et al., "Beating heart mitral valve surgery: Preliminary model and methodology," Journal of Thoracic and Cardiovascular Surgery, (2002) 123(6):1141-1146.

Frazier et al., #62 Early Clinical Experience With an Implantable, Intracardiac Circulatory Support Device: Operative Considerations and Physiologic Implications, 2003 STS Presentation, 1 page total. [Abstract Only].

Gateliene , "Early and postoperative results of metal and tricuspid valve insufficiency surgical treatment using edge-to-edge central coaptation procedure," (2002) 38 Suppl 2:172-5.

Gatti et al., "The edge to edge technique as a trick to rescue an imperfect mitral valve repair," Eur J Cardiothorac Surg, (2002) 22(5):817 20.

Gupta et al., #61 Influence of Older Donor Grafts on Heart Transplant Survival: Lack of Recipient Effects, 2003 STS Presentation, [Abstract Only].

Kaza et al., "Ventricular reconstruction results in improved left ventricular function and amelioration of mitral insufficiency," Annals of Surgery, (2002) 235(6):828 832.

Kron et al., "Surgical relocation of the posterior papillary muscle in chronic ischemic mitral regurgitation," Annals. of Thoracic Surgery, (2002)74:600 601.

Moainie et al., Correction of traumatic tricuspid regurgitation using the double orifice technique, Annals of Thoracic Surgery, (2002) 73:963 965.

Noera et al.., "Tricuspid Valve Incompetence Caused by Nonpenetrating Thoracic Trauma", Annals of Thoracic Surgery, 1991, 51 (2), 320-322.

Patel et al., #57 Epicardial Atrial Defibrillation: Novel Treatment of Postoperative Atrial Fibrillation, 2003 STS Presentation, [Abstract Only].

Privitera et al., "Mitral Valve Repair: Clinical Outcome and Pathology; Circulation," (2002) 106:173.

Redaelli et al., A computational study of the hemodynamics after 'edge-to-edge' mitral valve repair, Journal of Biomechanical Engineering, (2001) 123:565-570.

Robicsek et al., #60 The Bicuspid Aortic Valve: How Does It Function? Why Does It Fail?, 2003 STS Presentation, [Abstract Only].

Tamura et al., Edge to edge repair for mitral regurgitation in a patient with chronic hemodialysis: report of a case, Kyobu Geka, (2001) 54(9):788-790.

Tibayan et al., #59 Annular Geometric Remodeling in Chronic Ischemic Mitral Regurgitation, 2003 STS Presentation, [Abstract Only].

Timek, "Edge-to-edge mitral valve repair without annuloplasty ring in acute ischemic mitral regurgitation," [Abstract] Clinical Science, Abstracts from Scientific Sessions, (2002) II-461.

Votta et al., "3 D computational analysis of the stress distribution on the leaflets after edge to edge repair of mitral regurgitation," Journal of Heart Valve Disease, (2002)11:810 822.

Supplemental European Search Report of EP Application No. 02746781, mailed May 13, 2008, 3 pages total.

* cited by examiner

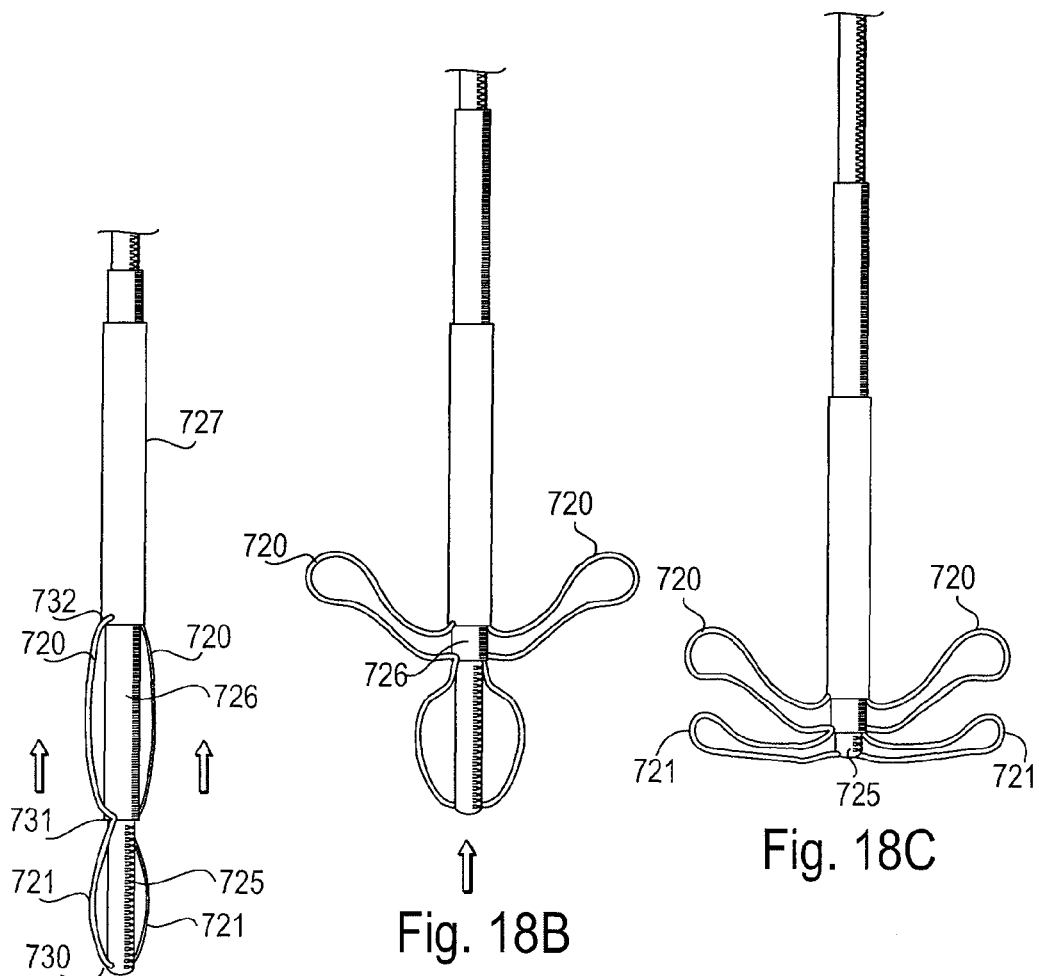
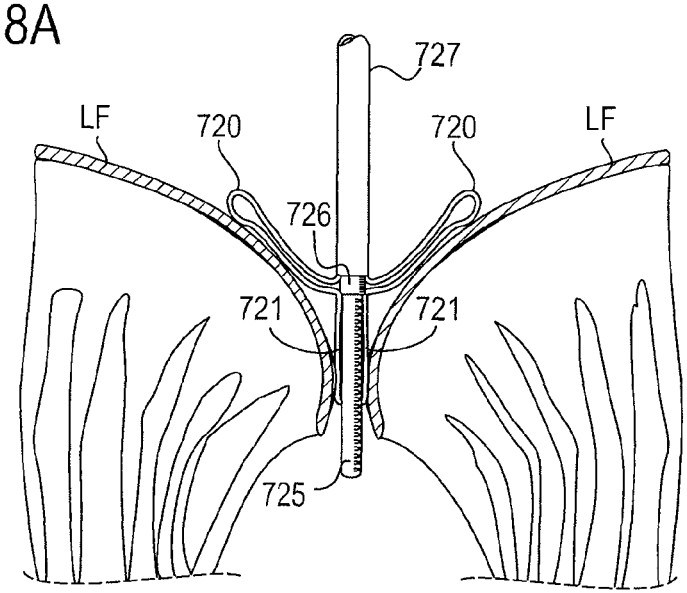

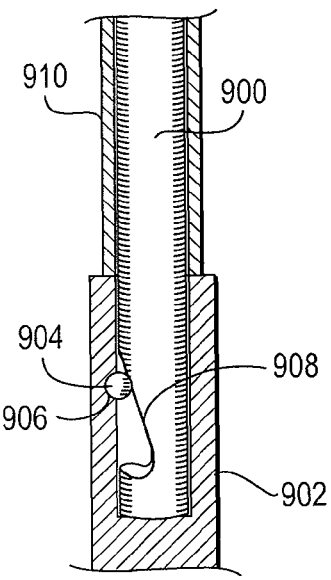
Fig. 21F
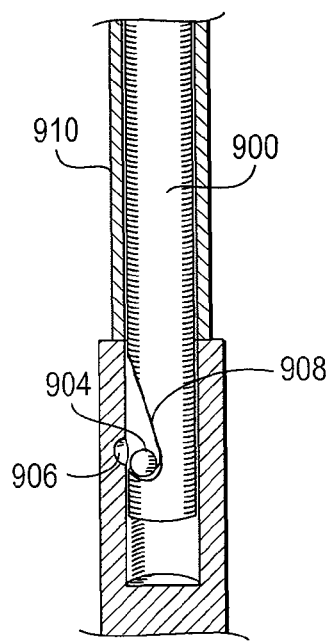
Fig. 21G
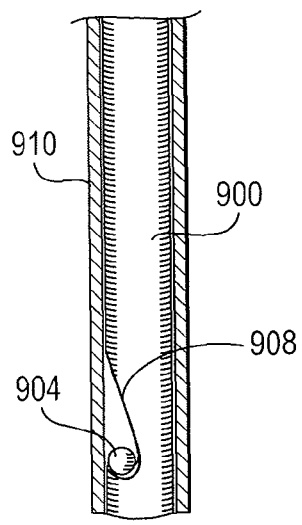
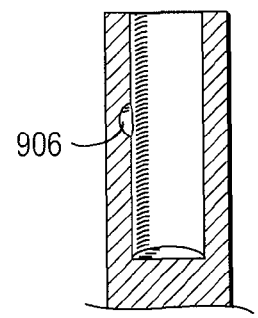
Fig. 21H

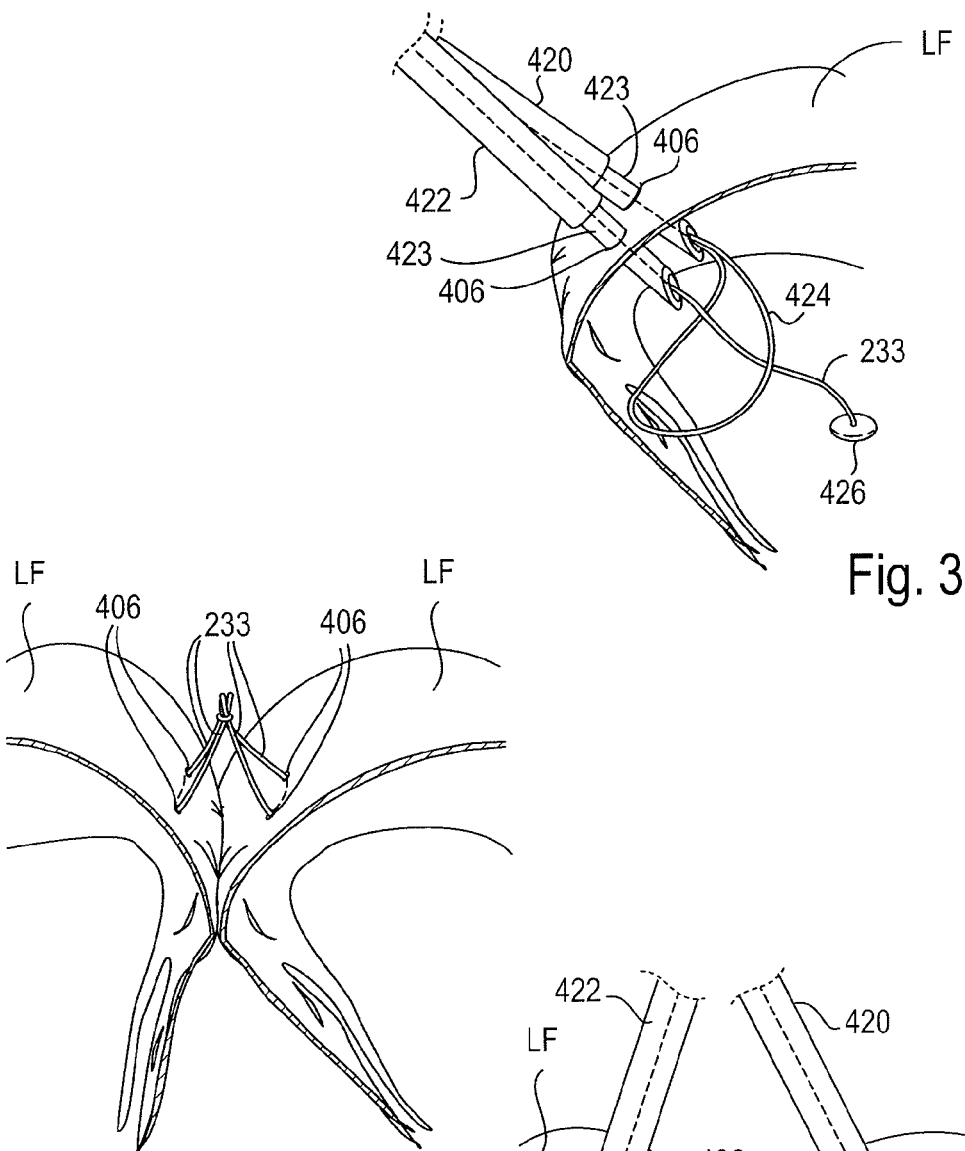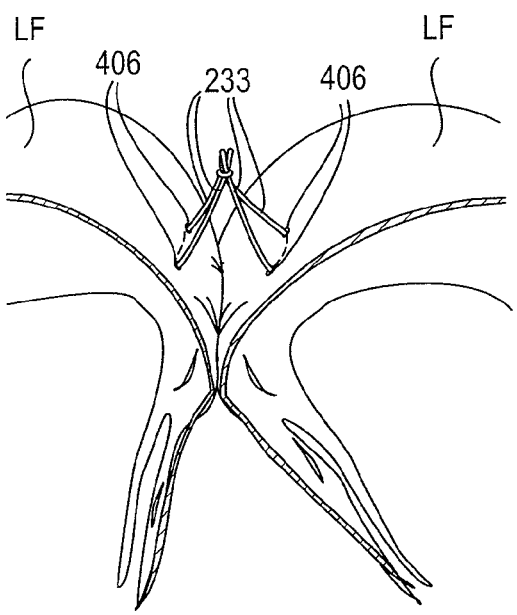
Fig. 31
Fig. 32
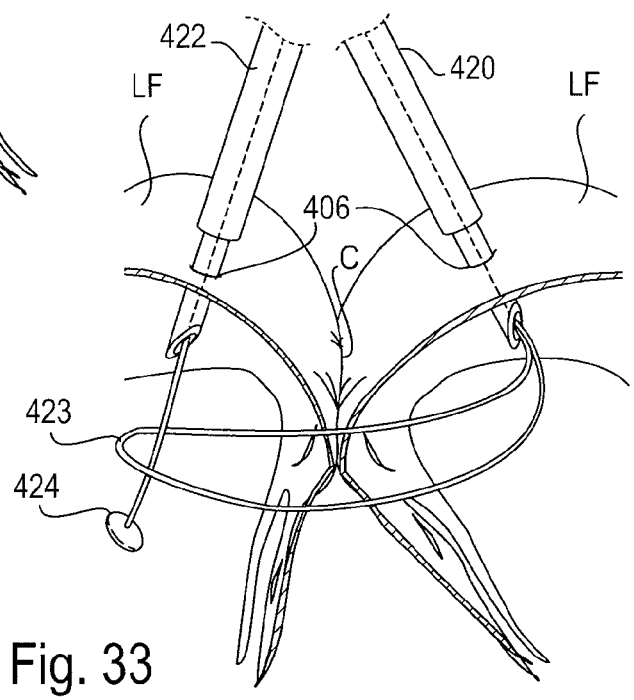
Fig. 33

METHODS AND DEVICES FOR CAPTURING AND FIXING LEAFLETS IN VALVE REPAIR

CROSS-REFERENCES TO RELATED APPLICATIONS

This application is a continuation of U.S. patent application Ser. No. 10/803,444, filed Mar. 17, 2004, which is a continuation of U.S. patent application Ser. No. 09/894,463, filed Jun. 27, 2001 (now U.S. Pat. No. 6,752,813), which was a continuation-in-part of, and claims the benefit of priority from, U.S. patent application Ser. No. 09/544,930, filed Apr. 7, 2000 (now U.S. Pat. No. 6,629,534), which is claims the benefit of prior Provisional Application No. 60/128,690, filed on Apr. 9, 1999 under 37 CFR §1.78(a), the full disclosures of which are hereby incorporated herein by reference.

BACKGROUND OF THE INVENTION

1. Field of the Invention

The present invention relates generally to medical methods, devices, and systems. In particular, the present invention relates to methods, devices, and systems for the endovascular or minimally invasive surgical repair of the valves of the heart, particularly the mitral valve.

Mitral valve regurgitation can result from a number of different mechanical defects in the mitral valve. The valve leaflets, the valve chordae which connect the leaflets to the papillary muscles, or the papillary muscles themselves may be damaged or otherwise dysfunctional. Commonly, the valve annulus may be damaged, dilated, or weakened limiting the ability of the mitral valve to close adequately against the high pressures of the left ventricle.

Mitral valve regurgitation can result from a number of different mechanical defects in the mitral valve. The valve leaflets, the valve chordae which connect the leaflets to the papillary muscles, or the papillary muscles themselves may be damaged or otherwise dysfunctional. Commonly, the valve annulus may be damaged, dilated, or weakened limiting the ability of the mitral valve to close adequately against the high pressures of the left ventricle.

The most common treatments for mitral valve regurgitation rely on valve replacement or strengthening of the valve annulus by implanting a mechanical support ring or other structure. The latter is generally referred to as valve annuloplasty. A recent technique for mitral valve repair which relies on suturing adjacent segments of the opposed valve leaflets together is referred to as the "bow-tie" or "edge-to-edge" technique. While all these techniques can be very effective, they usually rely on open heart surgery where the patient's chest is opened, typically via a sternotomy, and the patient placed on cardiopulmonary bypass. The need to both open the chest and place the patient on bypass is traumatic and has associated morbidity.

For these reasons, it would be desirable to provide alternative and additional methods, devices, and systems for performing the repair of mitral and other cardiac valves, particularly the tricuspid and aortic valves. Such methods, devices, and systems should preferably not require open chest access and be capable of being performed either endovascularly, i.e., using devices which are advanced to the heart from a point in the patient's vasculature remote from the heart or by a minimally invasive approach. Still more preferably, the methods, devices, and systems should not require that the heart be bypassed, although the methods, devices, and systems should be useful with patients who are bypassed and/or whose heart may be temporarily stopped by drugs or other techniques. At least some of these objectives will be met by the inventions described hereinbelow.

2. Description of the Background Art

Minimally invasive and percutaneous techniques for coapting and modifying mitral valve leaflets to treat mitral valve regurgitation are described in WO 98/35638; WO 99/00059; WO 99/01377; and WO 00/03759.

Maisano et al. (1998) Eur. J. Cardiothorac. Surg. 13:240-246; Fucci et al. (1995) Eur. J. Cardiothorac. Surg. 9:621-627; and Umana et al. (1998) Ann. Thorac. Surg. 66:1640-1646, describe open surgical procedures for performing "edge-to-edge" or "bow-tie" mitral valve repair where edges of the opposed valve leaflets are sutured together to lessen regurgitation. Dec and Fuster (1994) N. Engl. J. Med. 331:1564-1575 and Alvarez et al. (1996) J. Thorac. Cardiovasc. Surg. 112:238-247 are review articles discussing the nature of and treatments for dilated cardiomyopathy.

Mitral valve annuloplasty is described in the following publications. Bach and Bolling (1996) Am. J. Cardiol. 78:966-969; Kameda et al. (1996) Ann. Thorac. Surg. 61:1829-1832; Bach and Bolling (1995) Am. Heart J. 129: 1165-1170; and Bolling et al. (1995) 109:676-683. Linear segmental annuloplasty for mitral valve repair is described in Ricchi et al. (1997) Ann. Thorac. Surg. 63:1805-1806. Tricuspid valve annuloplasty is described in McCarthy and Cosgrove (1997) Ann. Thorac. Surg. 64:267-268; Tager et al. (1998) Am. J. Cardiol. 81:1013-1016; and Abe et al. (1989) Ann. Thorac. Surg. 48:670-676.

Percutaneous transluminal cardiac repair procedures are described in Park et al. (1978) Circulation 58:600-608; Uchida et al. (1991) Am. Heart J. 121: 1221-1224; and Ali Khan et al. (1991) Cathet. Cardiovasc. Diagn. 23:257-262.

Endovascular cardiac valve replacement is described in U.S. Pat. Nos. 5,840,081; 5,411,552; 5,554,185; 5,332,402; 4,994,077; and 4,056,854. See also U.S. Pat. No. 3,671,979 which describes a catheter for temporary placement of an artificial heart valve.

Other percutaneous and endovascular cardiac repair procedures are described in U.S. Pat. Nos. 4,917,089; 4,484,579; and 3,874,338; and WO 91/01689.

Thoracoscopic and other minimally invasive heart valve repair and replacement procedures are described in U.S. Pat. Nos. 5,855,614; 5,829,447; 5,823,956; 5,797,960; 5,769,812; and 5,718,725.

BRIEF SUMMARY OF THE INVENTION

The present invention provides methods, devices, and systems for the endovascular repair of cardiac valves, particularly the atrioventricular valves which inhibit back flow of blood from a heart ventricle during contraction (systole), most particularly the mitral valve between the left atrium and the left ventricle. By "endovascular," it is meant that the procedure(s) of the present invention are performed with interventional tools and supporting catheters and other equipment introduced to the heart chambers from the patient's arterial or venous vasculature remote from the heart. The interventional tools and other equipment may be introduced to the vasculature percutaneously, i.e., through an access sheath placed through the skin, or may be introduced via a surgical cut down, and then advanced from the remote access site through the vasculature to the heart. Thus, the procedures of the present invention will generally not require penetrations made directly through the exterior heart muscle, i.e., myocardium, although there may be some instances where penetrations will be made interior to the heart, e.g., through the interatrial septum to provide for a desired access route. While the procedures of the present invention will usually be percutaneous and intravascular, many of the tools will find use in minimally invasive and open surgical procedures as well. In particular, the tools for repositioning the valve leaflets prior to attachment can find use in virtually any type of procedure for modifying cardiac valve function.

Although the methods, devices, and systems of the present invention may be used for the endovascular repair of any of the cardiac valves, the majority of the description will be in regards to the repair of atrioventricular valves. The atrioventricular valves are located at the junctions of the atria and their respective ventricles. The atrioventricular valve between the right atrium and the right ventricle has three valve leaflets (cusps) and is referred to as the tricuspid or right atrioventricular valve. The atrioventricular valve between the left atrium and the left ventricle is a bicuspid valve having only two leaflets (cusps) and is generally referred to as the mitral valve. In both cases, the valve leaflets are connected to the base of the atrial chamber in a region referred to as the valve annulus, and the valve leaflets extend generally downwardly from the annulus into the associated ventricle. In this way, the valve leaflets open during diastole when the heart atria fills with blood, allowing the blood to pass into the ventricle. During systole, however, the valve leaflets are pushed together and closed to prevent back flow of blood into the atria. Thus, the valve leaflets each have generally two planar surfaces, a surface facing the atrium which may be referred to as the atrial surface and a surface facing the ventricle which may be referred to as the ventricular surface. Such terminology may be used with cardiac valves which do not straddle an atrium and a ventricle. In these cases, it is understood that such terminology may be used to suitably describe the corresponding valve surfaces.

Alternatively, the surfaces of the valves may be described in relation to flow direction. For example, since valve leaflets each have two planar surfaces, a surface facing upstream may be referred to as the upstream surface and a surface facing downstream may be referred to as the downstream surface. In the case of the mitral valve, the atrial surface would be the upstream surface and the ventricular surface would be the downstream surface. In the case of the aortic valve, the ventricular surface would be the upstream surface and the surface facing the aorta would be the downstream surface. Such terminology may be most relevant when considering the natural shape of the leaflets since the shape is more related to direction of flow than orientation of the valve in the heart.

Interventions according to the present invention are generally directed at the valve leaflets. It will be the general purpose of such interventions to modify the manner in which the valve leaflets coapt or close during systole so that back flow or regurgitation is minimized or prevented. While the procedures of the present invention will be most useful with the atrioventricular valves, at least some of the tools described hereinafter may be useful in the repair of other cardiac valves, particularly the aortic valve.

The methods of the present invention will usually include accessing a patient's vasculature at a location remote from the heart and advancing an interventional catheter having a capturing device through the vasculature to a location near a cardiac valve to be repaired. The methods may include applying an upward force against a downstream surface of at least one leaflet of the cardiac valve with the capturing device. Such application of force will reposition at least one leaflet so as to reduce leakage through the valve during ventricular systole. Typically, two or more leaflets are repositioned in this manner to achieve desired coaptation. The interventional tool may comprise an elongate shaft having a proximal end and a distal end wherein the capture device is disposed near the distal end. The capture device may comprise at least one distal element capable of protruding radially outward from the shaft. The above described application of force may be achieved by pressing a distal element of the capture device against the downstream surface of the leaflet.

In a first aspect of the methods of the present invention, the distal element may be adjusted prior to or after pressing the distal element against the surface of the leaflet. Such adjustment may include adjusting the length of protrusion of the distal element from the shaft. This may be achieved by retracting or extending the distal element. This allows the capture device to be advanced to the valve in a low profile arrangement and the distal elements to be extended for use once the capture device has been positioned in a desired orientation in relation to the valve. When adjustment of the length is performed after the distal element is in contact with the valve leaflet, such adjustment may serve to reposition the valve leaflet. In addition, adjustment may include adjusting the curvature of the distal element. Adjustment of the curvature may also be achieved by retracting or extending the distal element. Again, if this adjustment step is performed after the distal element is in contact with the leaflet, such adjustment in curvature may serve to reposition the valve leaflet. In some embodiments, the capture device may optionally comprise at least one proximal element capable of protruding radially outward from the shaft and the methods of the present invention may further include holding one or more leaflets between the proximal and distal elements. In this case, adjusting the length and/or curvature of the proximal or distal elements may serve to reposition the captured valve leaflets. Such adjustment of the proximal and distal elements may be achieved simultaneously. In an additional aspect, the proximal and distal elements may interlock for added grasping strength.

In a second aspect of the methods of the present invention, flow through the valve may be observed to determine if regurgitation has been inhibited by the leaflet repositioning. Such observation may be achieved by any suitable means. If the regurgitation has not been sufficiently inhibited, the application of upward force on at least one valve leaflet with the capturing device may be adjusted. This may be achieved with any of the adjustment steps previously described and/or by decreasing or removing any of the upward force against one or more valve leaflets. The observation and adjustment steps may be repeated any number of times until the regurgitation has been sufficiently inhibited.

In a third aspect of the methods of the present invention, the leaflets may optionally be fixed together. Fixing may include fastening, suturing, clipping, stapling, riveting, gluing, or fusing the leaflets together. Alternatively, the capturing tool may be detached from the interventional tool to serve as a fixation device. This involves activating a detachment or decoupling mechanism which allows the capture tool to separate from the interventional tool to be left behind as a permanent implant.

In a fourth aspect of the methods of the present invention, one or more valve leaflets may be atraumatically captured with the capturing device and the captured leaflets may be repositioned independently of each other. When the capture device comprises at least one distal element capable of protruding radially outward from the shaft, a leaflet may be atraumatically captured by pressing the distal element against the leaflet surface. The captured leaflets may be independently repositioned by independently adjusting the distal elements. Likewise, when the capture device comprises at least one proximal element and one distal element, each capable of protruding radially outward from the shaft, the atraumatically capturing step comprises holding the leaflet between the proximal and distal elements. The captured leaflets may be independently repositioned by simultaneously retracting or extending the proximal element and distal element disposed on opposite sides of the leaflet. Again, once the leaflets have been repositioned to a desired orientation, the leaflets may be fixed together by any suitable means including detaching the capture device from the interventional tool and leaving it behind.

In a fifth aspect of the methods of the present invention, the valve leaflets, each leaflet comprising a proximal side and a distal side, may be repaired with the use of sutures having attached anchors. To begin, a first leaflet may be penetrated from the proximal side to the distal side of the leaflet with a penetrating device. In this case, at least a portion of first anchor having a first attached suture is then deployed on the distal side of the first leaflet. A second leaflet is penetrated from the proximal side to the distal side with a penetrating device. Such a penetrating device may be the same penetrating device as penetrated the first leaflet or a separate penetrating device. At least a portion of a second anchor having a second attached suture is deployed on the distal side of the second leaflet. The first and second sutures are then secured together. By securing the sutures together, the valve is repaired by fixing the leaflets together in the desired coapted orientation. Typically, the anchors are disposed in or on the penetrating devices. For example, the anchors may be loaded within a lumen in the penetrating devices or mounted externally on a penetrating device. In any case, the deploying steps comprise releasing the anchors from the respective penetrating devices. In many cases, the anchors are expanded to provide anchoring support on the distal side of the leaflet to prevent the anchor from passing through the penetration and releasing the suture. The anchors may be self-expanding or the deploying steps may further comprise expanding the anchors.

As an alternative, anchors may be used simply to aid in the placement of sutures wherein the anchors are removed prior to securing the sutures together. In this case, again, a first leaflet is penetrated from the proximal side to the distal side of the leaflet with a penetrating device. And, at least a portion of a first anchor having a first attached suture is deployed on the distal side of the first leaflet. The first leaflet is again penetrated from the proximal side to the distal side with a penetrating device, however, this time at a new location. At this new location, a snare is deployed on the distal side of the leaflet so that the snare captures at least part of the first anchor. The snare is then retracted so that the anchor is drawn through the penetration of the snare. By drawing the anchor through the penetration to the proximal side of the leaflet, the suture line effectively passes from the proximal side of the leaflet through a penetration to the distal side traversing a portion of the distal side of the leaflet and then passing through a separate penetration back to the proximal side of the leaflet. This may be repeated on a second leaflet in a similar manner. The four portions of suture on the proximal side of the leaflets may then be secured together. This method may be repeated at any number of locations on the leaflet to create any number of suture lines on the proximal side of the leaflet for securing together. Additional suture lines may provide added fixation strength or possible repositioning of the leaflets. Likewise, the anchor and snare may be deployed on separate leaflets, respectively, so that a suture line may penetrate a first leaflet from the proximal side to the distal side traverse on the distal side of the leaflet to a second leaflet and then cross back through a penetration on the second leaflet to the proximal side. One or more sutures may be positioned in this manner and secured together as previously described. Also, it may be appreciated that such suture placement may be achieved on the opposite side of the leaflets so that the sutures are secured on the distal side of the leaflets.

The penetrating devices described above may be advanced through guide conduits on the interventional tool. Such guide conduits may be adjusted to direct the penetrating device toward the desired location on the valve leaflet. Adjustment may include extending or retracting the guide conduits or angularly adjusting the guide conduits in relation to the shaft. When the capture device comprises at least one loop which is protrudable radially outward from the shaft, the guide conduit may be positioned so that the conduit guides the penetration device through the loop when the penetration device is advanced. Once the penetrating device has penetrated the leaflet, the loops may be retracted to radially translate the penetration devices and the penetrated leaflets toward the shaft. This may serve to reposition the leaflets in a more desired coapted orientation.

The devices of the present invention will usually include an interventional catheter configured to pass from the remote vasculature of a patient to a position within the heart adjacent to the cardiac valve to be repaired and a capture device on the interventional catheter for capturing at least one valve leaflet. Typically, the capture device includes at least one distal element and optionally includes at least one proximal element. The distal end or proximal elements may be comprised of a number of materials, including wire, ribbon, filaments, or fibers which are made from stainless steel, metals, nitinol, shape memory alloy, polymers, silk, polyester or nylon, to name a few.

In a first aspect of the devices of the present invention, the distal elements of the capture devices may take a number of forms and these forms can take a number of shapes. In a preferred embodiment, the distal elements have the form of loops. The loops may have a petal shape so that when the loops are positioned on opposite sides of the shaft, the loops will form a "figure 8" shape when viewed from the top or bottom. This loop configuration is most suitable for use with valves having two leaflets. It may be appreciated that more than two loops may be present and arranged around the shaft having various distances between the loops. Thus, the looped distal elements may be configured for valves having three leaflets. In another embodiment, the distal element has the form of a block, rod or bar disposed perpendicularly to the shaft. The bar may pivot around a pivot point at the base of the shaft to manipulate the position of the bar. Such manipulation may be achieved with the use of a pullwire extending from the shaft to the bar. Retracting or pulling upwards on the pullwire may pivot the bar around the pivot point. Such pivoting orients the bar to a low profile position so that the interventional tool may more easily be passed through a guide catheter, and further between a set of valve leaflets so that the bar is disposed below the valve. The bar may then be pressed against the downstream surface of the leaflets to grasp and reposition the leaflets.

In a second aspect of the devices of the present invention, the distal elements may be individually repositionable or adjustable. The elements may be extended or retracted by variable amounts for protrusion of various distances from the shaft. Such extension and retraction may also adjust the width of the exposed elements if the width varies radially from the shaft, such as with a petal shape. Further, the elements may have differing angles of curvature. This may be achieved by heat-shaping the elements to have different curvatures, or the curvatures may be adjusted by manipulation by the user. Individual manipulation of the elements allows individually protruding the elements prior to capturing the leaflets to ensure proper orientation and includes individually adjusting the elements after grasping the leaflets to reposition the leaflets. In addition, it may be appreciated that the elements may be extended and retracted simultaneously, if desired.

In a third aspect of the devices of the present invention, the interventional tool comprises proximal elements which are capable of protruding radially outward from the shaft at a location which is proximal to the distal elements. The proximal elements may have any of the forms, shapes, material compositions, features or capabilities described in relation to the distal elements. Thus, the proximal elements may be extended, retracted or similarly adjusted to further orient the captured leaflets. The proximal elements may be deployed separately from the distal elements. For example, the proximal elements may be constrained within a shaft while the distal elements are extended radially outward. The proximal elements may then be released by retracting the shaft. Release of the proximal elements allows them to extend radially outward and downward to contact the valve leaflet. In this arrangement, the valve leaflets are held between the proximal and the distal elements. To assist in holding the leaflets the proximal and/or distal elements may included various friction accessories, such as prongs or windings around the elements such as bands or barbs. Alternatively or in addition, the proximal elements and distal elements may interlock to prevent relative motion between the elements and more securely hold the leaflets.

In some embodiments, the proximal and distal elements are formed from a continuous structure. The continuous structure may be held in a low profile position under tension. When the continuous structure is released and allowed to relax, the reforming of the structure allows the structure to protrude outward at various points along the structure. Each protrusion is similar to an above-described proximal or distal element and functions in a similar manner.

In a fifth aspect of the devices of the present invention, the interventional catheter may include a fixation tool or device. In one embodiment, the capture device may function as a fixation device when left in place. To this end, the capture device may be detachable and be left behind as a permanent or temporary implant. Detachment may be achieved by a variety of different mechanisms and design features.

In other embodiments, the fixation tools are used with the capture device either incorporated into the interventional tool or used in combination with the interventional tool. In many of these embodiments, the fixation tools are advanceable through guide conduits disposed near the distal end of the interventional tool. The guide conduits are used to guide the fixation tools to specific locations on the surfaces of the leaflets. The guide conduits are located proximal to the distal elements and are capable of extending and retracting axially and angularly outward from the shaft. Any angle may be used to target the leaflets at points which are approximately one to twelve millimeters inward or away from the free edge of each leaflet. Typically, the guide conduit is used to introduce a fixation tool comprising a penetrating device or needle. The needle may house a suture having an anchor disposed at the distal end of the suture. The needle is advanced toward a valve leaflet to penetrate the leaflet and emerge from the other side. The anchor may be deployed on the opposite side of the leaflet by passing the anchor through the needle and expanding or allowing it to self-expand after it has exited the needle. Alternatively, the anchor may be mounted on the outside of the needle and covered by a sheath. Retraction or removal of the sheath would allow expansion of the anchor. In any case, after anchor deployment, the needle is then retracted while maintaining the anchor on the distal side of the leaflet. A number of different types of anchors may be used during fixation of the leaflets. Typically the anchor is expandable from a compressed, low profile state, for delivery to the anchoring site, to an expanded state to provide a large enough surface for anchoring support. In addition, the fixation tools may include snares which are deployable on the distal side of the leaflet for capturing at least part of an anchor. The snare may then be retracted to move the anchor, such as to draw the anchor through a penetration in the leaflet. Once the suture is placed through the leaflets, either attached to anchors or free from anchors, the suture ends or lines may then be fixed together by conventional knot tying or any suitable method, including positioning suture fasteners.

The methods, devices and systems of the present invention may be provided in one or more kits for such use. The kits may include an interventional catheter configured to pass from the remote vasculature of a patient to a position within the heart adjacent to a cardiac valve to be repaired, wherein the catheter has a capture device comprising at least one distal element, and instructions for use. The instructions for use may set forth any of the methods of the present invention. Optionally, such kits may further include any of the other systems components described in relation to the present invention and any other materials or items relevant to the present invention.

Other objects and advantages of the present invention will become apparent from the detailed description to follow, together with the accompanying drawings.

BRIEF DESCRIPTION OF THE DRAWINGS

FIG. 2A shows normal closure of the leaflets, while

FIGS. 18A-18D show embodiments of the capture device wherein the valve leaflets are pinched between a superior loop and an inferior loop.

FIGS. 21B-21H illustrates a variety of embodiments of detachment mechanisms.

FIG. 31 illustrates an anchor placed through a target point and a snare placed through an adjacent target point, wherein the snare captures the anchor.

FIG. 32 illustrates sutures placed by the method illustrated in FIG. 31, wherein the sutures are fastened together to repair the valve.

FIG. 33 illustrates the method of FIG. 31 performed on two adjacent valve leaflets.

DETAILED DESCRIPTION OF THE INVENTION

Figure 1:
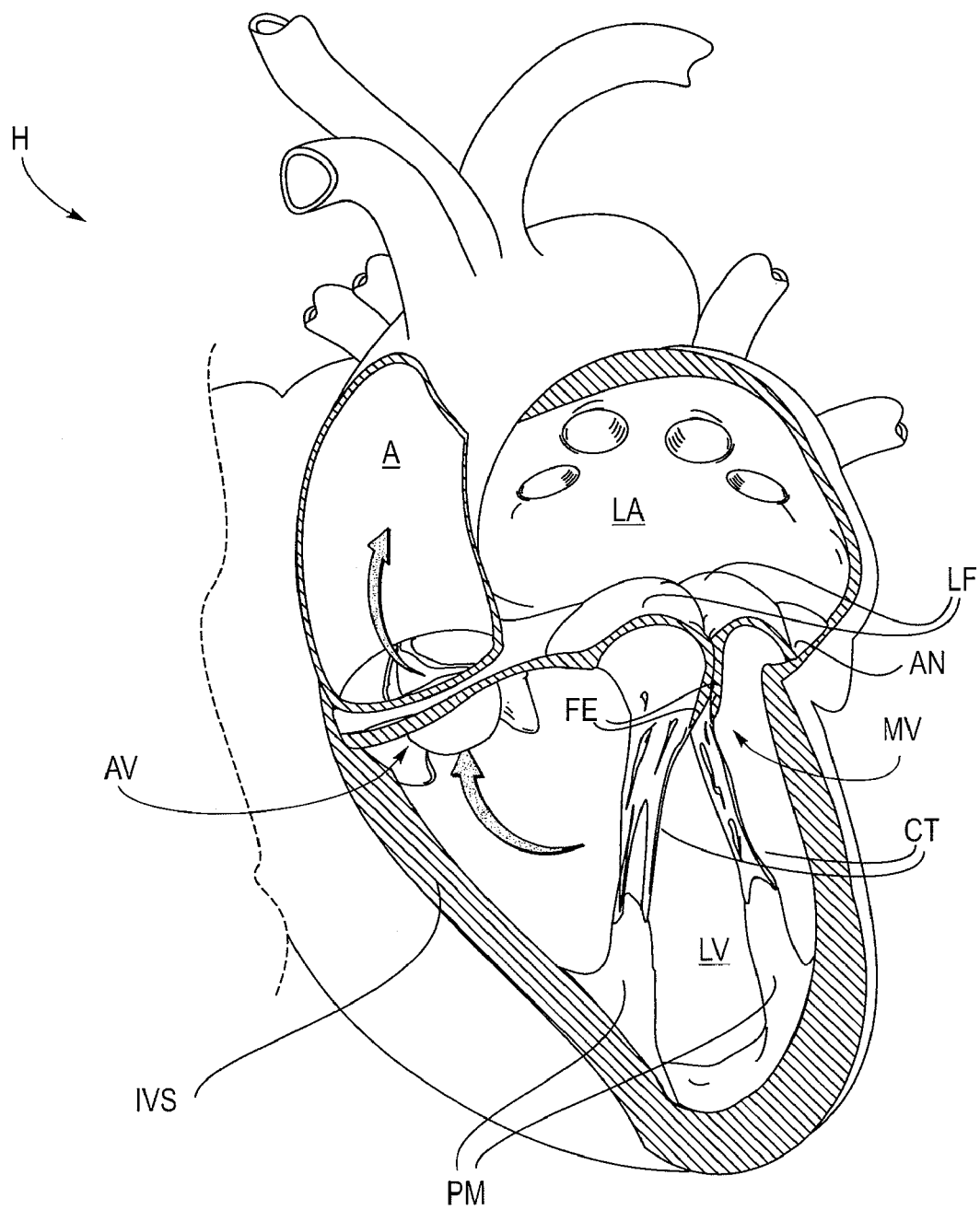
FIG. 1 is a schematic illustration of the left ventricle of a heart showing blood flow during systole with arrows.

I. CARDIAC PHYSIOLOGY. The left ventricle LV of a normal heart H in systole is illustrated in FIG. 1. The left ventricle LV is contracting and blood flows outwardly through the tricuspid (aortic) valve AV in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendineae CT (referred to hereinafter as the chordae) which include plurality of branching tendons secured over the lower surfaces of each of the valve leaflets LF. The chordae CT in turn, are attached to the papillary muscles PM which extend upwardly from the lower portions of the left ventricle and interventricular septum IVS.

Figure 2A:
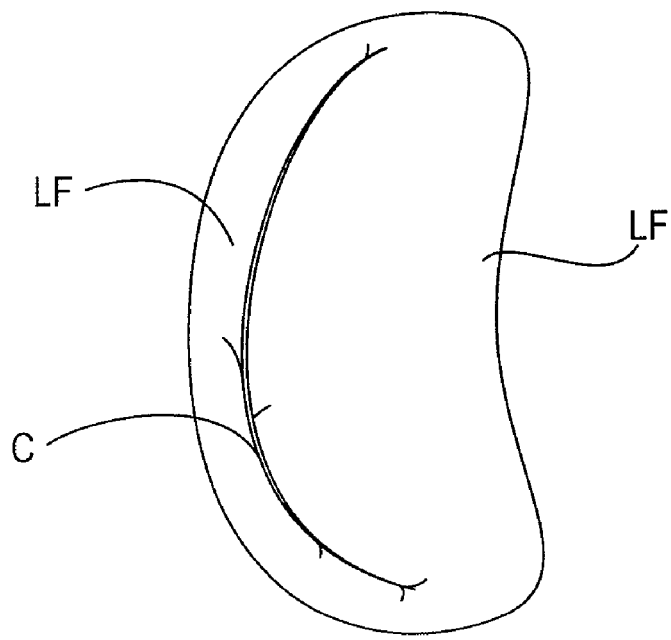
Figure 2B:
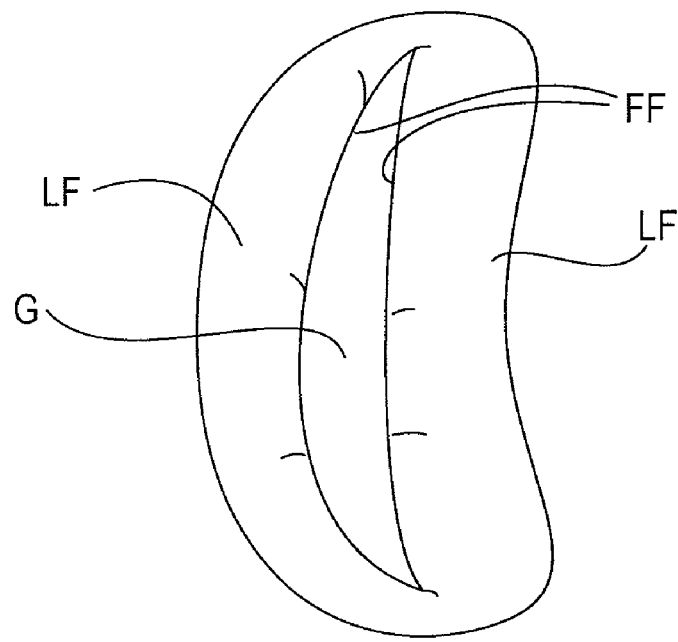
FIG. 2B shows abnormal closure of the leaflets.

A number of structural defects in the heart can cause mitral valve regurgitation. Regurgitation occurs when the valve leaflets do not close properly allowing leakage from the ventricle into the atrium. As shown in FIG. 2A, the free edges of the anterior and posterior leaflets normally meet along a line of coaptation C. An example of a defect causing regurgitation is shown in FIG. 2B. Here an enlargement of the heart causes the mitral annulus to become enlarged, making it impossible for the free edges FE to meet during systole. This results in a gap G which allows blood to leak through the valve during ventricular systole. Ruptured chordae can also cause a valve leaflet to prolapse since inadequate tension is transmitted to the leaflet via the chordae. While the other leaflet maintains a normal profile, the two valve leaflets do not properly meet and leakage from the left ventricle into the left atrium will occur. Such regurgitation can also occur in patients who have suffered ischemic heart disease where papillary muscles do not contract sufficiently to effect proper closure.

II. GENERAL OVERVIEW. The present invention provides methods and devices for grasping, and optional repositioning and fixation of the valve leaflets to treat cardiac valve regurgitation, particularly mitral valve regurgitation. Such grasping will typically be atraumatic providing a number of benefits. For example, atraumatic grasping may allow repositioning of the devices relative to the leaflets and repositioning of the leaflets themselves without damage to the leaflets. However, in some cases it may be necessary or desired to include grasping which pierces or otherwise permanently affects the leaflets. In some of these cases, the grasping step includes fixation. Although a number of embodiments are provided to achieve these results, a general overview of the basic features will be presented herein. Such features are not intended to limit the scope of the invention and are presented with the aim of providing a basis for descriptions of individual embodiments presented later in the application.

Generally, the valve leaflets are grasped and repositioned by pressing a capture device against the ventricular surface of the leaflets. The ventricular surface is the generally planar surface of the valve that faces the ventricle. Access to the ventricular surface will be described in the following section, however it is basically assumed that the ventricular surface is accessible by a retrograde approach through the ventricle or by an antegrade approach through the atrium and then passing through the valve to the ventricle. For illustration purposes, an antegrade approach will be described.

Figure 3:
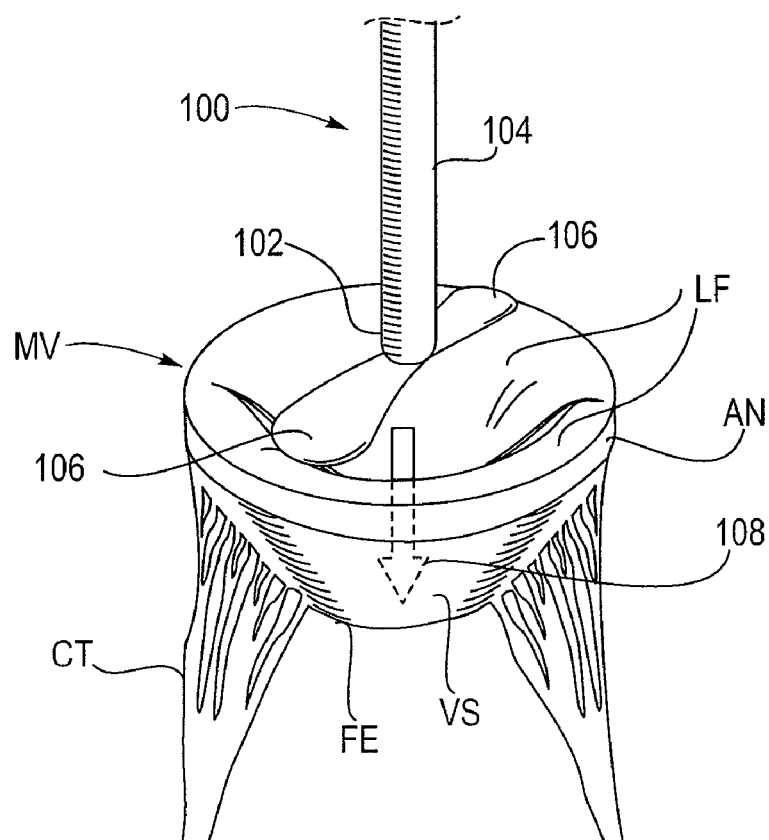
FIG. 3 is a perspective side view of the mitral valve showing an interventional tool approaching the valve leaflets from the atrial side.
Figure 4:
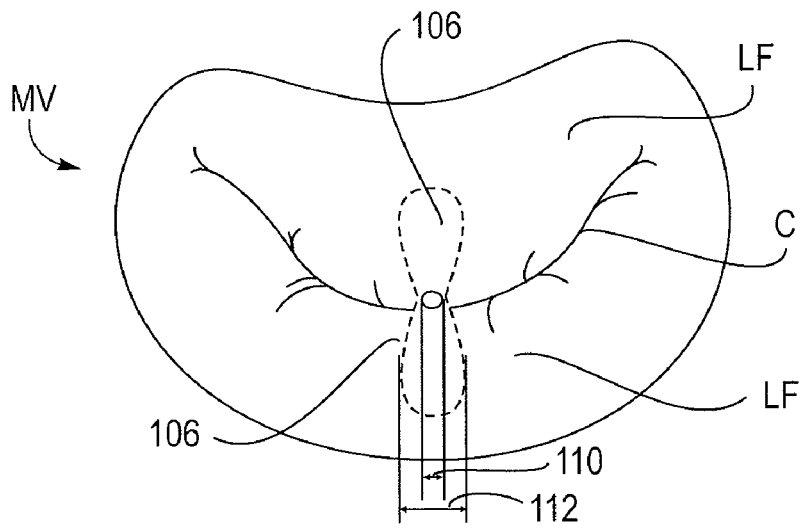
FIG. 4 illustrates a short axis view if the mitral valve from the atrial side wherein elements of the interventional tool are shown in dashed outline as they are positioned on the ventricular side of the valve.

Referring to FIG. 3, a interventional tool 100, having a shaft 104 and a capture device 105 comprising two elements 106 protruding radially outward from the distal end 102 of the shaft 104, is shown approaching the mitral valve MV from the atrial side. The mitral valve MV is shown in a perspective side view wherein the valve leaflets LF open through the valve annulus AN during diastole. In such a position, the chordae CT are can be seen attached along the free edge FE of the leaflet LF and the ventricular surface VS is visible. Short-axis echocardiography may be used to visualize the interventional tool 100 and orient the elements 106 so that they are positioned substantially perpendicular to the line of coaptation C. The tool 100 may be moved roughly along the line of coaptation to the location of regurgitation. Under long-axis echo guidance, the elements 106 are then advanced through the valve, between the leaflets LF in the direction of the arrow 108, so that the elements 106 emerge beyond the valve. In this perpendicular position, the tool 100 is then retracted, pressing the elements 106 against the ventricular surface of the leaflets LF. This grasps the leaflets LF and pulls the leaflets up close to the annular plane so that the grasped free edges are coapted. This is illustrated in FIG. 4, a short-axis view of the mitral valve MV from the atrial side. Here the elements 106 are shown in dashed outline as the elements 106 are positioned on the ventricular side of the valve.

Figure 5:
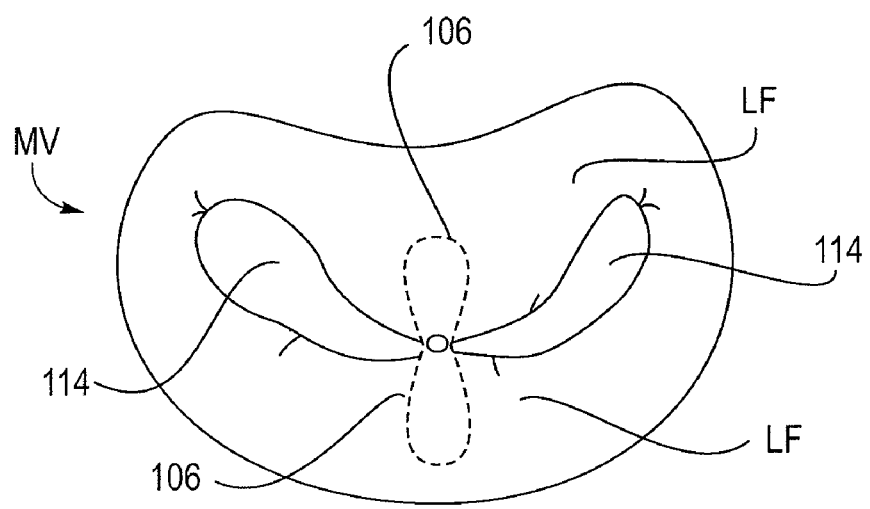
FIG. 5 illustrates the mitral valve as in FIG. 4 during diastole.
Figure 5A:
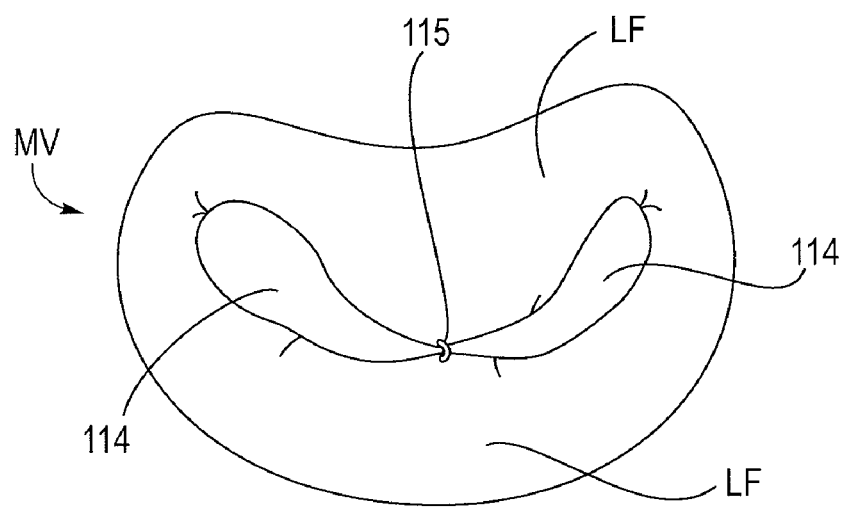
FIG. 5A illustrates the valve leaflets fixed together as in a surgical bow tie repair.

The interventional tool 100 is dimensioned at its waist 110 to fit between adjacent chordae where the chordae attach to the free edge. The elements 106 may be dimensioned to have a width 112 which is greater than the distance between the adjacent chordae, effectively trapping the chordae, however this is not necessary. In addition, the opposing tensioning force of the chordae on the free edge FE of the leaflets helps secure the leaflets LF on the elements 106. Such dimensioning and positioning prevents displacement of the leaflets LF from the interventional tool 100 due to the diastolic pressure gradient on the leaflets LF and relative movement of the annulus to the elements 106. This is shown in FIG. 5, a short-axis view of the mitral valve MV from the atrial side during diastole wherein the leaflets LF remain in position against the elements 106 surrounded by openings 114 which result from the diastolic pressure gradient. This simulates the double orifice geometry of a standard surgical bow-tie repair. Color Doppler echo will show if the regurgitation of the valve has been reduced. If the resulting mitral flow pattern is satisfactory, the leaflets may be fixed together in this orientation with a suture 115 or fixation device, as shown in FIG. 5A. If the resulting color Doppler image shows insufficient improvement in mitral regurgitation, the interventional tool 100 may be repositioned. This may be repeated until an optimal result is produced wherein the leaflets LF may then be fixed.

As will be discussed later, the interventional tool 100 may take a number of forms and may be comprised of a variety of materials, each design choice providing variations to the above described methods and devices. Further, the tool 100 may include provisions for fixing the leaflets together after repositioning. Thus, the above provided description simply sets forth a sampling of basic features of the present invention.

III. ACCESS TO THE MITRAL VALVE. Access to the mitral valve or other cardiac valve will preferably be accomplished through the patient's vasculature in a "percutaneous" manner. By "percutaneous" it is meant that a location of the vasculature remote from the heart is accessed through the skin, such as using needle access through, for example, the Seldinger technique. However, it may also include using a surgical cut down procedure or a minimally invasive procedure. The ability to percutaneously access the remote vasculature is well-known and described in the patent and medical literature. Depending on the point of vascular access, the approach to the mitral valve may be antegrade and require entry into the left atrium via the pulmonary vein or by crossing the interatrial septum. Alternatively, approach to the mitral valve can be retrograde where the left ventricle is entered through the aortic valve. Once percutaneous access is achieved, the interventional tools and supporting catheter(s) will be advanced to the heart intravascularly where they may be positioned adjacent the target cardiac valve in a variety of manners, as described elsewhere herein. While the methods will preferably be percutaneous and intravascular, many of the tools and catheters described herein will, of course, also be useful for performing open surgical techniques where the heart is beating or stopped and the heart valve accessed through the myocardial tissue. Many of the devices will also find use in minimally invasive procedures where access is achieved thorascopically and where the heart will usually be stopped but in some instances could remain beating.

Figure 6:
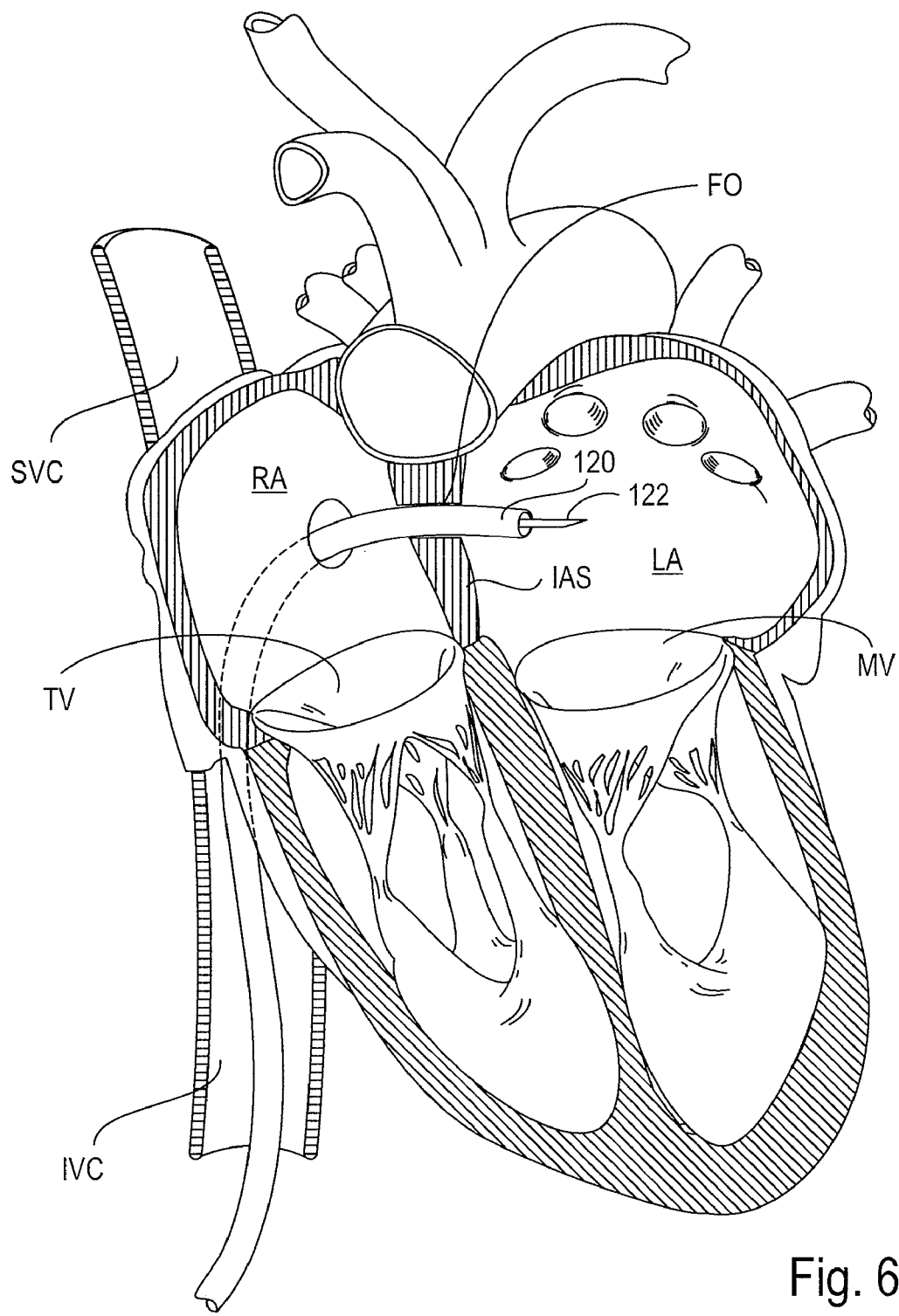
FIGS. 6-7 show exemplary antegrade approaches to the mitral valve from the venous vasculature.
Figure 7:
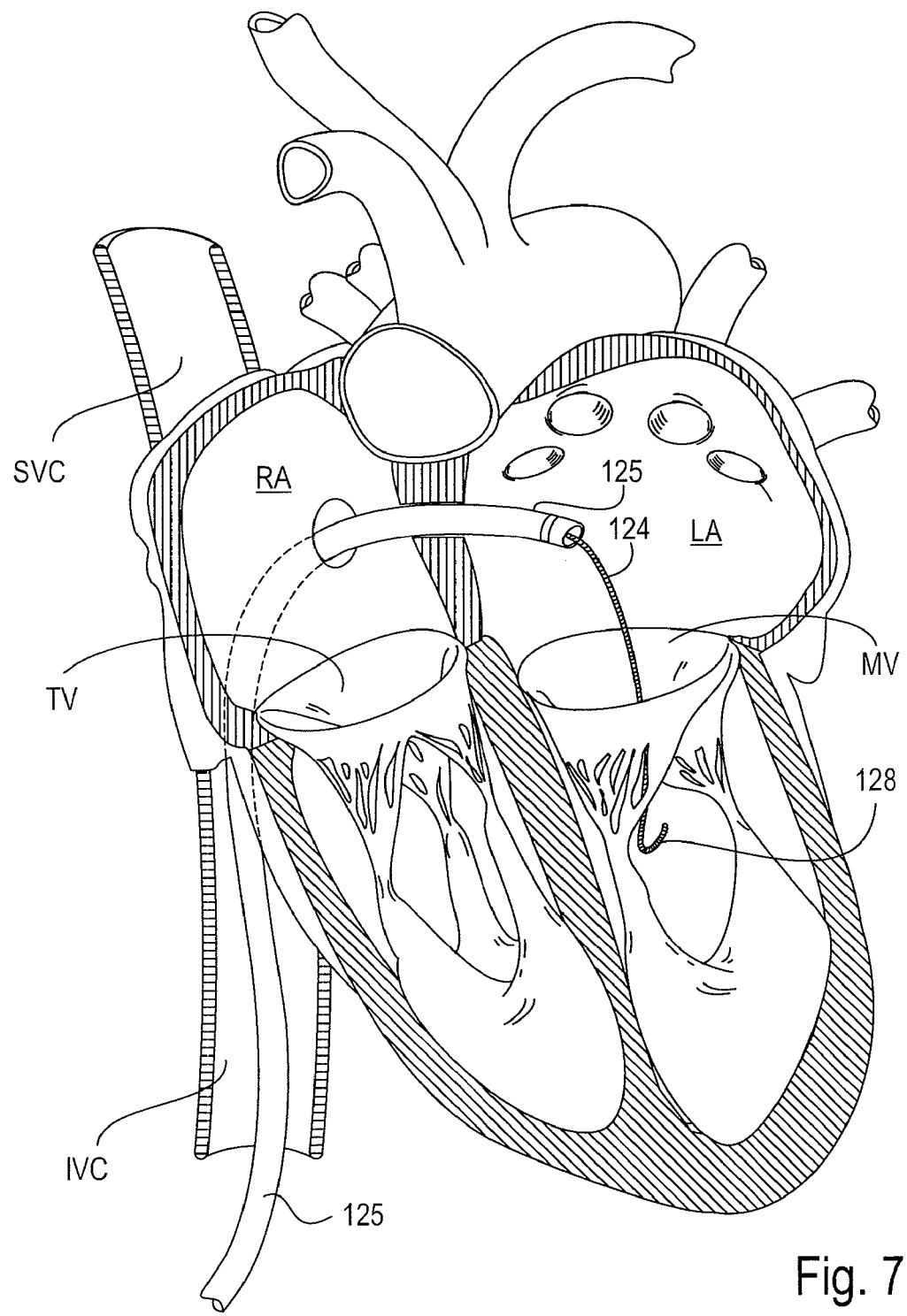

A typical antegrade approach to the mitral valve is depicted in FIG. 6. The mitral valve MV may be accessed by a standard approach from the inferior vena cava IVC or superior vena cava SVC, through the right atrium RA, across the interatrial septum IAS and into the left atrium LA above the mitral valve MV. As shown, a catheter 120 having a needle 122 may be advanced from the inferior vena cava IVC into the right atrium RA. Once the catheter 120 reaches the interatrial septum IAS, the needle 122 may be advanced so that it penetrates through the septum at the fossa ovalis FO or the foramen ovale into the left atrium LA. At this point, a guidewire may be advanced out of the needle 122 and the catheter 120 withdrawn. As shown in FIG. 7, access through the interatrial septum IAS will usually be maintained by the placement of a guide catheter 125, typically over a guidewire 124 which has been placed as described above. The guide catheter 125 affords subsequent access to permit introduction of the tool(s) which will be used for performing the valve or tissue modification, as described in more detail below.

Figure 8:
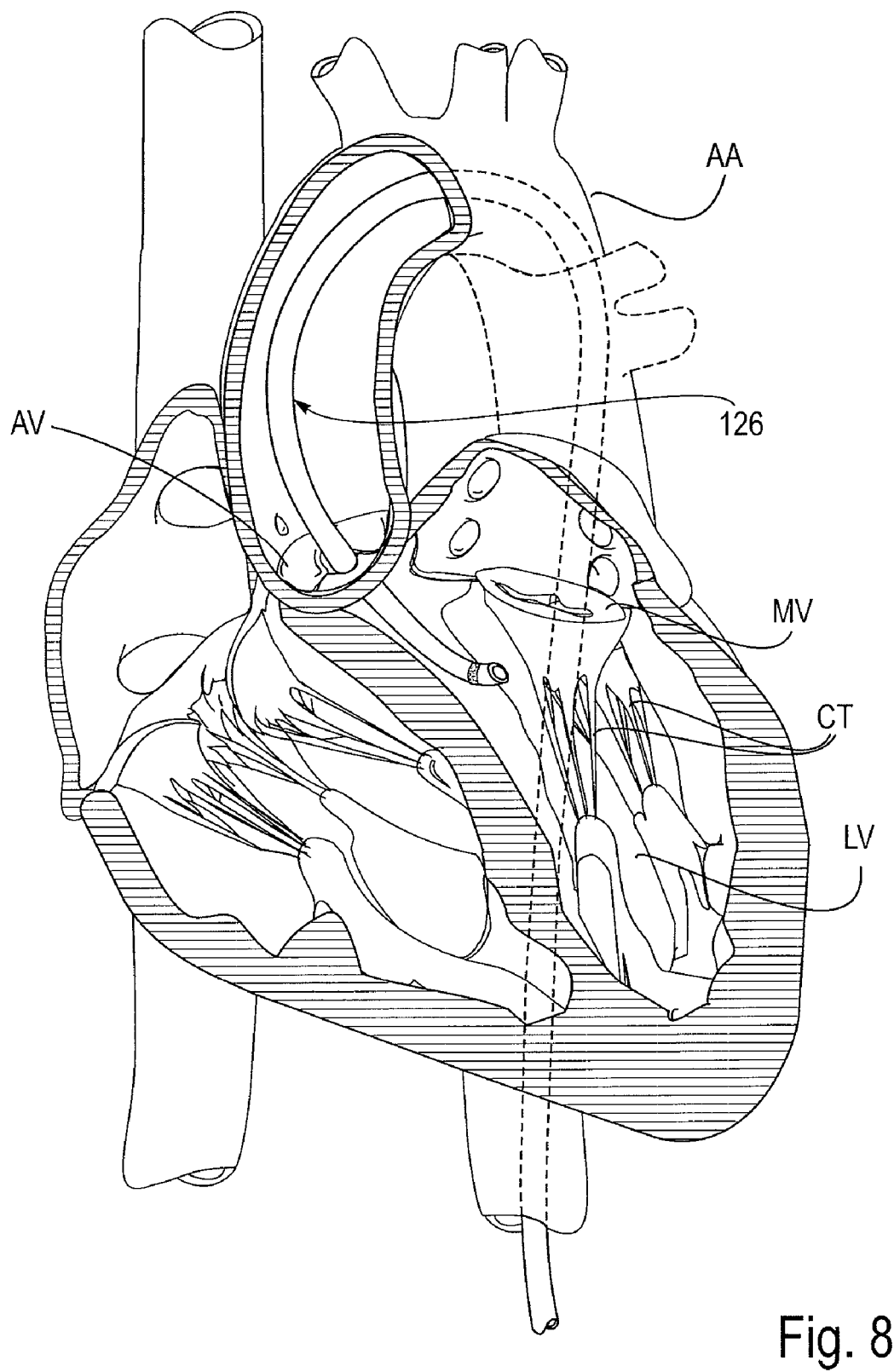
FIGS. 8-9 show exemplary retrograde approaches to the mitral valve through the aortic valve and atrial vasculature.
Figure 9:
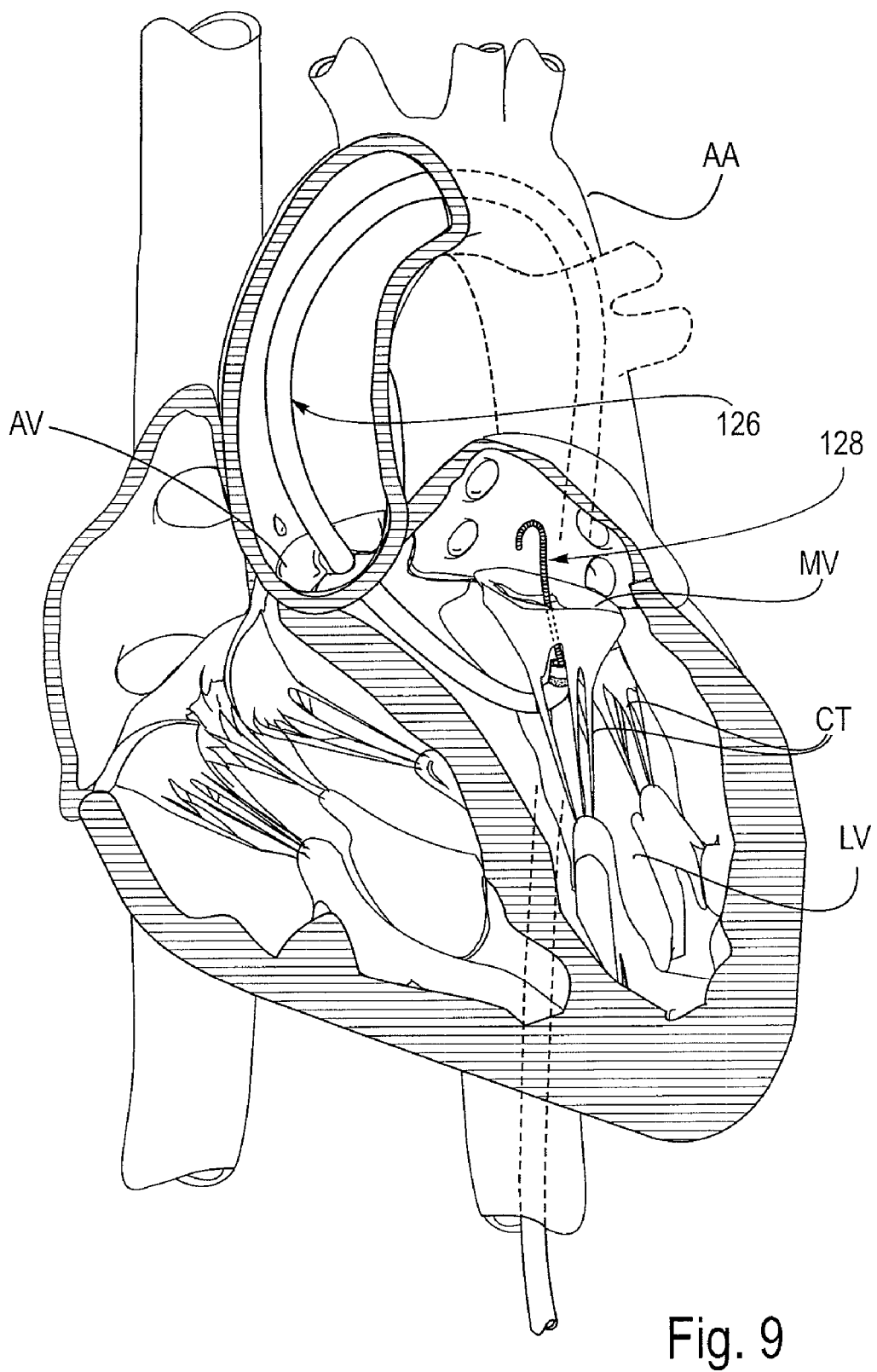

A typical retrograde approach to the mitral valve is depicted in FIG. 8. Here the mitral valve MV may be accessed by an approach from the aortic arch AA, across the aortic valve AV, and into the left ventricle below the mitral valve MV. The aortic arch AA may be accessed through a conventional femoral artery access route, as well as through more direct approaches via the brachial artery, axillary artery, or a radial or carotid artery. As shown in FIG. 9, such access may be achieved with the use of a guidewire 128. Once in place, a guide catheter 126 may be tracked over the guidewire 128. The guide catheter 126 affords subsequent access to permit introduction of the tool(s) which will be used for performing the valve modification, as described in more detail below.

In some cases, access routes to the mitral valve may be established in both antegrade and retrograde approach directions. This may be useful when, for instance, grasping is performed with the use of specific devices introduced through one route and fixation is achieved with the use of separate devices introduced through another route. In one possible situation, the leaflets may be grasped and repositioned by pressing a interventional tool against the ventricular surface of the valve via a retrograde approach. While the interventional tool is in place, a fixation tool may be introduced via an antegrade approach to fix the leaflets in place. Thus, a variety of access routes may be used individually or in combination with the methods and devices of the present invention.

IV. LEAFLET CAPTURE DEVICE. Once the valve is accessed and the guidecatheter is positioned in place, the interventional catheter is introduced through the guidecatheter for use in capturing or holding the valve leaflets. The interventional catheter typically comprises a shaft, having a proximal end and a distal end, and an interventional tool disposed near its distal end. The interventional tool may take a number of forms to perform the methods of the present invention. Fundamentally, the interventional tool comprises a capture device comprising at least one distal element capable of protruding radially outward from the shaft. Typically, the tool will have two distal elements, one element to press upwardly against each leaflet of the two leaflet that are to be fixed together. However, the tool may have any number of such elements, including multiple elements pressing against each of the leaflets or one element pressing against one leaflet and no element pressing against an adjacent leaflet. Any of these combinations may effectively coapt a pair of leaflets. Further, multiple elements may be present to reposition and coapt three leaflets, such as for use with the aortic valve.

Figure 10A:
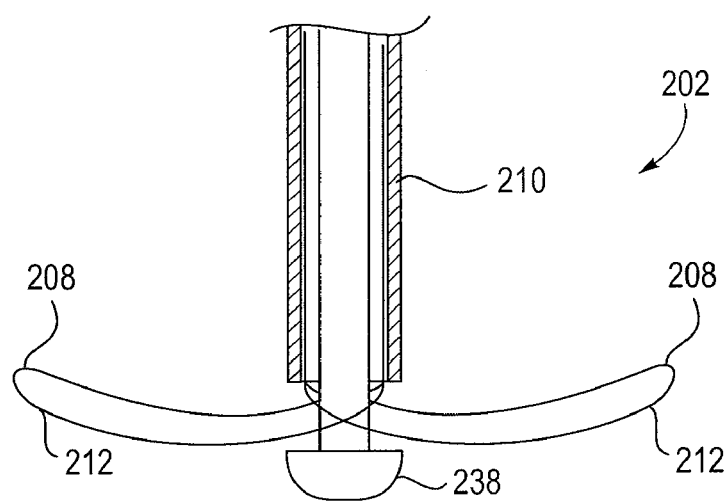
FIGS. 10A-10C show a number of embodiments of capture devices which may be disposed at the distal end of an interventional catheter.
Figure 10B:
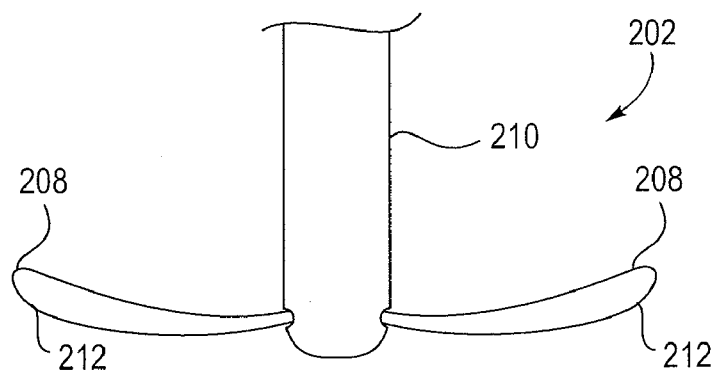
Figure 10C:
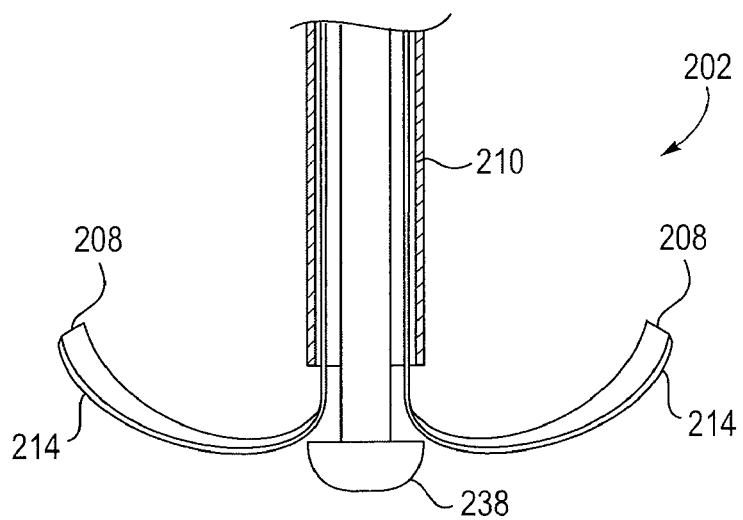

FIGS. 10A-10C show a number of embodiments of capture devices 204 that may be disposed at the distal end 202 of an interventional catheter 200. As described, each device 204 will typically have two distal elements 208 which are protrudable radially outward from the shaft 210. In many embodiments, the elements 208 extend from opposite sides of the shaft 210 so the elements 208 are approximately 180 degrees apart. However, it may be appreciated that the elements 208 may be spaced any distance apart and may be symmetrically or asymmetrically arranged.

In addition, the distal elements 208 may take a number of forms, including bars, rods, flaps, sheets, blocks or loops to name a few. These forms can in turn take a number of shapes, such as rectangular, circular, oblong, elliptical and petal. Further, these forms may be comprised of a number of materials, including wire, ribbon, filaments or fibers which are made from stainless steel, metals, nitinol, shape-memory alloy, polymers, silk, polyester or nylon, to name a few. Such materials may also be radiopaque to aid in visualization. Likewise, the elements may be comprised of a combination of such forms and/or materials. As an example, FIG. 10A illustrates elements 208 in the form of loops 212 having a petal shape. Here, the loops are positioned on opposite sides of the shaft 210 so as to form a "figure-8" shape in a top view or a bottom view. These loops 212 are preferably made from nitinol or shape-memory wire, however other materials may be suitable. The loops 212 may protrude from the shaft 210 by a means of a number of designs. For example, as illustrated in FIG. 10A, the loops may protrude from a space between the shaft 210 and a cap 238 located at its tip. Alternatively, the loops 212 may protrude through the shaft 210, as shown in FIG. 10B, or through the cap 238. This may lend support to the loops 212 during use. As will be discussed later, such loops 212 may be combined with a second set of loops comprised of suture that are detachable from these loops 212 for leaflet fixation. FIG. 10C illustrates elements 208 in the form of flaps or sheets 214 which are essentially rectangular such as made from ribbon or other flat materials. These sheet 214 are also preferably made from nitinol or shape-memory wire, however other materials may be suitable.

Figure 11A:
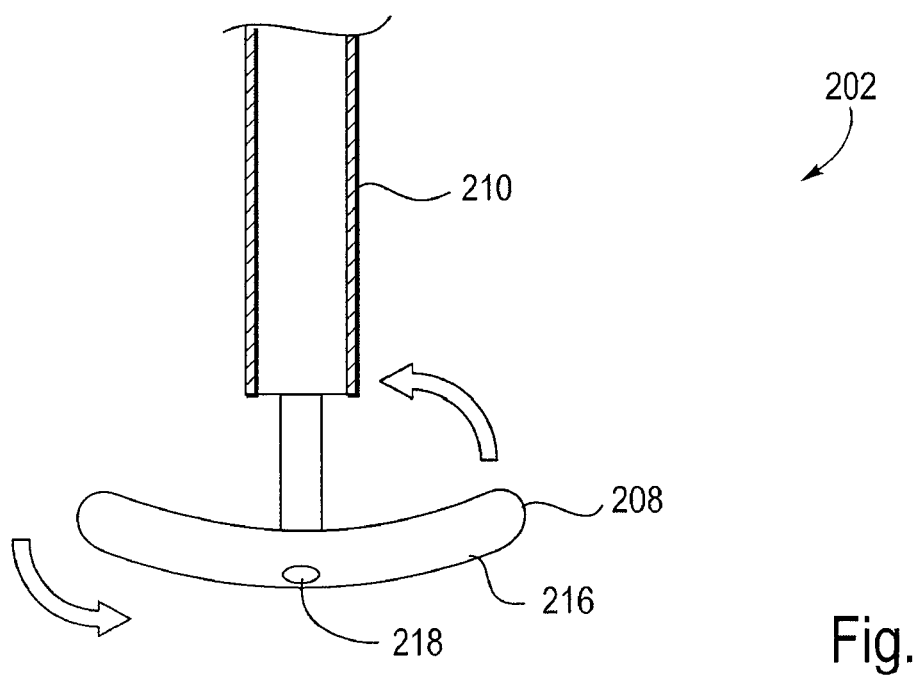
FIGS. 11A-11C and FIG. 12 show a number of embodiments of capture devices wherein an element is in the form of a block, rod, or bar.
Figure 11B:
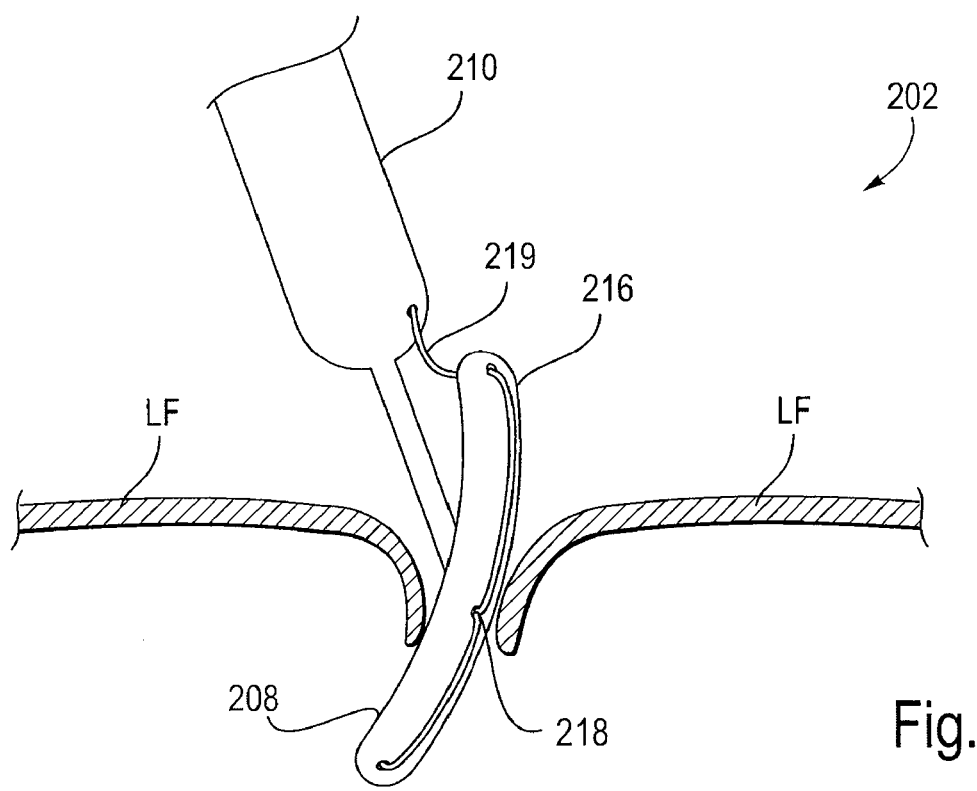
Figure 11C:
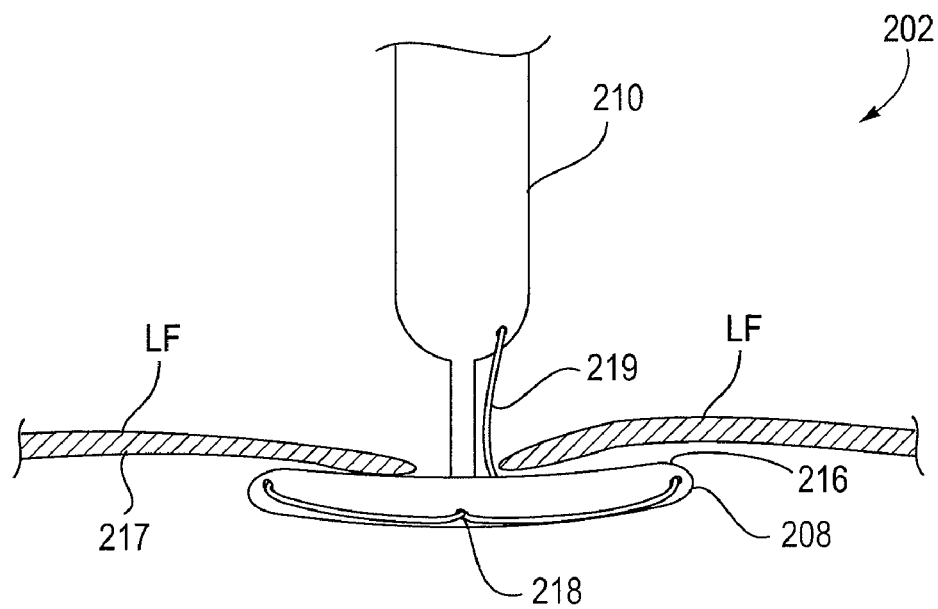

FIG. 11A illustrates a element 208 in the form of a block, rod or bar 216 disposed perpendicularly to the shaft 210. The bar 216 may be comprised of any number of materials, including metals, alloys, polymers or fibers, to name a few. When such a bar 216 forms one continuous element 208 which extends beyond the diameter of the shaft, as shown, the bar 216 may pivot (indicated by arrows) around a pivot point 218 at the base of the shaft 210 to manipulate the position of the bar 216. As shown in FIG. 11B, the bar 216 may further comprise a pull-wire 219 which extends from the shaft 210 to the bar 216 and loops through the bar 216 to connect with each end of the bar 216. By retracting or pulling upwards on the pull-wire 219 the bar 216 will pivot around a pivot point 218 at the base of the shaft 210. This orients the bar 216 to a low profile position so that the interventional tool may more easily be passed through a guidecatheter and further between a set of valve leaflets LF, as shown. Once the element 208 is advanced and disposed below the valve, as shown in FIG. 11C, the element 208 is then pressed against the ventricular surface 217 of the leaflets LF to grasp and reposition the leaflets. Since the bar 216 is pivotable around a center pivot point 218, the bar 216 may slightly pivot during grasping based on the anatomy of the valve. This may allow a more desirable application of force to the valve leaflets, as a less rigid leaflet may receive a larger force to draw the leaflet up to a coapted position. In a similar design, each element 208 may pivot independently of the other around a pivot point at the base of the shaft. This is possible when such a bar or rod forms two elements 208 extending 180 degrees apart outwardly from the shaft 210. This may provide an even higher degree of flexibility during grasping.

Figure 12:
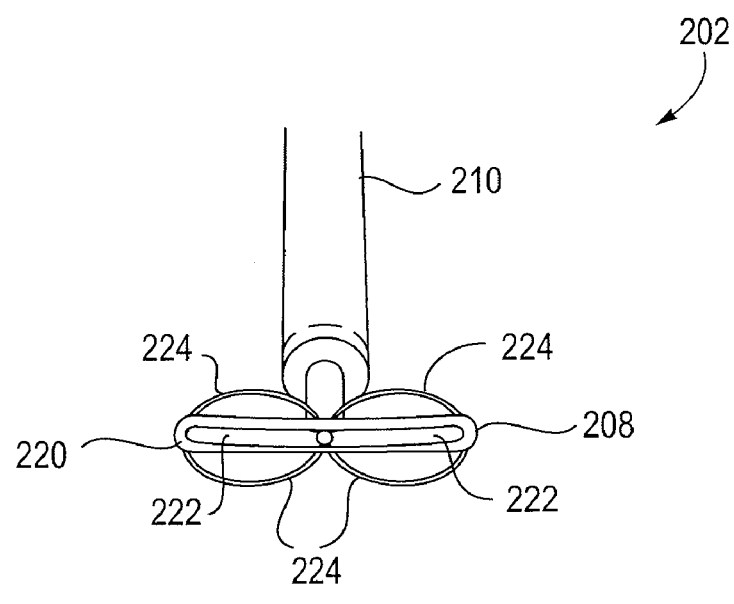

Referring to FIG. 12, the element 208 may be comprised of a combination of forms and materials. Here, the element has the form of a block 220 having cutouts 222 surrounded by wire loops 224. Such loops 224 may increase the area in which the element 208 may contact the leaflet LF. In addition, such loops 224 may be adjustable to aid in manipulation and repositioning of the leaflets. Further, the block 220 may be pivotable around a center pivot point 218 at the base of the shaft 210 to manipulate the position of the block 220 as in the manner described and shown in FIGS. 11B-11C.

Figure 13:
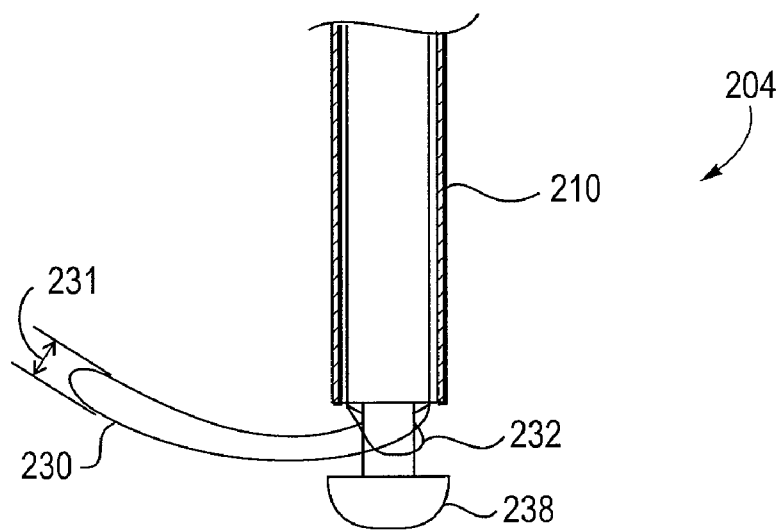
FIG. 13 illustrates the extension of a first element independently of a second element.
Figure 14:
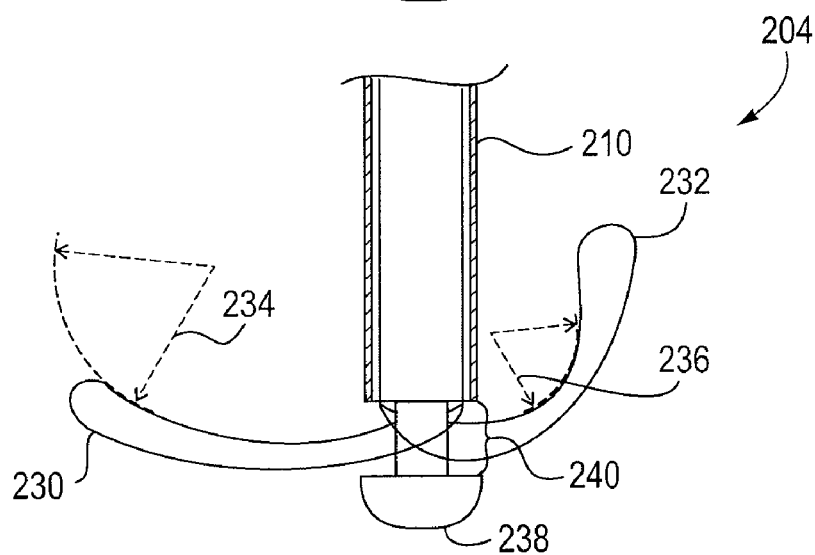
FIG. 14 illustrates elements having differing angles of curvature.

In many embodiments, the distal elements are individually extendable, retractable and repositionable. FIG. 13 illustrates the extension of a first element 230 independently of the second element 232. Such elements 230, 232 may be utilized in this arrangement or the second element 232 may be extended at any point during the procedure. Likewise, the elements 230, 232 may be extended or retracted by variable amounts for protrusion of various distances from the shaft 210. Such extension and retraction may also adjust the width 231 of the exposed elements 230, 232 if the width of the element 230, 232 varies radially from the shaft, such as with a petal shape. In addition, the elements 230, 232 may be individually rotatable around the shaft 210 to vary the distance between the elements 230, 232. Further, as shown in FIG. 14, the elements 230, 232 may have differing angles of curvature. Here, the first element 230 has a first radius of curvature 234 which is larger than a second radius of curvature 236 of the second element 232. This may be achieved by heat shaping the elements 230, 232 to have different curvatures, or the curvatures may be adjusted by manipulation by the user at the proximal end of the interventional catheter 200. Consequently, each element 230, 232 will provide a different repositioning effect when pressed against a leaflet.

Figure 15:
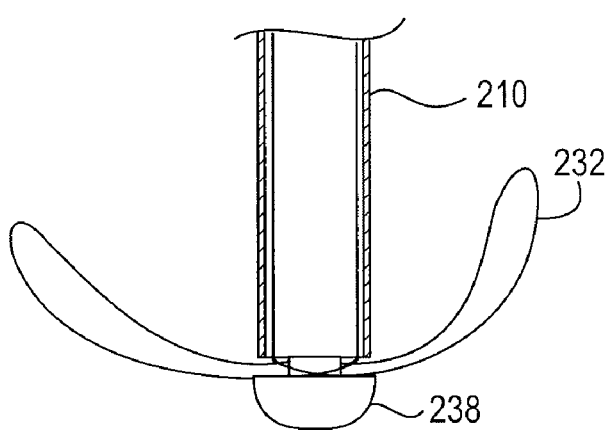
FIG. 15 illustrates a capture device having extended elements pinched between the shaft and the cap.

In some embodiments, the capture device 204 has a cap 238 located at its tip. Such a cap 238 has been shown in embodiments presented in FIGS. 10A, 10C, 13, and 14 and may provide a variety of functions. For example, the cap 238 may serve as a blunt tip to assist in atraumatic passing of the device 204 through the valve, between valve leaflets, during placement of the device 204. The cap 238 may also be moveable to close a gap 240 between the cap 238 and the shaft 210 where the distal elements 230, 232 emerge. When the elements 230, 232 are retracted, movement of the cap 238 to close the gap minimizes the profile of the tool 204 and reduces the possibility of the elements 230, 232 or portions of the device 204 interfering with tissue or entangling with chordae. As shown in FIG. 15, when the elements 230, 232 are extended, movement of the cap 238 to close the gap 240 may increase rigidity of the elements 230, 232 by providing support for the elements 230, 232 or it may adjust the curvature of the elements 230, 232 by flexing a portion of the elements 230, 232 near the shaft 210. Further, when the elements 230, 232 are pressed against the ventricular surface of the valve leaflets, the leaflets may extend into the gap 240 between the cap 238 and the shaft 210. When the cap 238 is moved to close the gap 240, the leaflets may be pinched between the shaft 210 and the elements 230, 232 and cap 238. This may assist grasping of the leaflets for later fixation. It may be appreciated that although these elements have been illustrated as curving upwardly, away from the distal end, the elements may alternatively be uncurved, curve downwardly, include compound curvatures or more than one curvature along each element, or any other combination of curvatures.

Figure 16A:
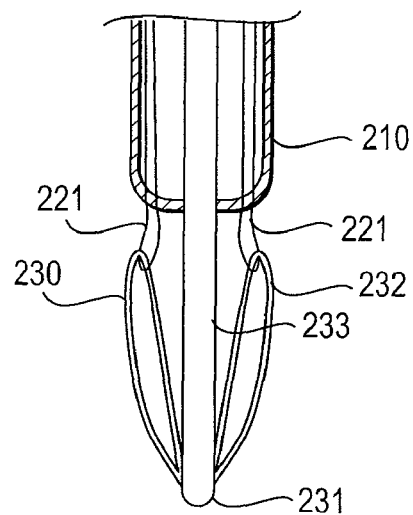
FIGS. 16A-16E illustrate an embodiment of the capture device wherein the distal elements are held in a retracted position under tension and are extendible upon release.
Figure 16B:
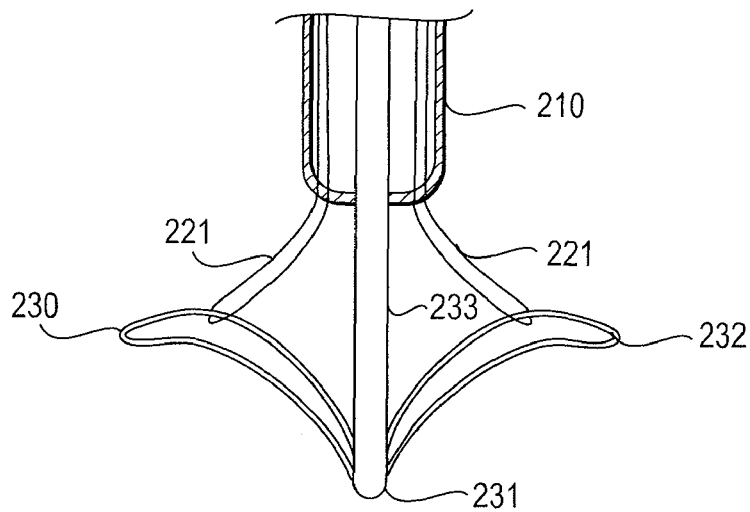
Figure 16C:
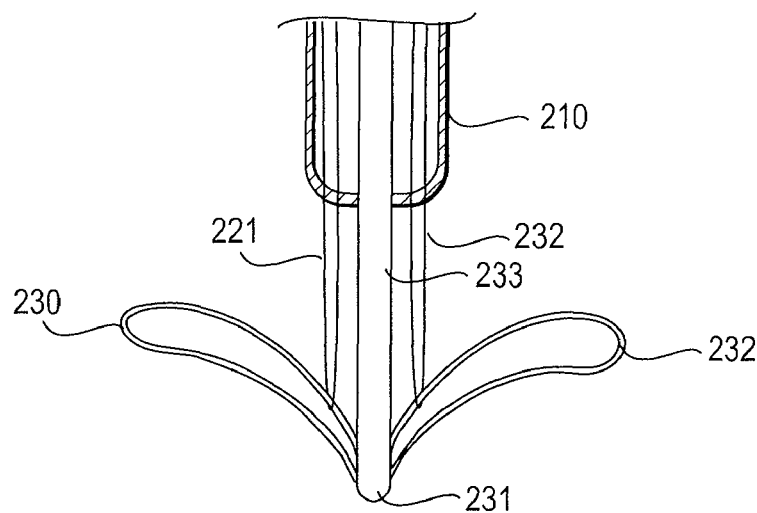

In some embodiments, the distal elements are held in a retracted position under tension and are extendable upon release. For example, FIGS. 16A-16C illustrate one embodiment of the interventional tool 204 in various states of deployment. The elements 230, 232 are disposed near a distal end 231 of an inner shaft 233 within the shaft 210. FIG. 16A shows the elements 230, 232 in a retracted position as they are held under tension by loops 221, each loop 221 threaded through an element 230, 232 and pulled upwardly within the shaft 210 as shown. The loops 221 may be comprised of any suitable material, including suture, wire or polymer strands. It may be appreciated that the tool 204 may be introduced in this state or the inner shaft 233 and elements 230, 232 may be retracted within the shaft 210 and later deployed to this state when near the valve. FIG. 16B shows the elements 230, 232 in an extended state of deployment. Here, the upward force on the loops 221 have been relaxed and the tension released. Consequently, the elements 230, 232 extend outwardly as shown and the relaxed loops 221 hang at any location. As shown in FIG. 16C, the loops 221 may then be slid to toward the inner shaft 233 so that the elements 230, 232 may more easily engage the valve leaflets LF.

Figure 16D:
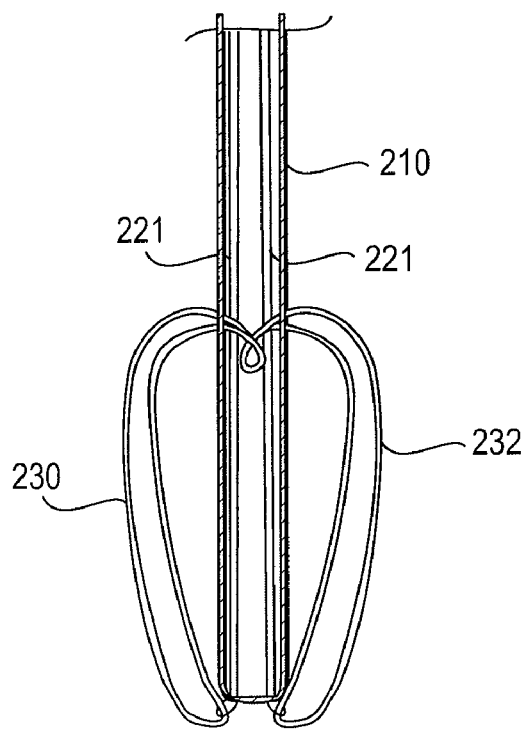
Figure 16E:
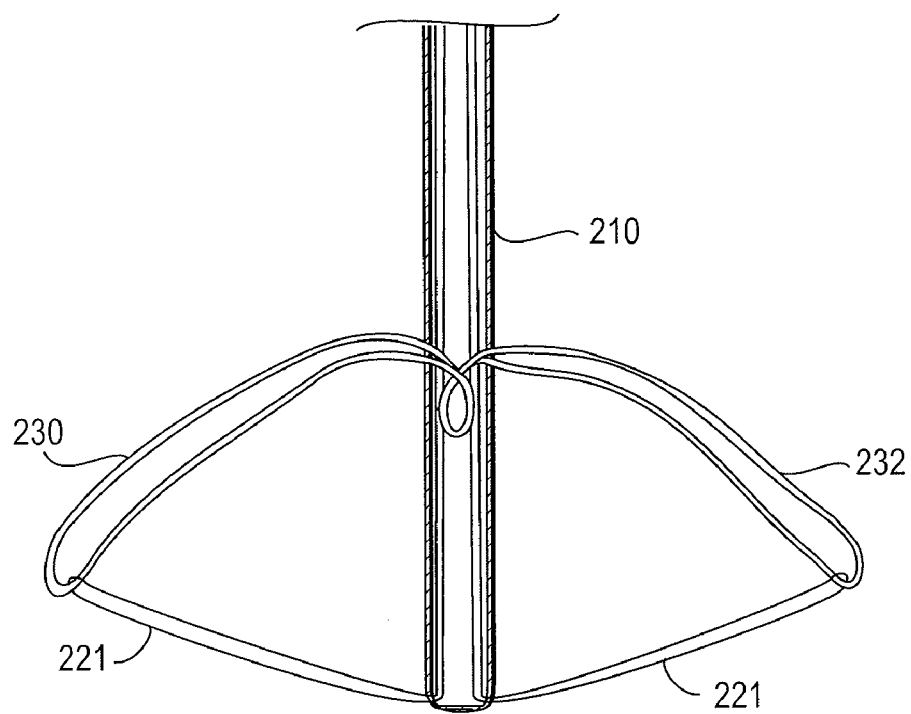

FIGS. 16D-16E illustrate another embodiment wherein the distal elements are held in a retracted position under tension and are extendable upon release. Here, the elements 230, 232 are disposed near the distal end the shaft 210. FIG. 16D shows the elements 230, 232 in a retracted position as they are held downward against the shaft 210 under tension by loops 221, each loop 221 threaded through an element 230, 232 and pulled upwardly within the shaft 210 as shown. The loops 221 may be comprised of any suitable material, including suture, wire or polymer strands. FIG. 16E shows the elements 230, 232 in an extended state of deployment. Here, the upward force on the loops 221 have been relaxed and the tension released. Consequently, the elements 230, 232 extend upwardly and outwardly as shown and the relaxed loops 221 are drawn upward to hang from the extended elements 230, 232.

Figure 16F:
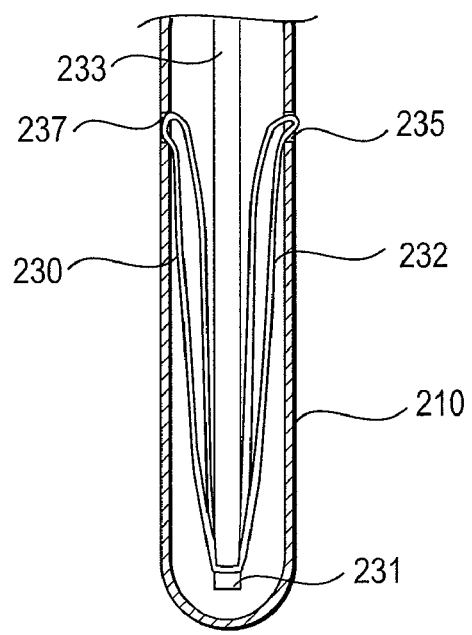
FIGS. 16F-16G illustrate an embodiment of the capture device wherein the distal elements extend and retract together.
Figure 16G:
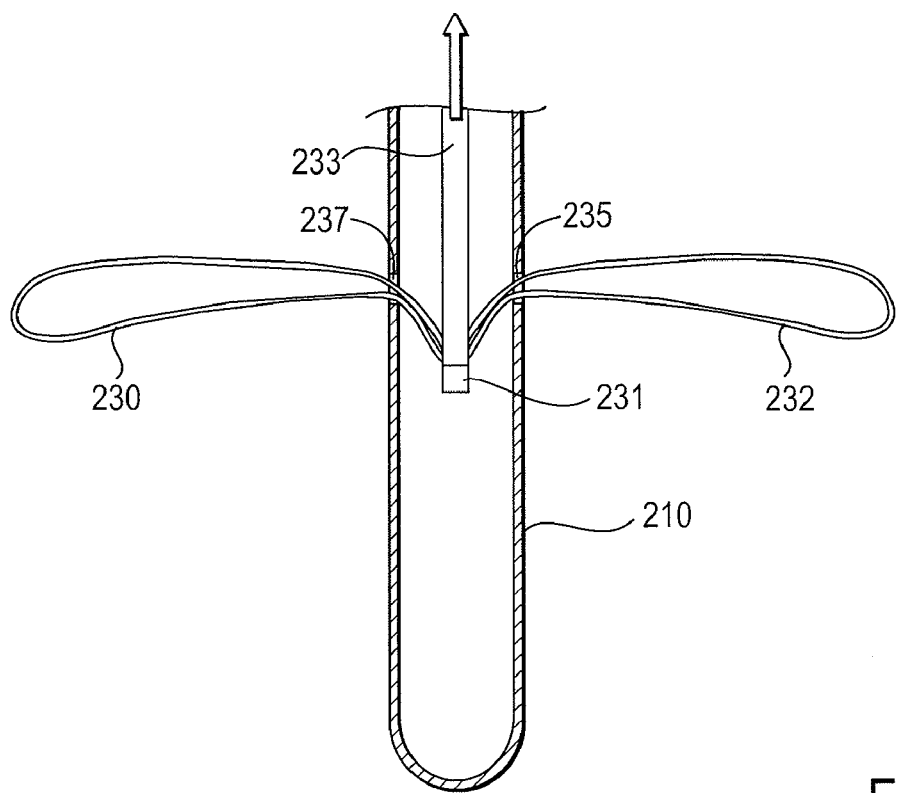

In some embodiments, the distal elements extend and retract together, an example of which is illustrated in FIGS. 16F-16G. Referring to FIG. 16A, the elements 230, 232 are disposed at the distal end 231 of the inner shaft 233 within the shaft 210. The elements 230, 232 pass through the shaft 210 wall and outside the shaft 210 at locations 235, 237 desired for element protrusion. Upon retracting the inner shaft 233, as shown in FIG. 16B, the elements 230, 232 together are guided radially outward through the shaft 210 at the locations 235, 237. It may be appreciated that although the elements 230, 232 in FIGS. 16A-16G have been illustrated as curving downwardly, towards the distal end, the elements may alternatively be uncurved, curve upwardly, include compound curvatures or more than one curvature along each element, or any other combination of curvatures.

Figure 17A:
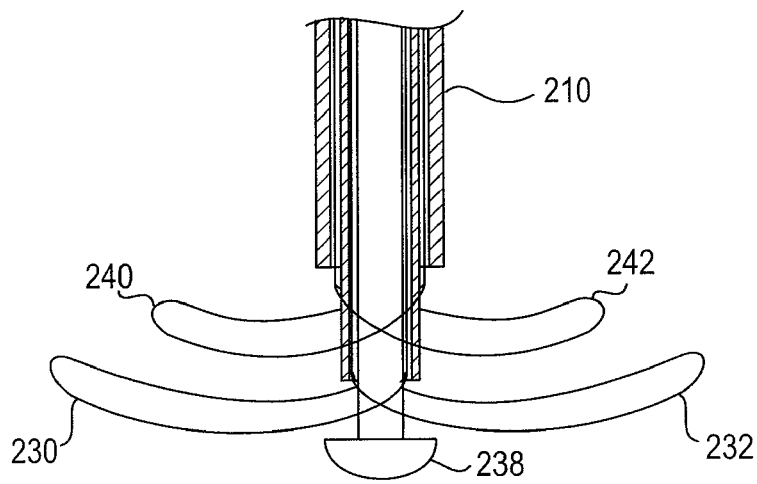
FIGS. 17A-17D show a number of embodiments of the interventional tool comprising proximal elements which are capable of protruding outward from the shaft at a location proximal to the distal elements.
Figure 17B:
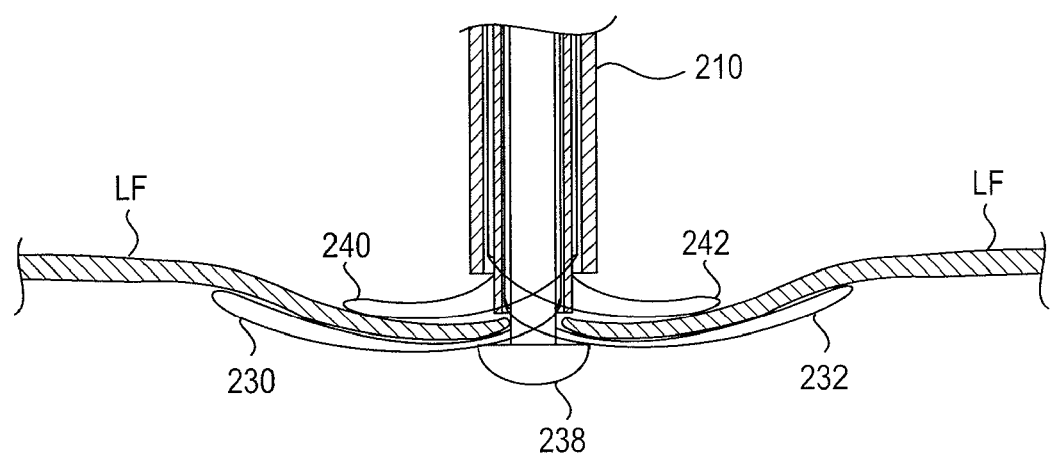

In a number of embodiments, an example of which is shown in FIGS. 17A-17D, the interventional tool 204 also comprises proximal elements 240, 242 which are capable of protruding radially outward from the shaft at a location which is proximal to the elements 230, 232 previously described. The proximal elements 240, 242 may have any of the forms, shapes, material compositions, features, or capabilities described in relation to the distal elements 230, 232. In FIG. 17A, such proximal elements 240, 242 are shown as loops. Such proximal elements 240, 242 would most commonly be used in embodiments of capture devices 204 designed for an antegrade approach to the valve wherein the device 204 crosses the valve to access the ventricular surface of the leaflets. Typically, once the distal elements 230, 232 are extended and positioned against the ventricular surface of the leaflets, the proximal elements 240, 242 are then extended and positioned against the artrial surface of the leaflets. As shown in FIG. 17B, the leaflets LF are thus secured between the proximal elements 240, 242 and distal elements 230, 232. The proximal elements 240, 242 and/or distal elements 230, 232 may then be extended, retracted or similarly adjusted to further orient the leaflets. In addition, the cap 238 may optionally be retracted toward the shaft 210 to further pinch the leaflets between the elements.

Figure 17C:
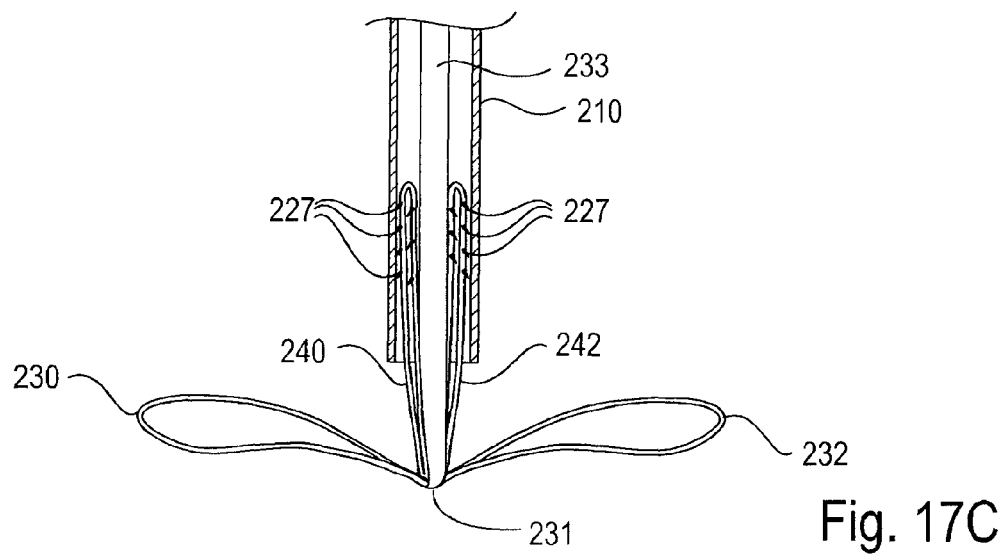
Figure 17D:
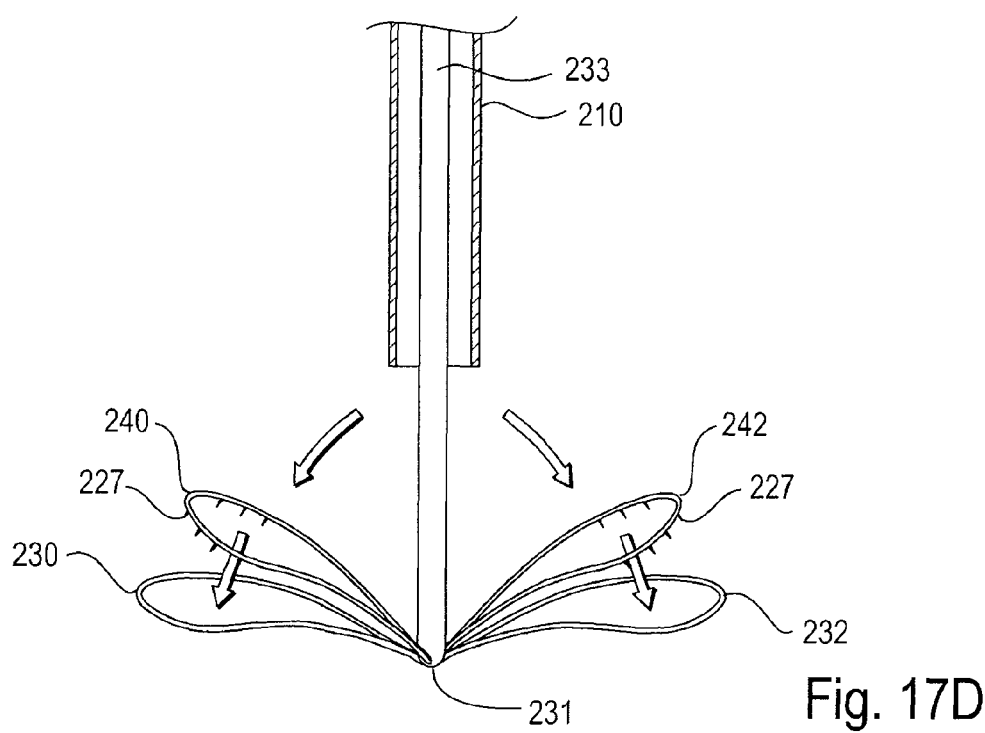

Referring to FIG. 17C, the proximal elements 240, 242 may be separately deployable from the distal elements 230, 232. Here, the elements 240, 242, 230, 232 are disposed near the distal end 231 of the inner shaft 233 within shaft 210. The proximal elements 240, 242 are constrained within the shaft 210 while the distal elements 230, 232 are extended radially outward. In this state, the distal elements 230, 232 may be positioned against the ventricular surface of the valve leaflets LF. The proximal elements 240, 242 may then be released by retracting the shaft 210. As shown in FIG. 17D, release of the proximal elements 240, 242 allows them to extend radially outward and downward, as illustrated by arrows. Depending on the curvature of the proximal elements 240, 242, they may remain proximal to, move to within the same plane of, or move beyond the plane of the distal elements 230, 232. In addition, the proximal elements may include various friction accessories 227, such as prongs, to assist in holding the valve leaflets LF. Other friction accessories 227 include windings around the elements, such as metal, polymer or suture windings, cuffs, bands, or barbs. Further, such accessories 227 may additionally or alternatively be included on the distal elements 230, 232. Likewise, such accessories 227 may be included on the elements of the capture devices in any of the embodiments of the interventional tool. In an additional embodiment, depicted in FIGS. 18A-18D, the valve leaflets LF may be pinched between a proximal element or superior loop 720 and a distal element or inferior loop 721. In a preferred embodiment, the capture device or grasper is comprised of a nitinol flat ribbon heat set in the shape of double loops 720, 721. The ribbon may be mounted on a series of three coaxial shafts, an interior shaft 725, a central shaft 726 and an exterior shaft 727. The distal end of the ribbon may be attached to the distal end 730 of the interior shaft 725, a midportion of the ribbon may be attached to the distal end 731 of the central shaft 726, and the proximal end of the ribbon may be attached to the distal end 732 of the exterior shaft 727. One or more ribbons may be mounted on the coaxial shafts; in this example, two ribbons are shown 180 degrees apart. When extended, as shown in FIG. 18A, the grasper may be pulled flat against the shafts 725, 726, 727 for ease of insertion through a guide catheter or tool and into a desired position between the valve leaflets LF. When the central shaft 726 is retracted or the exterior shaft 727 advanced, as shown in FIG. 18B, the superior loops 720 may extend radially from the shafts. The superior loops 720 may rest on the superior surface of the valve leaflets LF in the atrium, as shown in FIG. 18D. In this position, the superior loops 720 may aid in orientation assessment, as the superior loops may be echo or fluorogenic and may be easily visible in relation to the cardiac structures or other devices or components. When positioned in a desired location, the interior shaft 725 may then be retracted, as shown in FIG. 18C, to extend the inferior loops 721 radially from the shafts. The inferior loops 721 may be in contact with the inferior surface of the valve leaflets LF in the ventricle. Thus, the valve leaflets LF may be pinched between the inferior loop 721 and superior loop 720. It may also be appreciated that the inferior loops 721 may be deployed prior to the superior loops 720.

Figure 19A:
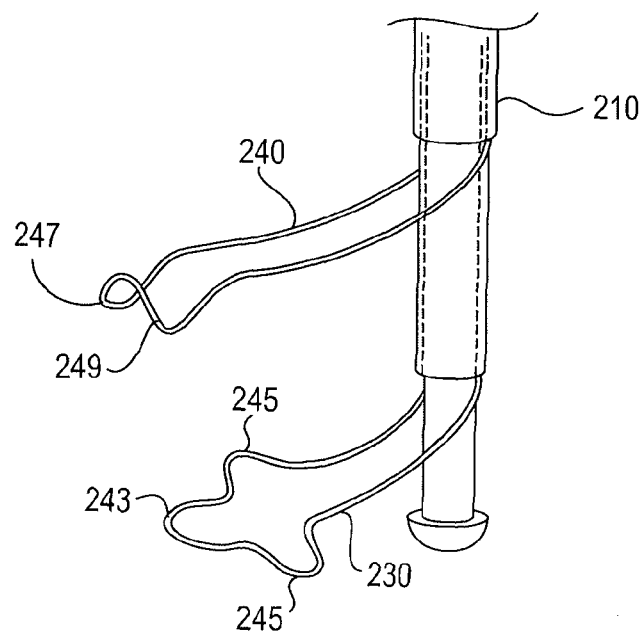
FIGS. 19A-19B are perspective views of a capture device wherein the proximal elements and the distal elements are interlockable.
Figure 19B:
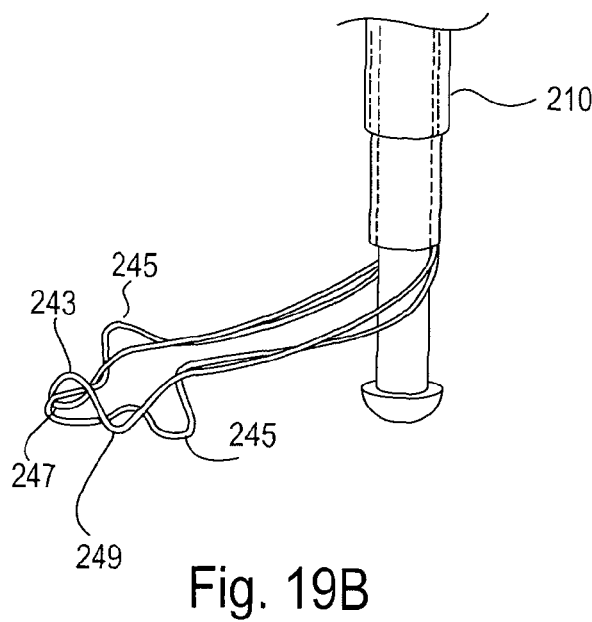
Figure 19C:
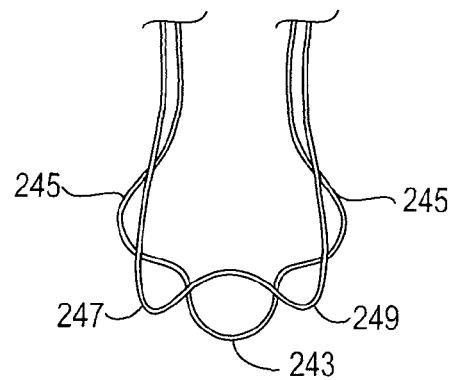
FIG. 19C illustrates a top view showing the interlocked elements.

Further, the proximal elements 240, 242 and distal elements 230, 232 may interlock to prevent relative motion between the elements and more securely hold the leaflets LF. Referring to FIG. 19A, a distal element 230 is shown protruding radially outwardly from the shaft 210. In this example, the distal element 230 is shaped having a raised upwardly pointing tip portion 243 and two side portions 245. The proximal element 240 is shown protruding radially outwardly from the shaft 210 at a location proximal to the distal element 230. Here, the proximal element 240 is shaped having two downwardly pointing tip portions 247, 249. When the elements 230, 240 are drawn together, as shown in FIG. 19B, the raised upwardly pointing tip portion 243 fits between the two downwardly pointing tip portions 247, 249 locking the elements 230, 240 together. This may be more easily visualized in a top view of the interlocked elements 230, 240 shown in FIG. 19C. It may be appreciated that, in use, the distal element 230 is extended and positioned against a ventricular surface of a leaflet, the proximal element 240 is extended and positioned against an artrial surface of the leaflet. Thus, the leaflet is thus secured between the elements 230, 240 in the interlocked orientation.

Figure 20A:
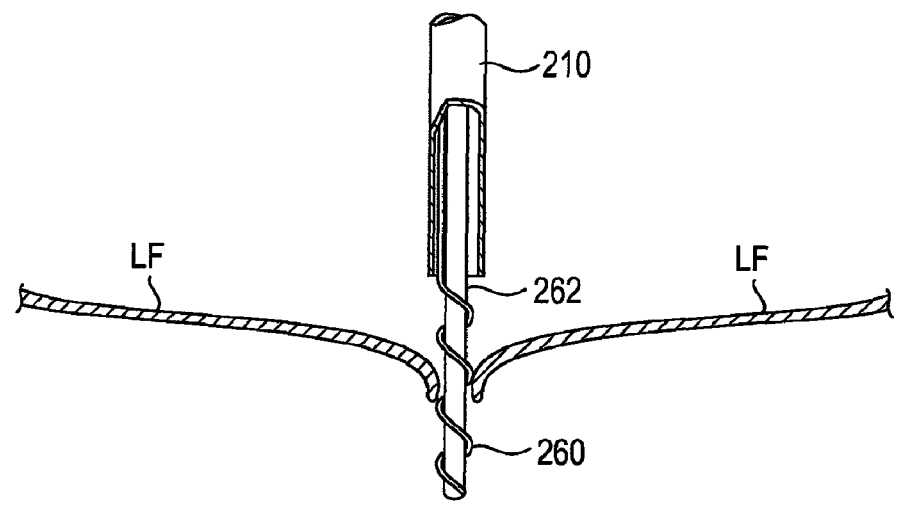
FIGS. 20A-20B illustrate an embodiment of the capture device wherein the proximal and distal elements are formed by a continuous structure.
Figure 20B:
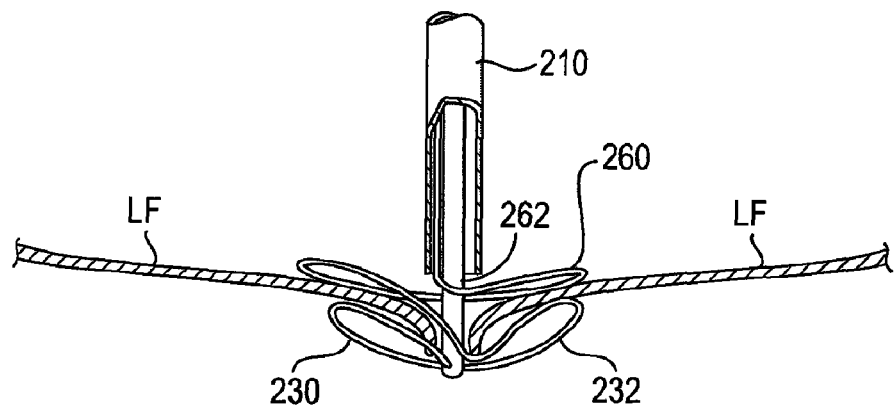

In some embodiments, the proximal and distal elements are formed by a continuous structure. Referring to FIG. 20A, the continuous structure 260 is shown in a low profile position wrapped around the end portion 262 of the shaft 210 of the interventional catheter 200 under tension. In this profile position, the catheter 202 is advanced with an atrial approach through the valve, between the leaflets LF, so that the distal end 202 extends beyond the valve into the ventricle. Referring to FIG. 20B, the continuous structure 260 is then released and allowed to relax. Prior heat forming allows the structure 260 protrude radially outward at various points along the structure 260. Each protrusion is similar to an above described proximal or distal element and functions in a similar manner. The embodiment shown in FIGS. 20A-20B includes protrusions similar to both proximal elements 240, 242 and distal elements 230, 232 as shown. These elements may protrude various distances and at various angles from the shaft, as previously described.

Many features of the distal elements 230, 232 and proximal elements 240, 242 have been described and illustrated with embodiments comprising wire loops. It may be appreciated that the described features are applicable to any of the above described embodiments, such as blocks, rods, ribbons, etc. Use of wire loops as examples are not intended to limit the scope of the present invention.

Figure 21A:
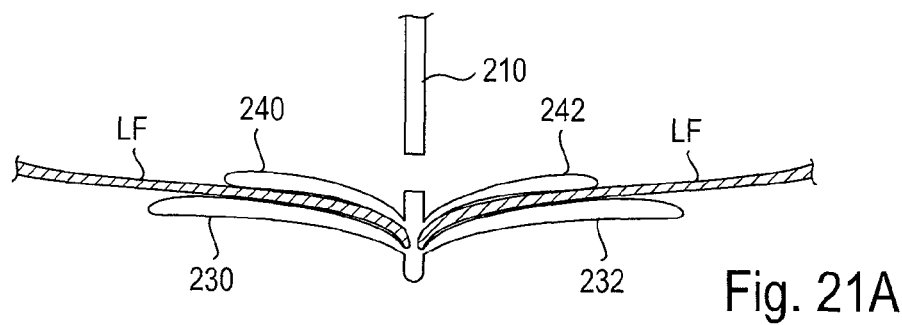
FIG. 21A illustrates leaflets captured by a capture device detached from the shaft and left behind as a fixation device.
Figure 21B:
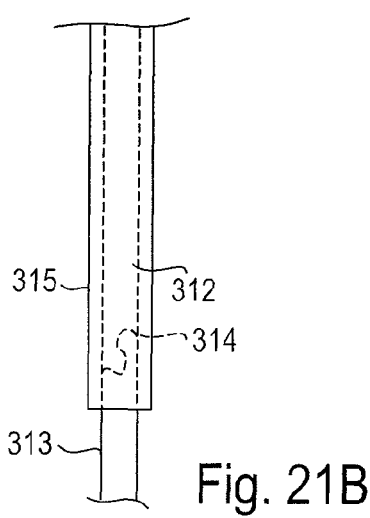
Figure 21C:
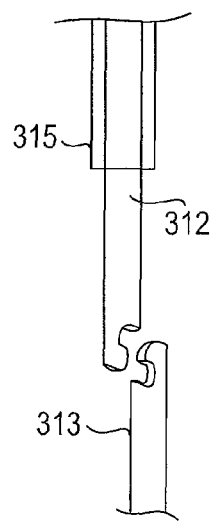
Figure 21D:
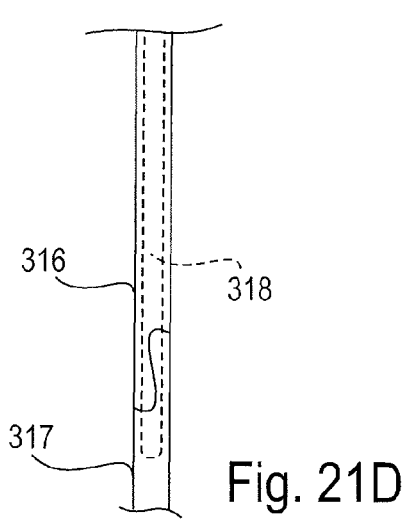
Figure 21E:
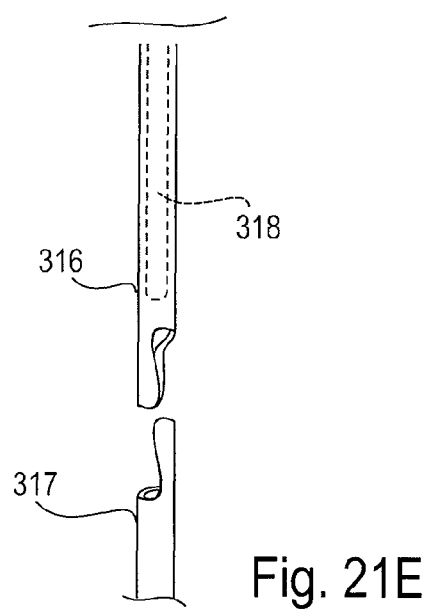

IV. LEAFLET FIXATION TOOL. With the valve leaflets grasped in a desired orientation using an embodiment of the capture device described above, the leaflets may be fixed together to maintain this orientation. This may be achieved by leaving the capture device in place to function as a fixation device. To this end, the capture device may be detachable from the interventional tool to be left behind as a permanent or temporary implant. FIG. 21A illustrates a capture device comprising distal elements 230, 232 and proximal elements 240, 242 wherein the leaflets LF are captured therebetween. As shown, the capture device may be detached from the shaft 210 and left behind as a fixation device. Detachment may be achieved by a variety of different mechanism and design features. FIGS. 21B-21H illustrate embodiments of such detachment mechanisms. FIG. 21B shows an upper shaft 312 and a detachable lower shaft 313 which are interlocked at a joining line 314. The joining line 314 may have any shape or curvature which will allow or facilitate interlocking and later detachment. A snuggly fitting outer sheath 315 is positioned over the shafts 312, 313 to cover the joining line 314 as shown. FIG. 21C illustrates detachment of the lower shaft 313 from the upper shaft 312. This is achieved by retracting the outer sheath 315, so that the joining line 314 is exposed, which allows the shafts 312, 313 to separate. Similarly, FIG. 21D illustrates a tubular upper shaft 316 and a detachable tubular lower shaft 317 which are interlocked at a joining line 314. Again, the joining line 314 may have any shape or curvature which will allow or facilitate interlocking and later detachment. A snuggly fitting rod 318 is inserted through the tubular shafts 316, 317 to bridge the joining line 314 as shown. FIG. 21E illustrates detachment of the lower shaft 317 from the upper shaft 316. This is achieved by retracting the rod 318 to a position above the joining line 314 which in turn allows the shafts 316, 317 to separate.

FIGS. 21F-21H illustrate another embodiment of a detachment mechanism. Referring to FIG. 21F, an upper shaft 900 is shown attached to a detachable lower shaft 902. An outer tube 910 surrounds the upper shaft 900 and contacts the lower shaft 902 as shown. The upper shaft 900 is held in attachment to the lower shaft 902 by the presence of a ball 904 or similar device which is disposed in recess 906, shaped to receive a portion of the ball 904, in the lower shaft 902. The ball 904 is held in the recess 906 by an angular cutout 908 in the upper shaft 900. Referring to FIG. 21G, the upper shaft 900 may be retracted. This may be achieved by pulling the upper shaft 900 upwards within the outer tube 910 while the outer tube 910 applies force on the lower shaft 902 to aid separation. As the upper shaft 900 is retracted, the angular cutout 908 allows the ball 904 to move from the recess 906 to a position within the upper shaft 900. Referring to FIG. 21H, upper shaft 900 and ball 904 may retracted into the outer tube 910, completing the detachment from the lower shaft 902. It may be appreciated that this detachment mechanism concept may be used with other shaped shafts, recesses, and balls or similar devices and may function without the use of the outer tube.

Figure 21I:
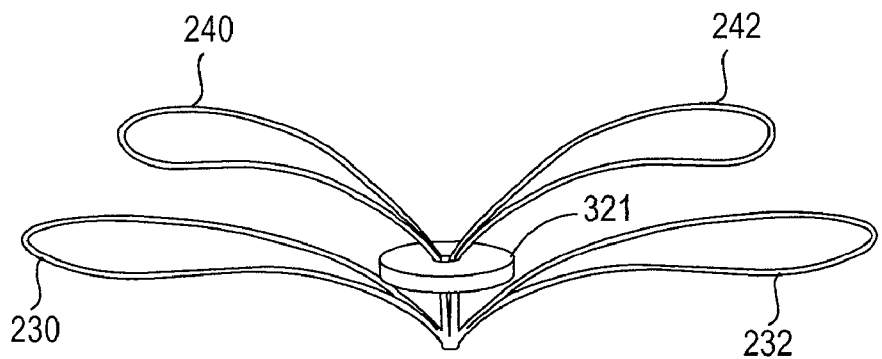
FIGS. 21I-21J illustrate the use of capture devices having a pledget for use as a fixation device.
Figure 21J:
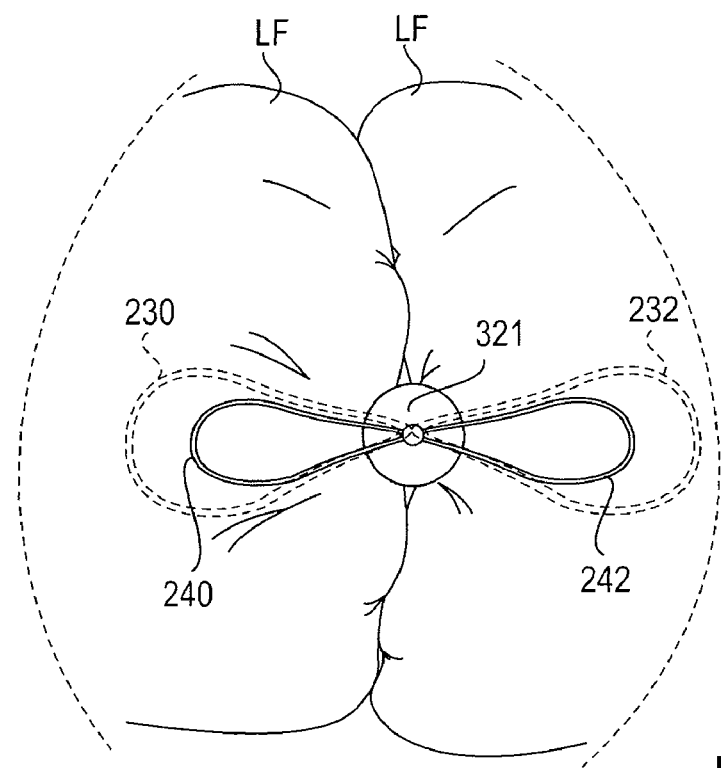

In some cases, use of the capture device as a fixation device may create one or more small gaps between the leaflets LF at the coaptation line. If this is likely to occur, or as an added precaution, a block, disk or pledget 321 of material may be positioned such that it blocks possible flow through such a gap. As shown in FIG. 21I, the pledget 321 may be positioned between the proximal elements 240, 242 and distal elements 230, 232. When the leaflets LF are captured between the proximal elements 240, 242 and distal elements 230, 232, as shown in a top view in FIG. 21J, the pledget 321 is positioned between the leaflet LF edges to block flow therethrough.

Alternatively, fixation may be accomplished with the use of separate devices used in combination with an interventional tool having a capture device. And, many embodiments of the present invention incorporate a fixation tool into the interventional tool for such use. The fixation tools described herein below may be used with any of the capture devices previously described. A few examples will be presented to illustrate possible embodiments.

Figure 22:
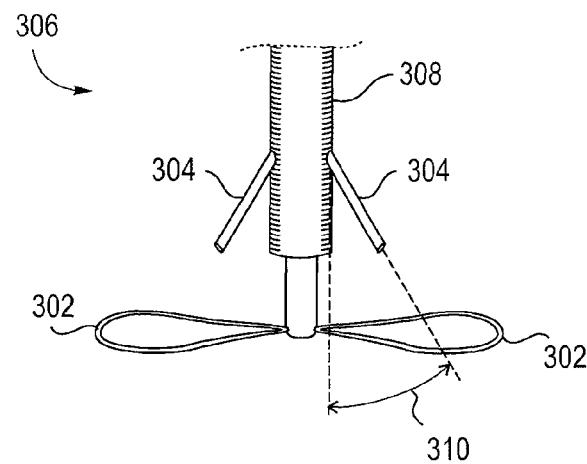
FIG. 22 illustrates an embodiment of the interventional tool having distal elements and guide conduits disposed near its distal end.

In many embodiments, such as illustrated in FIG. 22, the interventional tool 100 has distal elements 302 and guide conduits 304 disposed near its distal end 306. Guide conduits 304 such as these may be used to guide a number of tools or devices to specific locations near the distal end 306. For example, in this case, the guide conduits 304 are used to guide fixation tools to specific locations on the surfaces of the leaflets. In addition, as will be described in a later section, the conduits 304 may be attached to the proximal loops. In addition to other benefits described later, the conduits 304 may provide added support or rigidity to the interventional tool which may aid in the fixation process.

Figure 23A:
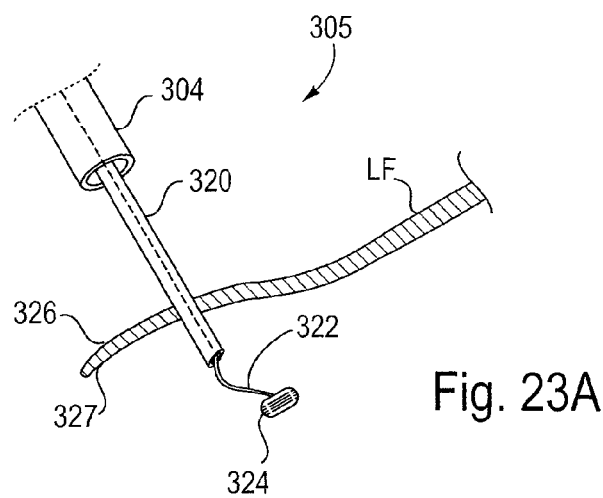
FIGS. 23A-23B illustrates the placement of a suture having an anchor with the use of a penetrating device advanced through a guide conduit.
Figure 23B:
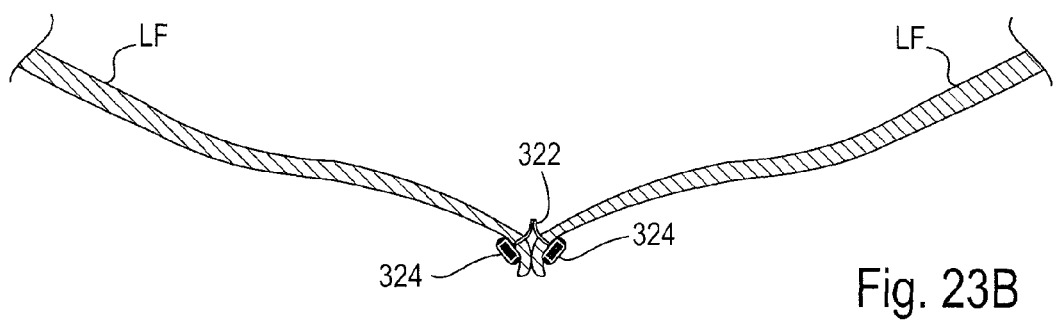

As shown in FIG. 22, the guide conduits 304 are located proximal to the distal elements 302 and are capable of extending angularly outward from the shaft 308. It may be appreciated that the conduits 304 may be located at any point along the shaft 308 and may be capable of extending at any angle 310. Typically, such an angle 310 ranges from approximately 90 degrees, perpendicular to the shaft, to around zero degrees, essentially parallel to the shaft. Any angle 310 may be used to target the leaflets LF at points which are approximately 1-12 mm, preferably 3-5 mm, inward from the free edge FE of each leaflet LF. In a particular embodiment of the interventional tool 100, the guide conduit 304 is used for fixation. Here, the guide conduit 304 is used to introduce a fixation tool 305 comprising a penetrating device or needle 320 housing a suture 322 having an anchor 324 disposed at the distal end of the suture 322. The needle 320 is advanced toward a valve leaflet, either by extension of the guide conduit 304 or the needle 320 itself. In either case, the needle 320 is then advanced to penetrate the leaflet and emerge from the other side or the distal side of the leaflet. The needle 320 may be rigid, possibly made from a metallic material, or flexible, made from a flexible polymer, for example. As shown in FIG. 23A, an atrial approach would involve the needle 320 penetrating the atrial surface 326 of the leaflet LF, passing through the leaflet LF and emerging on the ventricular surface 327 of the leaflet LF. Once emerged, the anchor 324 is deployed as shown. The anchor 324 may be deployed by passing the anchor 324 through the needle 320 and expanding or allowing it to self-expand after it has exited the needle 320. Alternatively, the anchor 324 may be mounted on the outside of the needle 320 and covered by a sheath. Retraction or removal of the sheath would allow expansion of the anchor 324. In any case, after anchor deployment, the needle 320 is then retracted while maintaining the anchor 324 on the distal side of the leaflet LF. Consequently, the attached suture 322 remains in place, passing through the leaflet penetration. Once each fixation tool 305 has deployed its anchor 324 on the distal side of a leaflet LF, individually or simultaneously, the guide conduit 304 and interventional tool 204 are retracted. As shown in FIG. 23B, the ends of the sutures 322 may then be fixed together by conventional knot tying or any suitable method, including positioning fasteners. This may be achieved with the use of additional tools which are part of the interventional catheter 200, or this may be achieved by other methods after withdrawal and removal of the interventional catheter 200.

Figure 24:
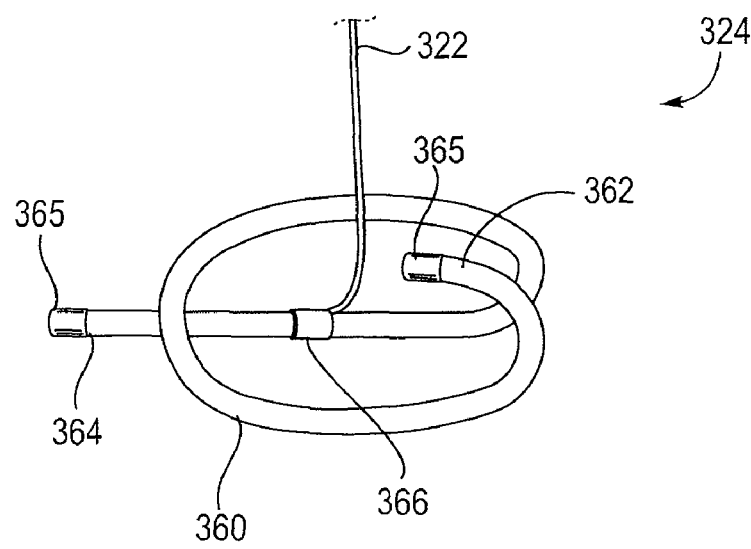
FIGS. 24, 25, 26A-26B, 27A-27N, 27P-27R, and 27T illustrate various embodiments of anchors.
Figure 25:
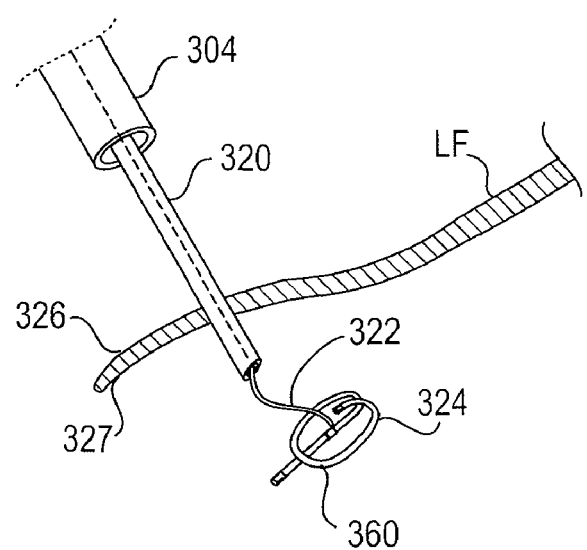

A number of different types of anchors 324 may be used during fixation of the leaflets. Typically, the anchor 324 is expandable from a compressed low profile state, for delivery to the anchoring site, to an expanded state to provide a large enough surface for anchoring support. One embodiment of the anchor 324, shown in FIG. 24, is comprised of a wire 360 curved into a ring shape. The wire 360 may be stainless steel, nitinol or other shape memory wire, polymer or similar material. Suture 322 is attached to the center 366 of the ring by a bonding material. The wire 360 has a first end 362 and a second end 364 wherein the first end 362 is disposed on top of the ring and the second end 364 is disposed underneath the ring as shown. This configuration provides support for the ring when the anchor 324 is pulled snuggly against a valve leaflet surface by the suture 322. In addition, the first end 362 and second end 364 may have radiopaque markers 365 disposed thereon. Referring to FIG. 25, this embodiment of the anchor 324 is shown in possible use for fixation of valve leaflets. As described previously, an atrial approach would involve the needle 320 penetrating the atrial surface 326 of the leaflet LF, passing through the leaflet LF and emerging on the ventricular surface 327 of the leaflet LF. When the anchor wire 360 is comprised of flexible materials, the anchor 324 is collapsible for loading within the needle 320. Once the needle 320 has emerged on the ventricular surface 327, the anchor 324 is deployed as shown. The needle 320 is then retracted while maintaining the anchor 324 on the distal side of the leaflet LF. Consequently, the attached suture 322 remains in place, passing through the leaflet penetration. Once each fixation tool 305 has deployed its anchor 324 on the distal side of a leaflet LF, individually or simultaneously, the guide conduit 304 and interventional tool 204 are retracted. The sutures 322 may be pulled tight so that the anchors 324 are disposed against the leaflets LF and the ends of the sutures 322 may then be fixed together by conventional knot tying or any suitable method, including positioning fasteners.

Figure 26A:
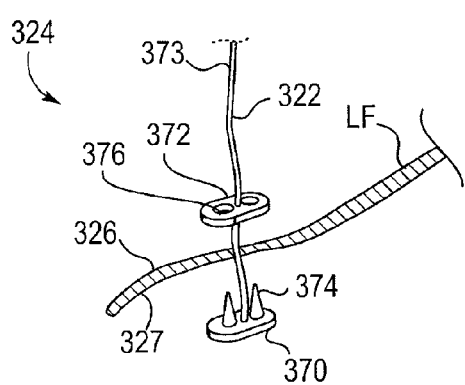
Figure 26B:
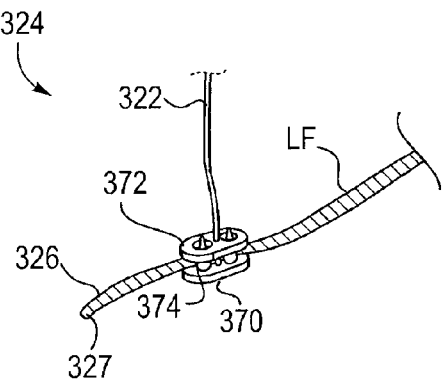

Another embodiment of the anchor 324, shown in FIGS. 26A-26B, involves two parts which are disposed on opposite sides of a valve leaflet. Referring to FIG. 26A, the anchor 324 is comprised of a first part 370 and a second part 372 wherein the suture 322 is fixedly attached to the first part 370, slidably attached to the second part 372, and continues to a free end 373 proximal to the second part 372. In addition, the first part 370 may have spikes 374 or other protrusions which interlock with receptacles 376 in the second part 372. It may be appreciated that such spikes 374 may be located on the second part 372 to interlock with receptacles 376 on the first part 370 or such spikes 374 and receptacles 376 may be located on both parts 370, 372. The anchor 324 may be comprised of flexible materials so that the anchor 324 is collapsible for loading within the needle 320. In this case, as previously described, the needle may penetrate the atrial surface 326 of the leaflet LF, pass through the leaflet LF and emerge on the ventricular surface 327 of the leaflet LF. Here the first part 370 of the anchor 324 is deployed, as shown in FIG. 26A. The needle 320 is then retracted while maintaining the first part 370 on the distal side of the leaflet LF. Consequently, the attached suture 322 remains in place, passing through the leaflet. Once the needle 320 is disengaged from the leaflet LF, the second part 372 of the anchor is deployed so the second part 372 is disposed on the atrial surface 326 as shown. Referring to FIG. 26B, the parts 370, 372 may then be drawn together so the spikes 374 pass through the leaflet LF and are received in the receptacles 376 locking the anchor in place. One or more sutures 322 with anchors 324 may be placed in other locations on the same or other leaflets LF. The ends of the sutures 322 may then be fixed together by conventional knot tying or any suitable method, including positioning fasteners.

Figure 27A:
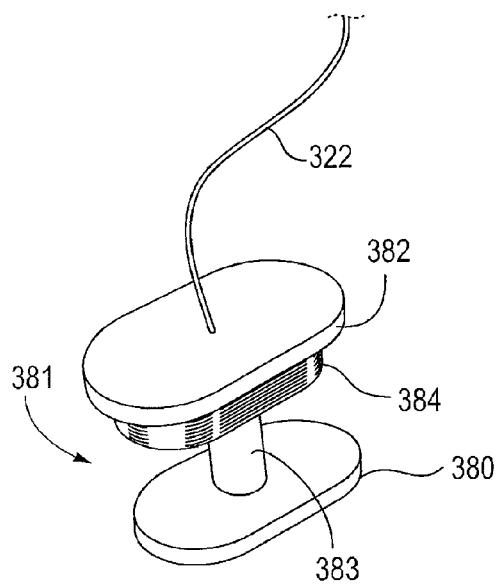
Figure 27B:
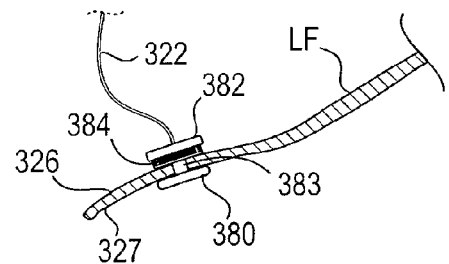
FIGS. 27O and 27S not used.
FIGS. 27U-27V illustrate anchors deployed from a doubled barreled delivery device.

Another embodiment of the anchor 324, shown in FIGS. 27A-27B, involves a single structure having flanges which are disposed on opposite sides of a valve leaflet. Referring to FIG. 27A, the anchor 324 is comprised of a structure 381 having a first flange 380, a second flange 382 and a cylindrical portion 383 therebetween. The suture 322 is fixedly attached to the structure 381 as shown. In addition, the structure 381 may optionally include a compressible layer 384 on a surface of either the first flange 380, the second flange 382 or both facing the cylindrical portion 383. The anchor 324 may be comprised of flexible materials so that the anchor 324 is collapsible for loading within the needle 320. In this case, as previously described, the needle may penetrate the atrial surface 326 of the leaflet LF, pass through the leaflet LF and emerge on the ventricular surface 327 of the leaflet LF. Here the structure 381 is partially deployed so that the first flange 380 emerges and is positionable against the ventricular surface 327. The needle 320 is then retracted while maintaining the first flange 380 on the distal side of the leaflet LF. Consequently, cylindrical portion 383 emerges and is positioned through the leaflet. As the needle 320 is disengages from the leaflet LF, the second flange 382 is deployed so the second flange 382 is disposed on the atrial surface 326 as shown in FIG. 27B. One or more sutures 322 with anchors 324 may be placed in other locations on the same or other leaflets LF. The ends of the sutures 322 may then be fixed together by conventional knot tying or any suitable method, including positioning fasteners.

Figure 27C:
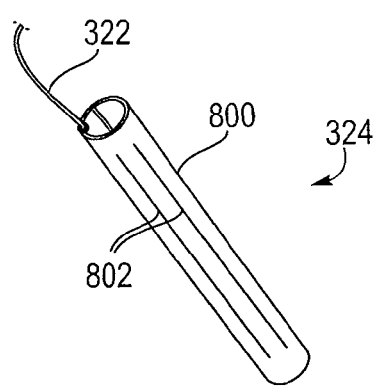
Figure 27D:
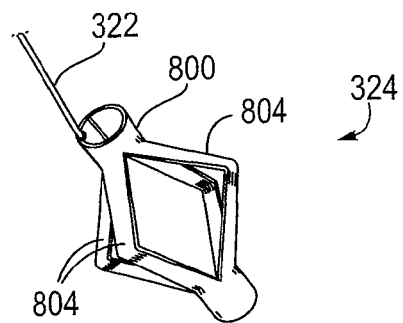
Figure 27E:
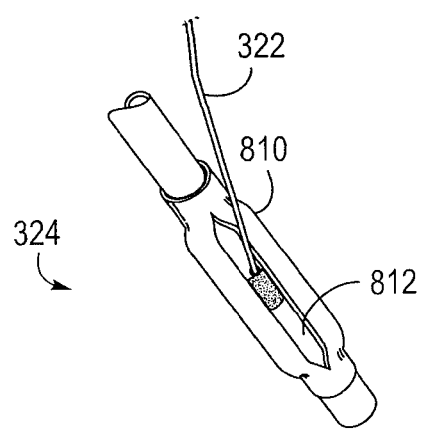
Figure 27F:
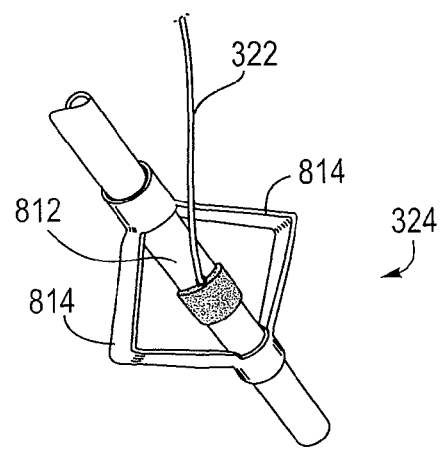
Figure 27G:
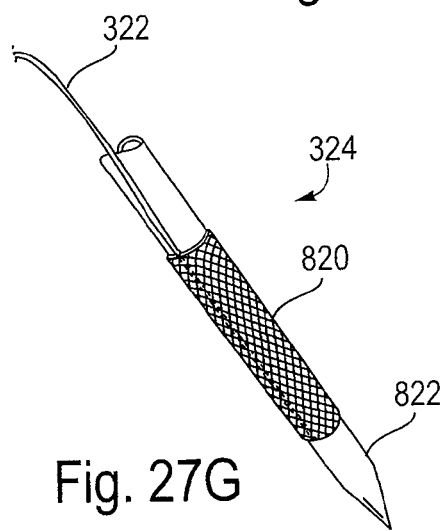

Another embodiment of the anchor 324, shown in FIGS. 27C-27D, involves a single tubular structure 800 having longitudinal slits 802 attached to the end of the suture 322. As shown in FIG. 27C, the structure 800 may be compressed to a low profile position so that it can be loaded within or on the outside of a catheter, needle or other delivery device. Upon delivery, as shown in FIG. 27D, the structure 800 may expand so that side-arms 804 project radially outward. This provides a broad surface to rest against the leaflets. A similar embodiment, shown in FIGS. 27E-27F, comprises a tubular structure 810 having a central bar 812 to which the suture 322 is attached. As shown in FIG. 27F, the structure 810 may be compressed to a low profile position. Upon delivery, as shown in FIG. 27G, the structure 810 may expand so that side-arms 814 project radially outward. Such positioning of the suture 322 may allow the anchor 324 to be positioned more flush to the leaflets.

Figure 27H:
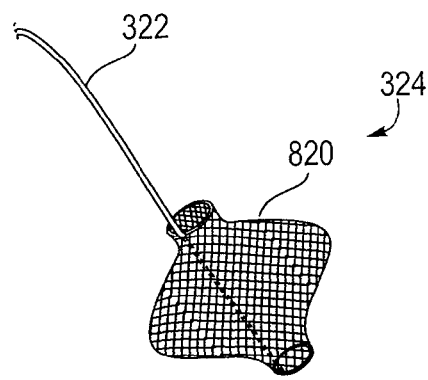

Another embodiment of the anchor 324, shown in FIGS. 27G-27H, involves a tubular structure 820 attached to the end of the suture 322. As shown in FIG. 27G, the structure 820 may be mounted on the outside of a needle or introductory device 822 in a low profile position. Upon delivery, as shown in FIG. 27H, the structure 820 may expand radially outward. To achieve this, the structure 820 may be self expanding, wherein the structure 820 is released by retracting a sheath or similar restraining support. Or, the structure 820 may be mechanically expanded by action of a balloon or similar device mounted on the introductory device. In any case, introductory device 822 may then be removed.

Figure 27I:
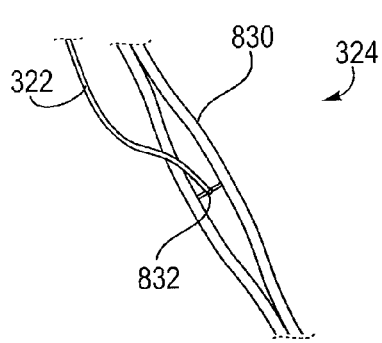
Figure 27J:
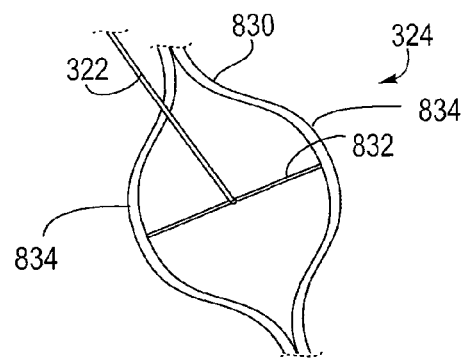

Another embodiment of the anchor 324, shown in FIGS. 27I-27J, involves a longitudinal structure 830 having a horizontal beam 832 attached to the end of the suture 322. As shown in FIG. 27I, the structure 830 may be compressed to a low profile position so that it can be loaded within a catheter, needle or other delivery device. Upon delivery, as shown in FIG. 27J, the structure 830 may expand so that side-arms 834 project radially outward. This may be achieved by expanding the horizontal beam 832 which in turn pushes the side-arms outward. Alternatively, this may be achieved by the side-arms 834 self-expanding which in turn expands the horizontal beam 832.

Figure 27K:
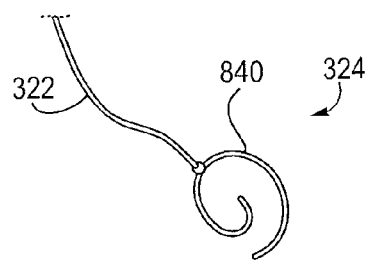
Figure 27L:
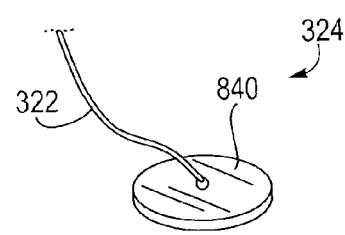

Another embodiment of the anchor 324, shown in FIGS. 27K-27L, involves a thin disk 840 attached to the end of the suture 322. As shown in FIG. 27K, the disk 840 may be rolled to a cylinder shape, for either mounting on the outside of or for insertion through a lumen in a needle, catheter or other introductory device. Upon delivery, as shown in FIG. 27L, the disk 840 may then be flattened to provide a large surface area to rest against the leaflets.

Figure 27M:
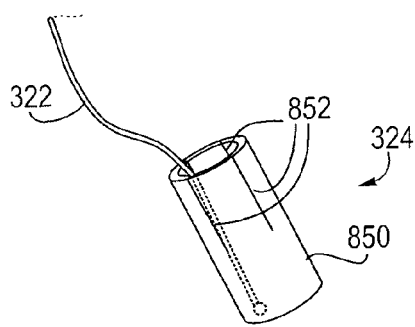
Figure 27N:
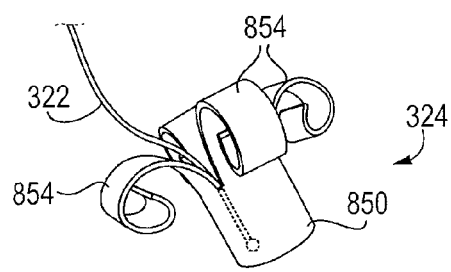

Another embodiment of the anchor 324, shown in FIGS. 27M-27N, involves a single tubular structure 850, having longitudinal slits 852 from one end to approximately midsection, attached to the end of the suture 322. As shown in FIG. 27M, the structure 850 may be compressed to a low profile position so that it can be loaded within or on the outside of a catheter, needle or other delivery device. Upon delivery, as shown in FIG. 27N, the slit structure portions 854 may curl or bend outwardly and/or downwardly. This provides a broad surface to rest against the leaflets.

Figure 27P:
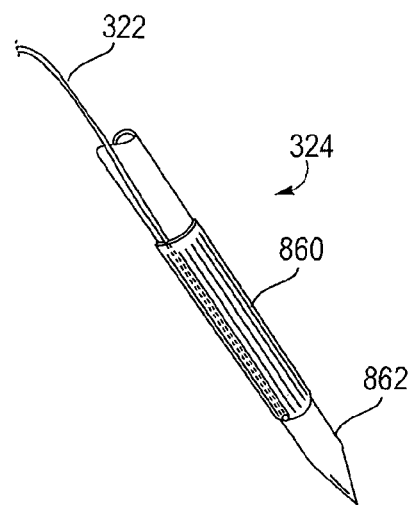
Figure 27Q:
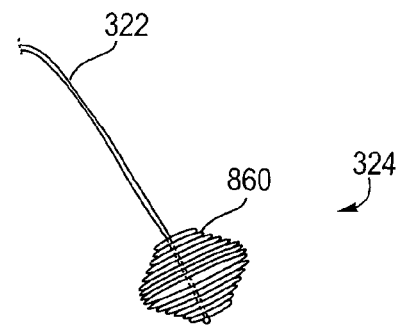

Another embodiment of the anchor 324, shown in FIGS. 27P-27Q, involves a tubular structure 860 attached to the end of the suture 322. As shown in FIG. 27P, the structure 860 may be mounted on the outside of a needle or introductory device 862 in a low profile position. Upon delivery, as shown in FIG. 27Q, the structure 860 may compress longitudinally, as in an accordion-type fashion. In doing so, the structure 860 additionally expands radially to provide added surface area to rest against the leaflets.

Figure 27R:
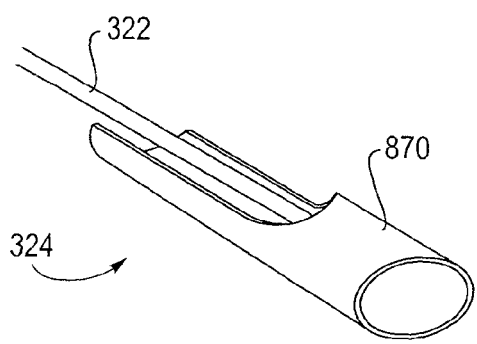
Figure 27T:
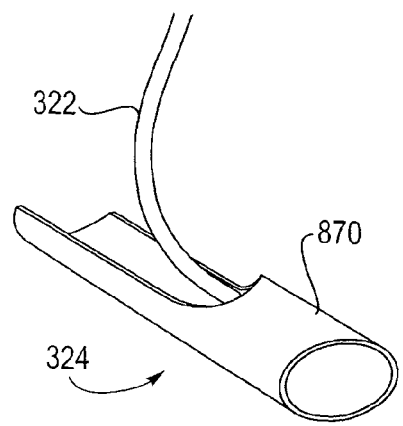
Figures 27U, 27V:
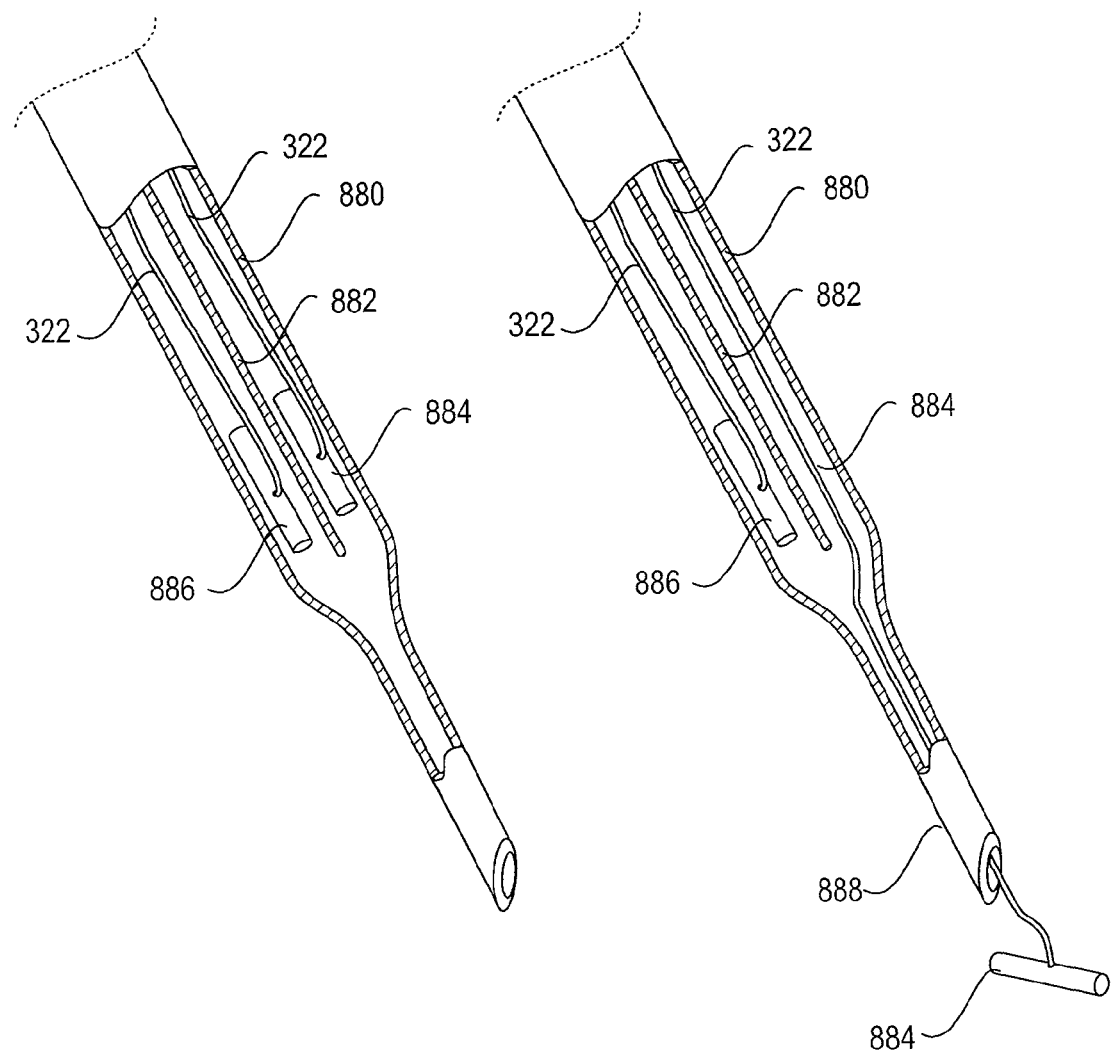

Another embodiment of the anchor 324, shown in FIGS. 27R-27T, involves a bar 870 attached to the end of the suture 322. As shown in FIG. 27R, the suture 322 may rest flush against the bar 870 in a low profile position for loading within a needle, catheter or similar delivery device. Upon delivery, as shown in FIG. 27T, the bar 870 may reposition such that it is perpendicular to the suture line 322. In this way, the bar may rest against the leaflet in an anchoring fashion. Referring to FIGS. 27U-27V, similar bars may be deployed from a double-barreled delivery device 880. As shown in FIG. 27U, a first bar 884 and a second bar 886 are loaded in parallel barrels separated by a partition 882. As shown in FIG. 27V, the first bar 884 may be deployed through the single lumen tip 888 of the delivery device 882. The device 882 may then be repositioned at another location where the second bar 886 may be deployed in a similar fashion.

Figure 28:
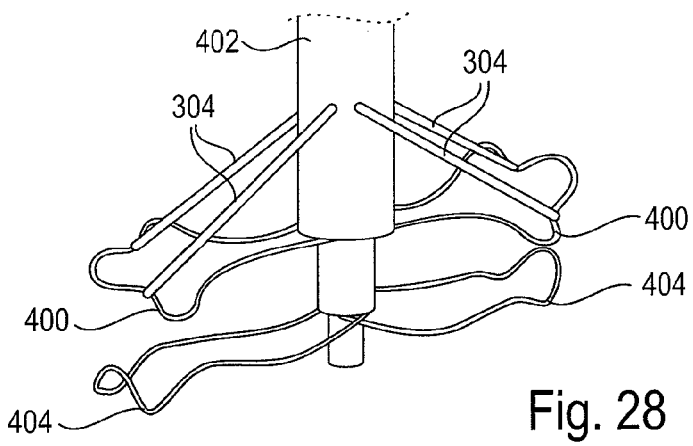
FIG. 28 depicts a perspective view of an embodiment of the interventional tool having more than one guide conduit.

In an additional embodiment of the interventional tool 100, more than one guide conduit 304 is present and directed at each leaflet for leaflet fixation. An example of such a tool 100 is shown in FIG. 28. Here the guide conduits 304 are shown attached to proximal elements 400 in a radially protruded position. Interconnection of the proximal elements 400 with the guide conduits 304 may allow one to deploy the other. For example, deployment and advancement of the guide conduits 304 angularly outward may draw the proximal elements 400 out from the shaft 402 effecting their deployment. Alternatively, the proximal elements 400 may be comprised of a material that is sufficiently rigid so that deployment of the proximal elements 400 draws the guide conduits 304 downward and outward from the shaft 402 effecting their deployment. The proximal elements 400 may also serve to position the guide conduits 304 in a desired location. Distal elements 404 are also illustrated in a radially protruded position near the distal end 406 of the tool 100.

Figure 29:
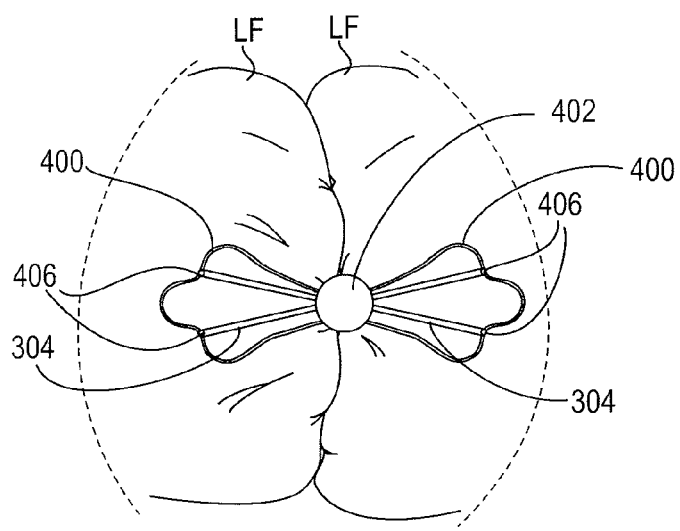
FIG. 29 depicts a top view of the interventional tool of FIG. 28 positioned between the valve leaflets.
Figure 30:
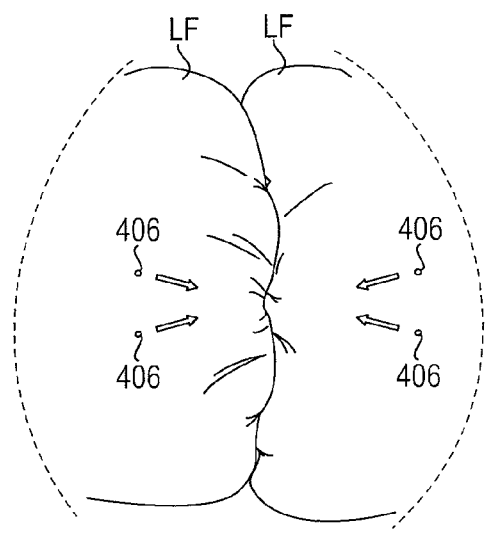
FIG. 30 illustrates target points through which sutures may be placed and drawn together in the direction of the arrows.

In use, the tool 100 is positioned between the valve leaflets LF, as shown in a top view in FIG. 29, so that the proximal elements 400 are disposed against the atrial surface (in an atrial approach) of the valve. The distal elements 404 are disposed against the ventricular surface of the valve and thus are out of view. Such placement of the proximal elements 400 provides four target points 406 on the valve leaflet LF, two target points 406 per leaflet LF. Advancement of one or more fixation tools through the guide conduits 304 allows placement of sutures and optionally anchors 324 through the leaflets LF at the target points 406 by the fixation tools. Once sutures and optionally anchors 324 are placed through each of the target points 406, the sutures may be pulled together, cinched and fastened in place. FIG. 30 illustrates such action as the target points 406 will be drawn together in the direction of the arrows. This may provide a more sturdy and effective fixation of the leaflets and therefore repair of the valve.

Sutures 233 may be placed through each of the target points 406 by a number of methods using a variety of fixation tools and devices. For example, FIG. 31 shows the placement of suture 233 through two adjacent target points 406 on one leaflet LF. Such illustrations assume an atrial approach with a top view of the atrial surface of the leaflet LF as depicted by shading. A first guide conduit 420 and a second guide conduit 422 protruding from the shaft 402 of an interventional tool 100 are shown directed toward the target points 406. Through the first guide conduit 420 a needle 423 or other device may be used to penetrate the leaflet LF and deploy a snare 424 on the ventricular side of the leaflet LF. Such a snare 424 may be comprised of any suitable material. Through the second guide conduit 422, a needle 423 or other device may be used to penetrate the leaflet LF and deploy an anchor 426 through the snare 424 on the ventricular side of the leaflet LF. Attached to the anchor 426 is a suture line 233 which passes through the penetration at the target point 406 and continues up through the second guide conduit 422. The snare 424 is then retracted back through the needle 423 pulling the anchor 426 and attached suture line 233 with it. Thus, the anchor 426 is drawn up through the first guide conduit 422 creating a continuous suture line 233 through the second guide conduit 422, across the ventricular surface of the leaflet LF and up through the first guide conduit 420. As shown in FIG. 32, this may be repeated on an adjacent leaflet LF and the suture lines 233 may be fixed together by conventional knot tying or any suitable method, including positioning fasteners. Although such fixation is shown with the sutures in a relaxed position for clarity, such fixation will typically involve cinching the leaflets together so that the target points 406 are adjacent to one another.

It may be appreciated that the methods shown in relation to FIG. 31 may be similarly performed across two adjacent leaflets LF, as illustrated in FIG. 33. Here, a needle 423 or other device may be used to penetrate a leaflet LF and deploy a snare 424 on the ventricular side of the leaflet LF. Such a snare 424 may be comprised of any suitable material. Through the second guide conduit 422, a needle 423 or other device may be used to penetrate the adjacent leaflet LF and deploy an anchor 426 through the snare 424 on the ventricular side of the leaflet LF. Again, the anchor 426 is drawn up through the first guide conduit 422 creating a continuous suture line 233 through the second guide conduit 422, across the line of coaptation C of the leaflet LF and up through the first guide conduit 420. This may be repeated on two or more additional target points 406 in a similar manner and the suture lines 233 may be fixed together by conventional knot tying or any suitable method, including positioning fasteners.

Figure 34:
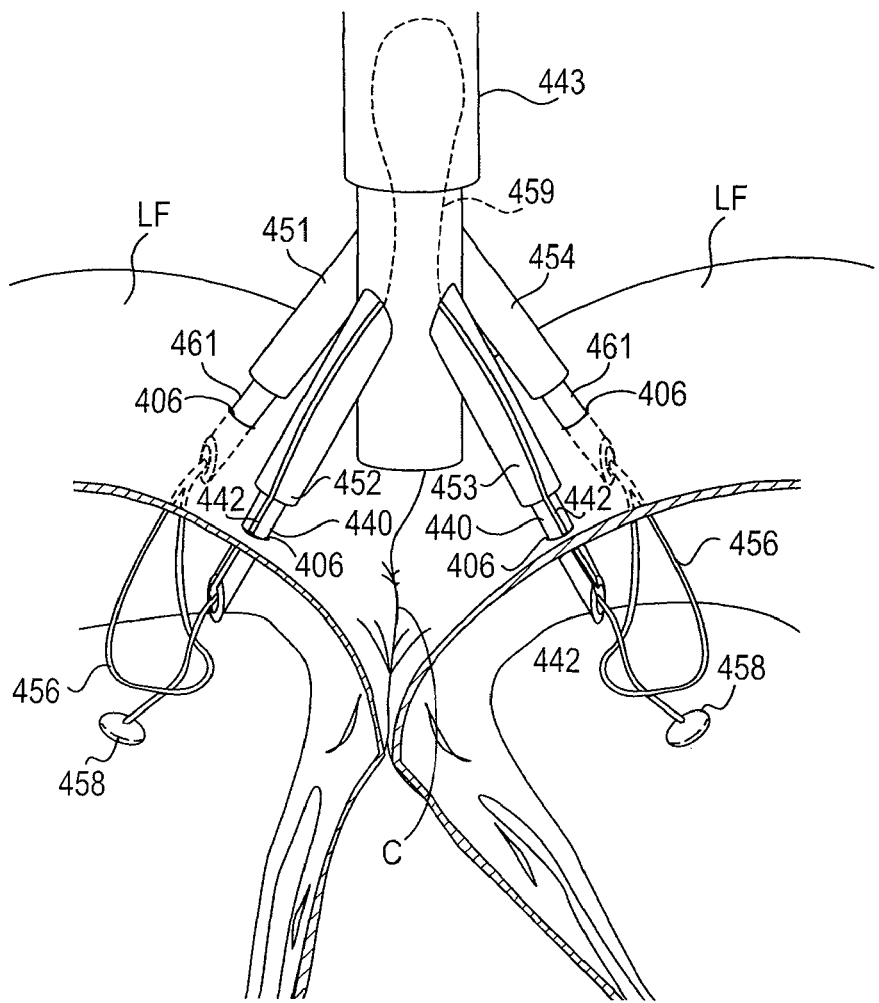
FIG. 34 illustrates an embodiment of the interventional tool having more than one guide conduit including at least two slotted needles for use in deploying a suture line.
Figure 35:
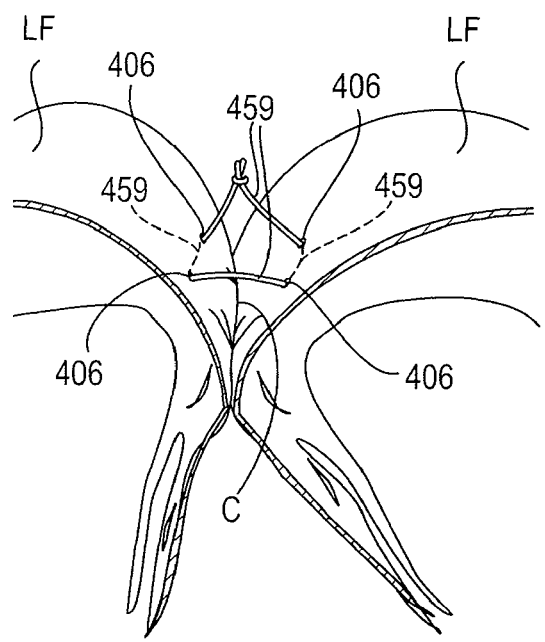
FIG. 35 illustrates a continuous suture line placed according to the methods illustrated in FIG. 34.

FIG. 34 illustrates a similar embodiment of an interventional tool 100 having more than one guide conduit present and directed at each leaflet for leaflet fixation. This embodiment is used to place suture through target points in a method similar to that described above in relation to FIGS. 31-33. However, this embodiment includes at least two slotted needles 440 or similar devices having slots 442 or openings which continue longitudinally from the needle 440 tip toward the shaft 443 for a desired distance. As shown, the tool 100 comprises a first, second, third and fourth guide conduit 451, 452, 453, 454 respectively. Through the first and fourth guide conduits 451, 454 needles 461 or other devices are introduced to penetrate the adjacent leaflets LF and deploy snares 456 on the ventricular side of the leaflets LF. Through the second and third guide conduit 452, 453 slotted needles 440 or other device are introduced to penetrate the leaflets LF and deploy anchors 458 through the snares 456 on the ventricular side of the leaflets LF. Attached to the anchors 458 is a continuous line of suture 459 which runs between the anchors 458. The suture line 459 passes through the penetrations at the target points 406, continues up through the slotted needles 440, out of the slots 442, into a lumen or compartment within the catheter shaft 443 where it forms a loop. Such a suture line 459 is illustrated in FIG. 34. Thus, a continuous line of suture 459 runs from one anchor 458 to another anchor 458 between adjacent leaflets LF. The anchors 458 are then drawn up through the first and fourth guide conduits 451, 454 by retracting the snares 456. As shown in FIG. 35, this results in a continuous suture line 459 across the line of coaptation C on the atrial surface, between adjacent target points 406 on the ventricular side surface of each leaflet LF and again across the line of coaptation C on the atrial surface where the free ends are fixed together by conventional knot tying or any suitable method, including positioning fasteners. It may be appreciated that the above described method and device may be adapted to fix the leaflets together using target points 406 in a variety of locations.

Figure 36:
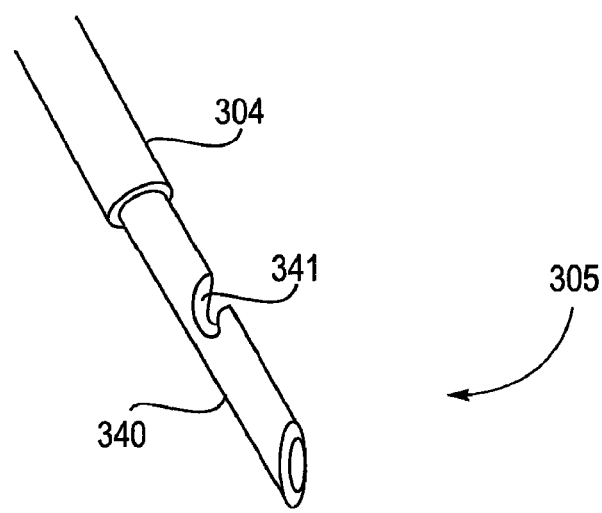
FIG. 36 illustrates an embodiment of the interventional tool having a guide conduit wherein a penetrating device is advanced through the guide conduit having a suture holding feature disposed near its distal end.
Figure 37:
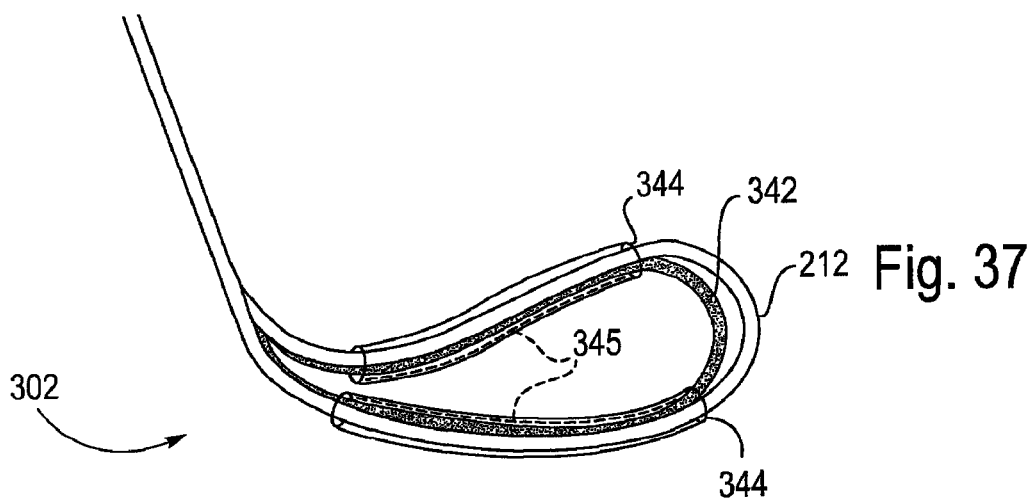
FIG. 37 illustrates a distal element of a capture device comprising a loop having a second loop comprised of suture.
Figure 38:
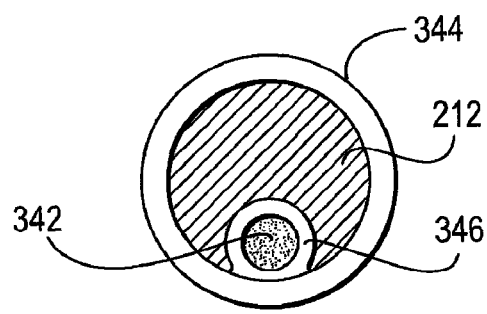
FIG. 38 shows a cross-sectional view of the element shown in FIG. 37.

In another embodiment of the interventional tool 100, each guide conduit 304 comprises a penetrating device or needle 340 having a suture holding feature 341, in this example notch, disposed near its distal end, as shown in FIG. 36. This type of fixation tool 305 is used in combination with a interventional tool 204 having a specific type of distal element 302. This element 302 is similar to the loop 212 previously shown in FIG. 10A. As stated, these loops 212 are preferably made from nitinol or shape-memory wire, however other materials may be suitable. However, in this case, the loops 212 are combined with a second set of loops comprised of suture 342. The suture loops 342 are removably attached to the inside surface of the loops 212. Such attachment may be provided by a number device features. For example, as shown in FIG. 37, the suture loops 342 may be attached and held in place by heat shrink tubing 344 over the loops 212. The heat shrink tubing 344 has perforations 345 along the inside surface of the loop 212 to assist in release of the suture loop 342 when desired. Alternatively, the suture loop 342 may be held in place with a thin layer of material, such as polyurethane, which is applied by dipping or spraying. The suture loop 342 may also be attached by a combination of heat shrink tubing 344 and liquid polyurethane droplets in isolated sections. Further, as shown in cross-section in FIG. 38, the loops 212 themselves may be extruded with a cavity 346 to house the suture 342. The suture 342 may be held in place by the cavity 346 or by heat shrink tubing 344 and/or a layer of material such as polyurethane.

Figure 39:
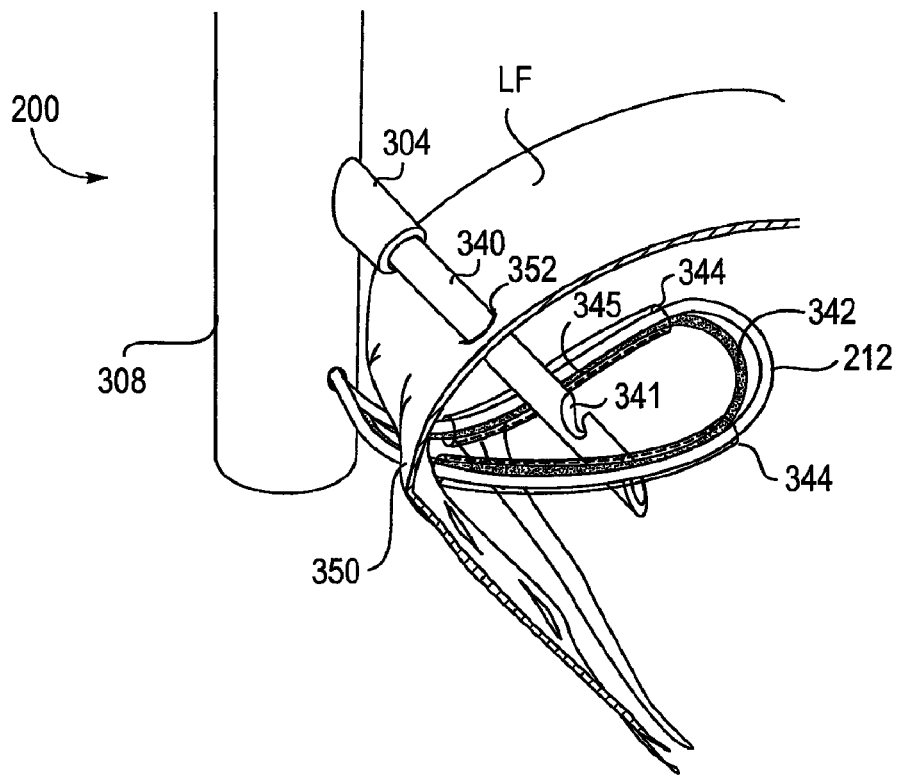
FIGS. 39-41 illustrate methods of using the interventional tool illustrated in FIGS. 36-38.
Figure 40:
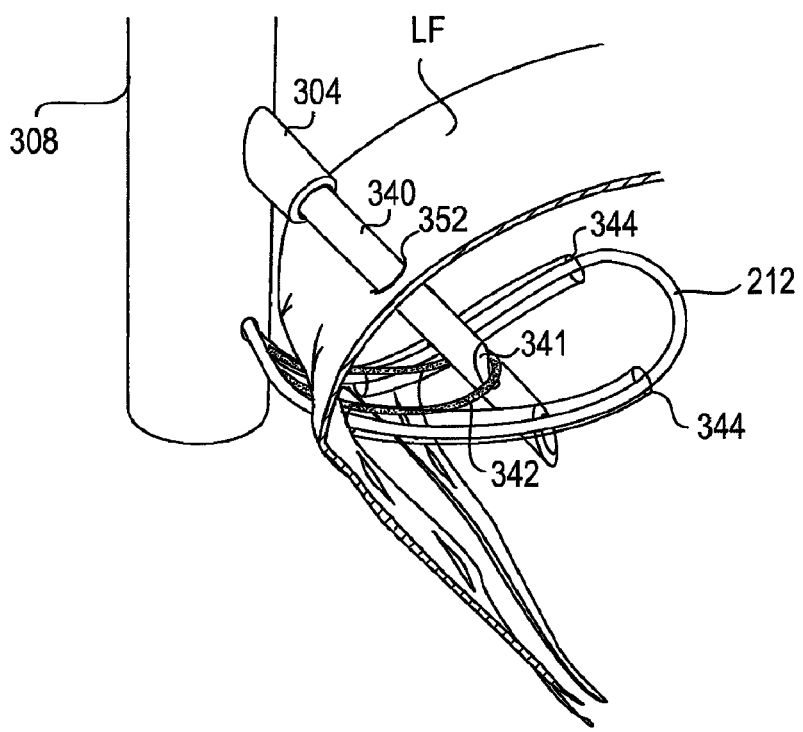
Figure 41:
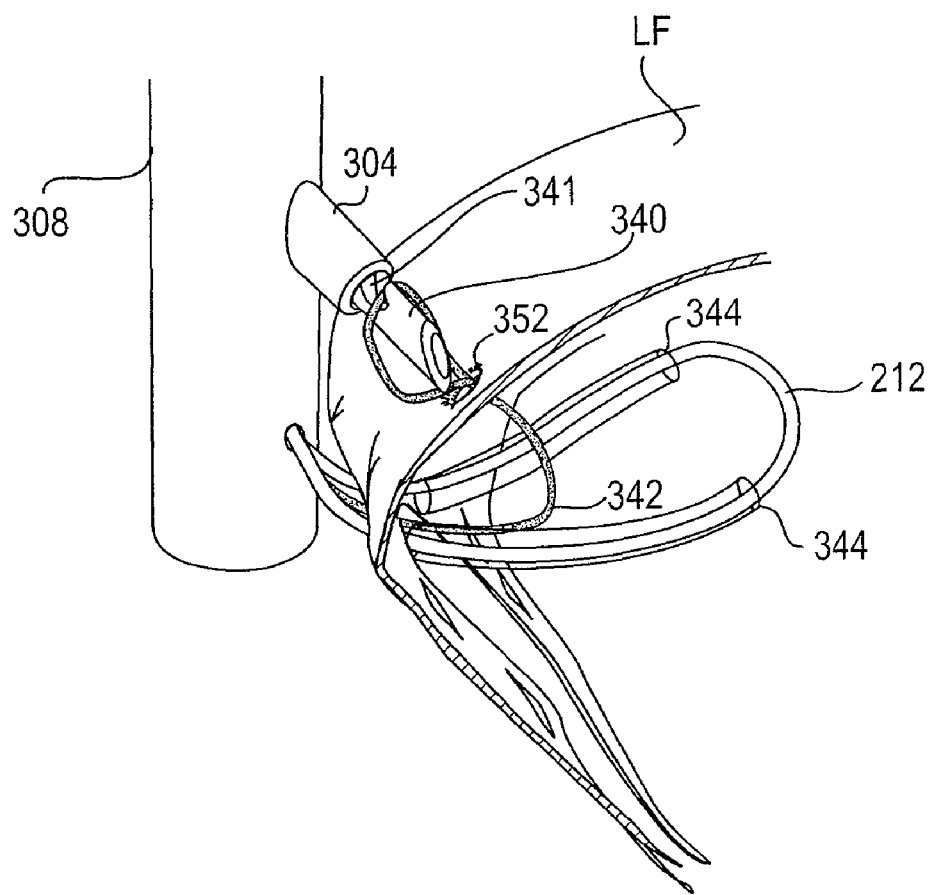

In any case, the interventional catheter 200 has fixation tools 305, comprising a needle 340 having a suture holding feature 341, and distal elements 302, comprising loops 212 combined with suture loops 342, as described above. The guide conduits 304 are located proximal to the distal elements 302 and are capable of extending angularly outward from the shaft 308 to protrude through the loops 212 and suture loops 342. FIG. 39 illustrates an atrial approach to the mitral valve. The interventional catheter 200 is positioned so that the distal element 302 is deployed beyond the valve leaflet LF and one of the loops 212 is pressed against the ventricular surface of the leaflet LF (shading illustrates its planar surface demarked by a leaflet edge 350). It may be appreciated that although the catheter 200 is illustrated to suture one leaflet, the catheter 200 will typically comprise a duplicate arrangement symmetrically positioned on the opposite side of the shaft 308 to additionally suture the other leaflet. Only one leaflet LF is shown for clarity. The needle 340 is advanced toward the leaflet LF either by extension of the guide conduit 304 or the needle 340 itself. In either case, the needle 340 is then advanced to penetrate the leaflet LF and emerge from the other side or the distal side of the leaflet. The penetration hole 352 illustrates the point of entry through the leaflet LF. The needle 340 is further advanced so that the suture holding feature 341 is disposed in the same plane as the suture loop 342. As shown in FIG. 40, the suture loop 342 is then retracted so that it is released from the heat shrink tubing 344 and is disposed within the suture holding feature 341. The needle 340 is then retracted, as shown in FIG. 41, pulling the suture loop 342 through the penetration hole 352 to the atrial side of the valve. To aid in maintaining the suture loop 342 within the suture holding feature 341, a sheath or tubing may be slid over the suture holding feature 341 to hold the suture loop 342 in place. The other leaflet LF of the mitral valve is pierced in the same manner wherein the suture loop is threaded to the atrial side of the valve. The suture loops are then fixed together by conventional knot tying or any suitable method, including positioning suture fasteners.

V. DEVICE EMBODIMENTS. The following device embodiments depict complete device designs utilizing a variety of the specific features described above. In addition, new features are also introduced which provide additional device capabilities. The embodiments shown are designed for treatment of the mitral valve with an atrial approach. However, it may be appreciated that the design features may be adapted for other valves and other approaches.

The embodiments of the interventional catheter 500 will be described in conjunction with its method of use for repairing a regurgitive mitral valve. However, the device will be illustrated independently of the valve anatomy to more clearly illustrate the workings of the device. The relationship of the device to the valve anatomy throughout the steps of the method may be easily visualized based on description.

Figure 42:
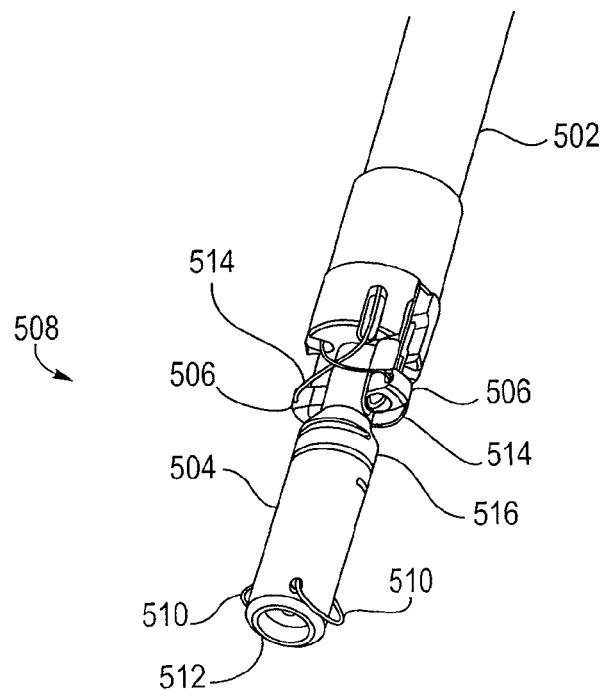
FIGS. 42-51 illustrate a first device embodiment and methods of use according to the aspects of the present invention.

In the first embodiment, referring to FIG. 42, the interventional catheter 500 comprises an elongate shaft 502 having at least one capture device 504 and guide conduit 506 disposed near its distal end 508. The capture device 504 comprises distal loops 510 which are located near the tip 512 of the catheter. Two distal loops 510 are shown, one on each side of the catheter 500, for the capturing of two valve leaflets. The distal loops 510 are retracted for introduction of the catheter 500 through a previously placed guidecatheter. Proximal loops 514 and guide conduits 506 are also shown. Since both the proximal loops 514 and the guide conduits 506 are located proximal to the distal loops and approach the atrial surface of the leaflets, they may be interconnected at the guide conduit cuff 516 as shown. In addition, such interconnectivity may provide advantages which have been presented earlier in relation to embodiments having similar interconnectivity. It may be appreciated, however, that these features may be independent in other embodiments. Similar to the distal loops 510, the proximal loops 514 and guide conduits 506 are retracted for introduction of the catheter 500 through the previously placed guidecatheter. In addition, portions of the catheter 500 may have an integral spring or flexible section 516 which may assist in passing the device through any curves in the guide-catheter during introduction.

Figure 43:
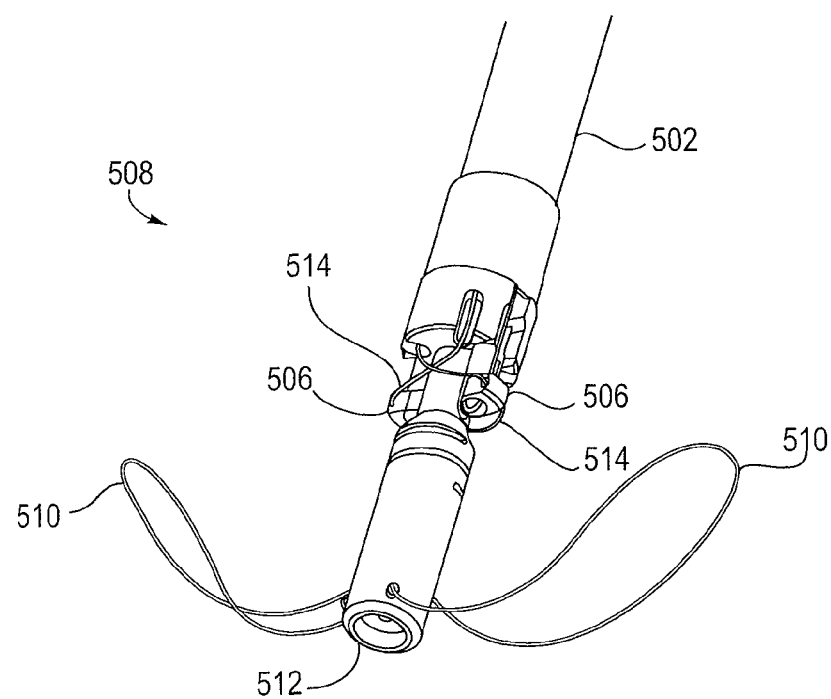

After introduction, the catheter 500 is advanced so that the tip 512 of the catheter is positioned within the atrium, above the mitral valve. Referring to FIG. 43, the distal loops 510 are then deployed so that they protrude radially outward from the shaft 502. The device is then oriented so that the distal loops 510 are positioned substantially perpendicular to the line of coaptation between the two valve leaflets. This may be accomplished with the use of short-axis echocardiography. The tip 512 may be moved roughly along the line of coaptation to the location of regurgitation. After alignment, the tip 512 and distal loops 510 are advanced through the valve, between the leaflets, so that the loops 510 emerge beyond the valve. Perpendicular alignment is then reconfirmed using echocardiography. At this point, the distal end 508 is retracted so that the distal loops 510 move upward, toward the atrium, and press against the ventricular surface of the leaflets. This grasps the leaflets and holds the leaflets in place throughout the cardiac cycle. During diastole, a double orifice geometry may be visualized using short-axis echocardiography, as previously shown in FIG. 5.

Figure 44:
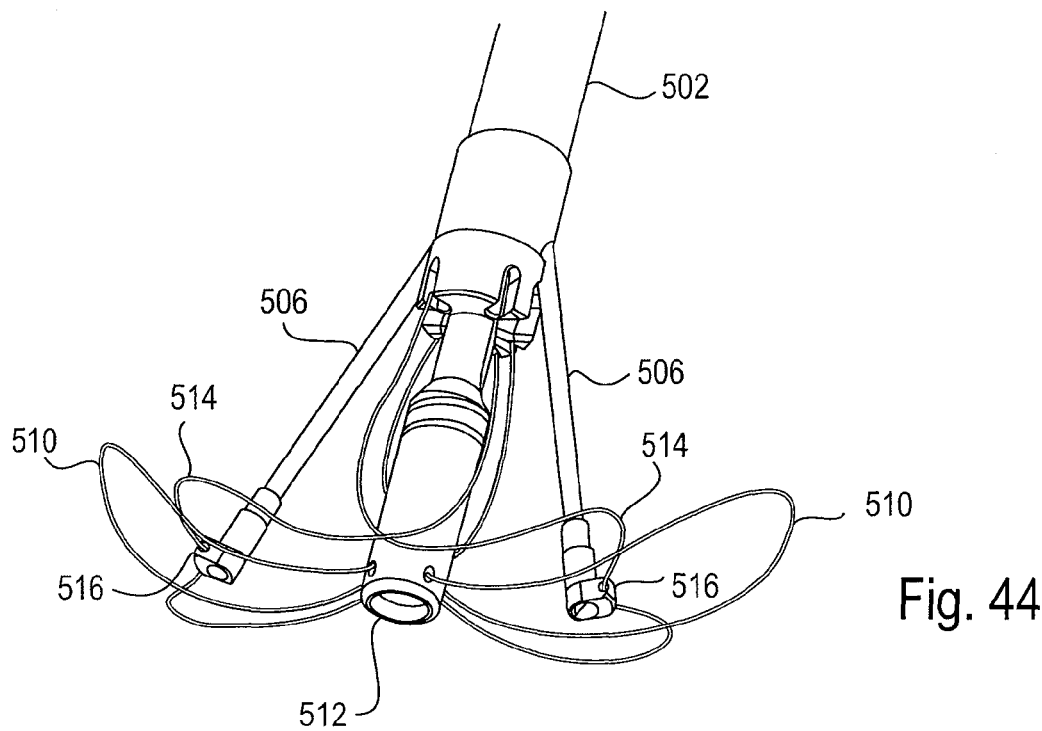

Referring to FIG. 44, the proximal loops 514 and guide conduits 506 are co-deployed and advanced toward the atrial surface of the leaflets. As previously described, interconnection of the proximal loops 514 with the guide conduits 506 may allow one to deploy the other. For example, deployment and advancement of the guide conduits 506 angularly outward may draw the proximal loops 514 out from the shaft 502 effecting their deployment. Alternatively, the proximal loops 514 may be comprised of a material that is of sufficient rigidity so that deployment of the proximal loops 514 draws the guide conduits 506 downward and outward from the shaft 502 effecting their deployment. The proximal loops 514 may also serve to position the guide conduit cuffs 516 within the distal loop 510 as shown.

Figure 45:
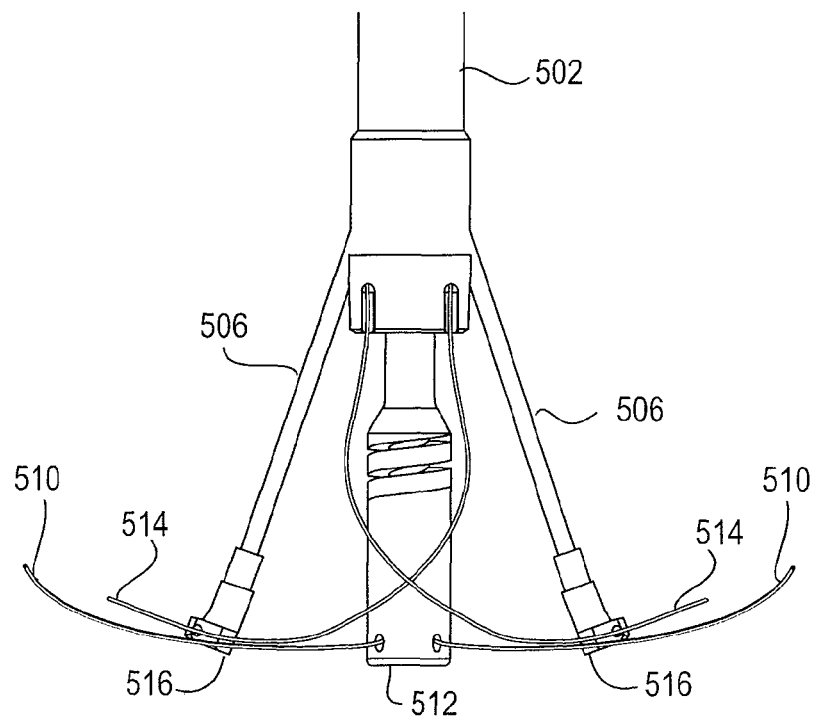

In any case, as shown in FIG. 45 in a side-view, the proximal loops 514 and guide conduits 506 are deployed to near or below the plane of the distal loops 510 so that they are in contact with the atrial surface of the leaflets. Although not illustrated, the valve leaflets would reside between the proximal loops 514 and the distal loops 510. In some cases, such as in severe prolapsing valves, the proximal loops 514 may be deployed prior to grasping the leaflets with the distal loops 510. In these cases, the proximal loops 514 may act to limit the extent of prolapse and to assist in trapping the leaflet between the proximal and distal loops.

Figure 46:
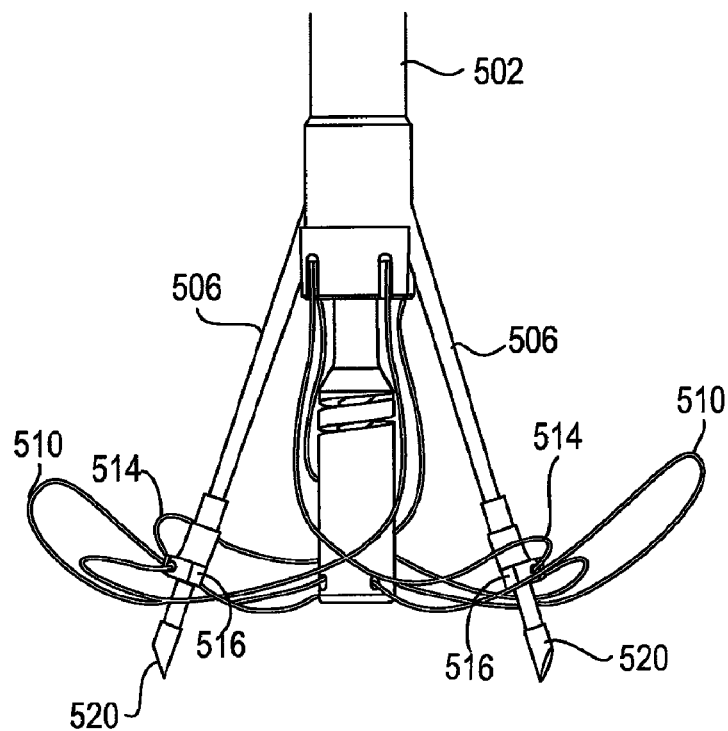
Figure 47:
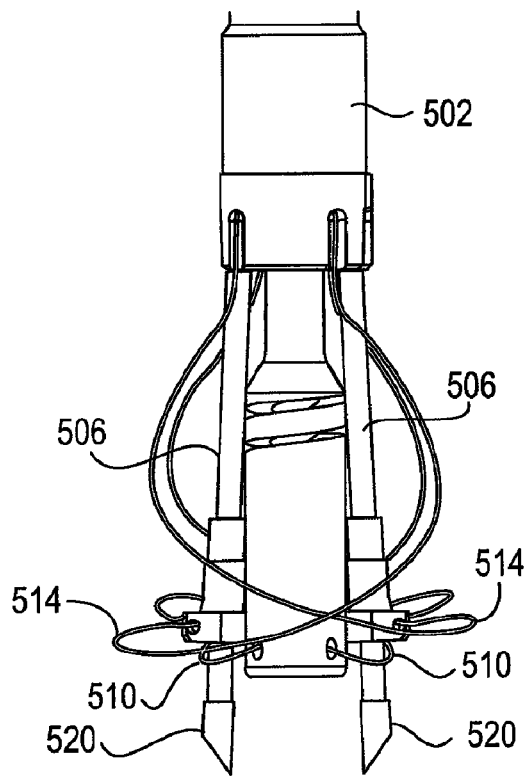

Once the leaflets are securely grasped between the proximal and distal loops, the double orifice geometry is confirmed during diastole using short-axis echocardiography. If the positioning of the leaflets appears as desired, piercing devices or needles 520 are advanced from the guide conduit cuffs 516 to puncture and penetrate the valve leaflets. As shown in FIG. 46, the needles 520 are advanced through the distal loops 510 so that the distal loops 510 may support the leaflet during penetration. As shown in FIG. 47, the distal loops 510 are then retracted, pulling the needles 520 radially toward the shaft 502. Since each needle 520 is pierced through a leaflet, the radially inward movement of the needles 520 draws the leaflets together at the points of penetration. This simulates the methods of performing a standard surgical bow-tie repair. At this point, the proximal loops 514 may be removed from the valve surface and the mitral regurgitation may be evaluated to determine if the two pierced points are suitable for fixing the leaflets together. Color Doppler echo will show if the regurgitation of the valve has been reduced. If the resulting mitral flow pattern is satisfactory, the leaflets may be fixed together in this orientation. If the pattern is unsatisfactory, the above steps may be repeated until a satisfactory flow pattern is obtained.

Figure 48:
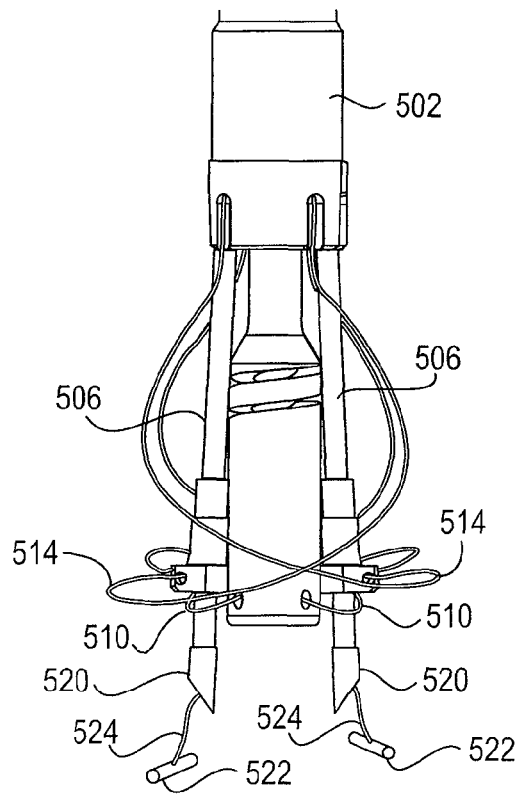
Figure 49:
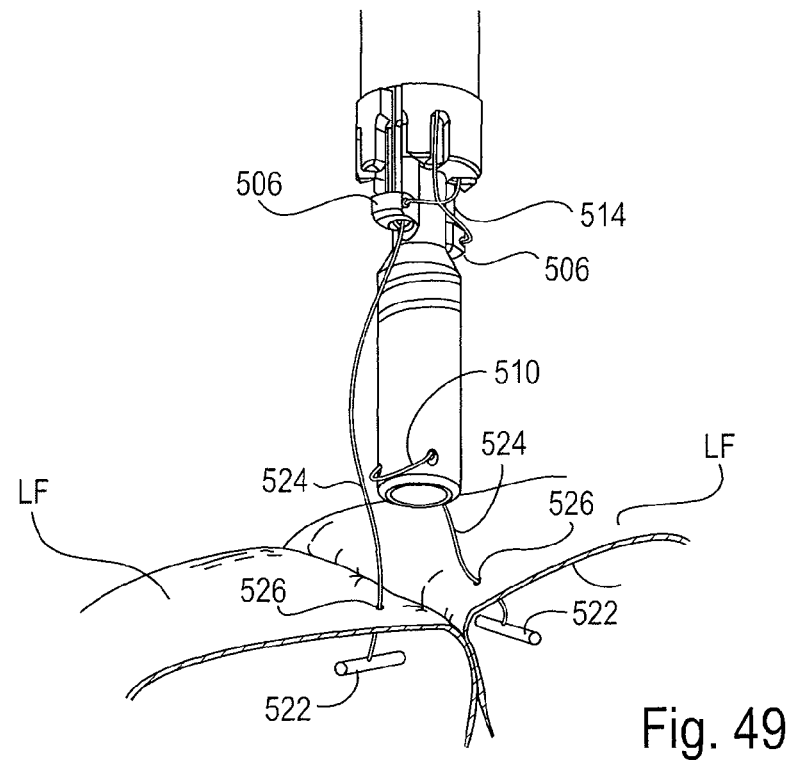

Referring to FIG. 48, fixation may be achieved with the use of fixation pledgets or anchors 522 which are deployable from the needles 520. Push rods (not shown) may be advanced within the needles 520 to deploy the anchors 522 from the needles 520. Attached to each anchor 522 is a line of suture 524 which is captured within each needle 520, as shown. The needles 520 are then retracted back through the leaflet penetrations, leaving the anchors 522 on the ventricular side of the valve leaflets while threading the suture 524 through the penetrations. Simultaneously or subsequently, the tip 512 and/or distal end 508 is advanced distally to position the distal loops 510 slightly below the anchors 522. In this way, the distal loops 510 may be retracted inwardly without trapping the lines of suture 524 in the loops 510. The distal loops 510 are thus retracted to a low profile position and the proximal loops 514 and guide conduits 506 are also retracted to their original low profile position. As shown in FIG. 49, the distal end 508 is then withdrawn from the valve, leaving the anchors 522 disposed on the ventricular side of the leaflets LF and the lines of suture 524 threaded through the penetrations 526, continuing up through the guide conduits 506.

Figure 50:
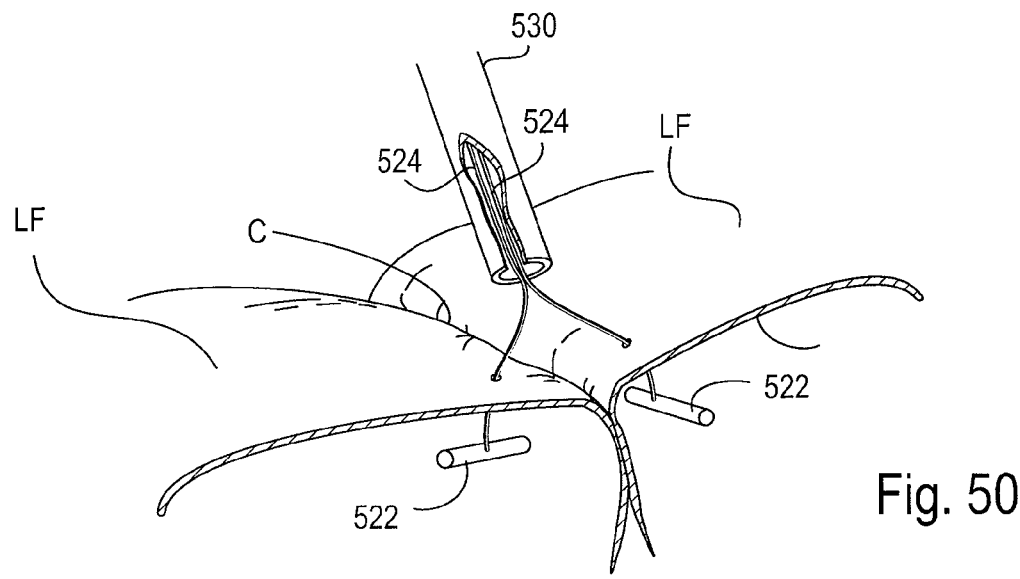
Figure 51:
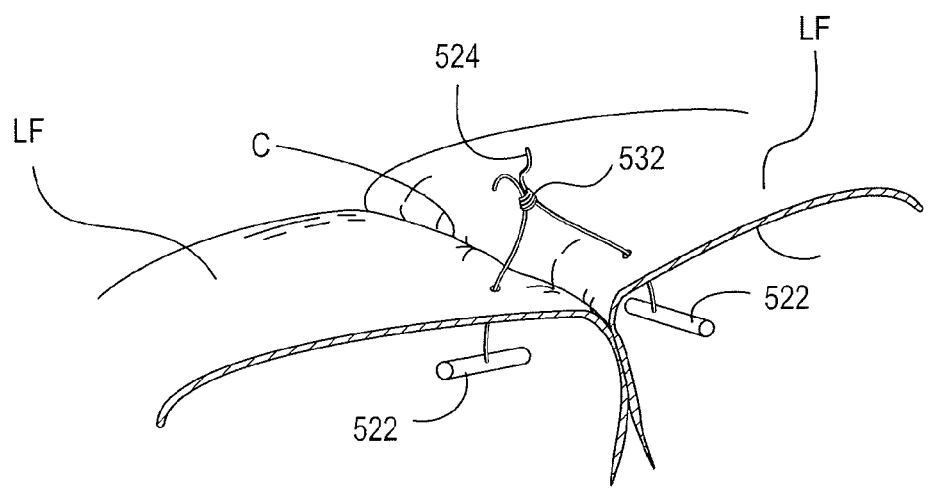

Referring to FIG. 50, a holding tube 530 containing the free ends of both sutures 524 is separated from the shaft 502 and advanced toward the atrial surface of the leaflets LF. This holds tension on the anchors 522 to maintain the position of the anchors 522 against the ventricular surface of the leaflets LF and to maintain the coaptation of the leaflets LF along the line of coaptation C. A suture fixation device deployment catheter (not shown) is then inserted through, over or replacing the holding tube 530 to tie the sutures together with a knot or to deploy a fixation device 532 to hold the sutures 524 in place, as shown in FIG. 51. A suture cutter (not shown) is integral with the deployment catheter and is used to cut the suture lines 524 proximal to the fixation device 532. The deployment catheter is then removed leaving the fixed leaflets in a repaired condition.

Figure 52:
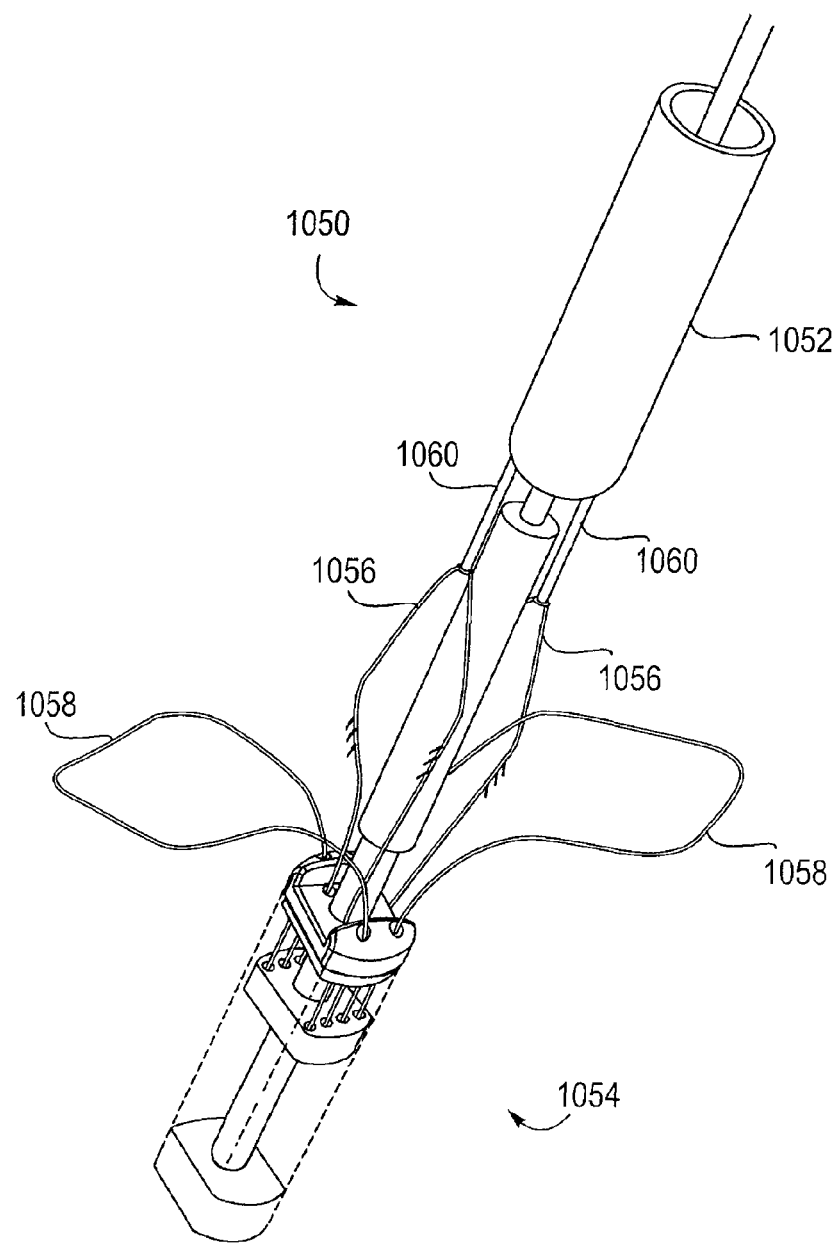
FIG. 52-58 illustrate a second device embodiment and methods of use according to the aspects of the present invention.

In the second embodiment, referring to FIG. 52, the interventional catheter 1050 comprises an elongate shaft 1052 and a detachable capture device 1054. The capture device 1054 comprises, among others, proximal elements 1056 and distal elements 1058. Such a capture device 1054 is similar to that presented in FIGS. 17C-17D. Again, the proximal elements 1056 may be separately deployable from the distal elements 1058. As shown, the distal elements 1058 are deployed so that they are extended radially outward from the shaft 1052. The proximal elements 1056 may be held against the shaft by sutures 1060 which are drawn up within the shaft 1052. In this orientation, the catheter 1050 may be manipulated between the leaflets so that the distal elements 1058 are positioned against the ventricular surface of the valve leaflets LF.

Figure 53:
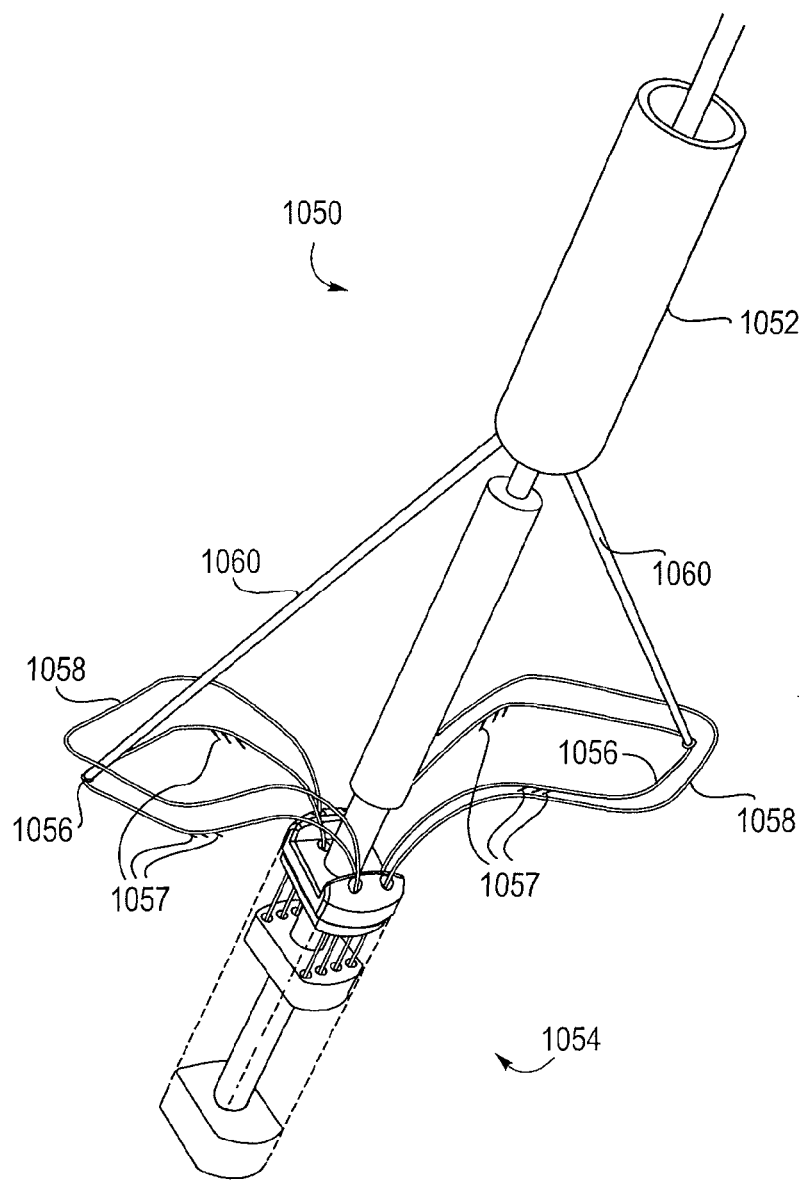

Referring to FIG. 53, the proximal elements 1056 may then be released by slacking the sutures 1060. This allows the preformed elements 1056 to extend radially outward and downward, as illustrated. Depending on the curvature of the proximal elements 1056, they may remain proximal to, move to within the same plane of, or move beyond the plane of the distal elements 1058. Here, the proximal elements 1056 are shown slightly beyond the plane of the distal elements 1058.

Thus, the leaflets LF would be grasped and held in place between the elements 1056, 1058. In addition, the proximal elements 1056 include prongs 1057 to provide friction and assist in holding the leaflets LF.

Figure 54:
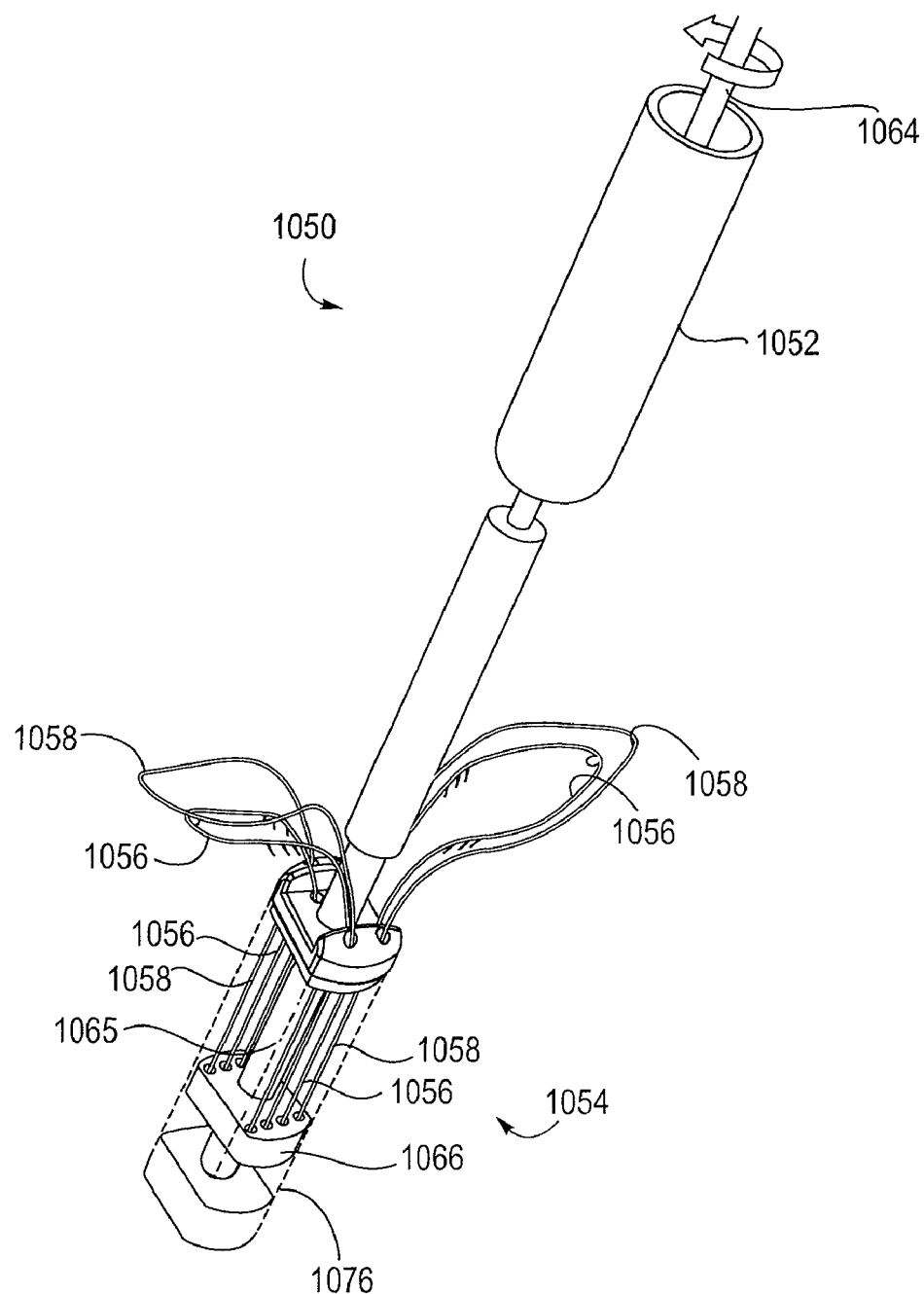

The leaflets LF may then be repositioned by manipulating the elements 1056, 1058 while the leaflets LF are grasped therebetween. Referring to FIG. 54, the elements 1056, 1058 may be drawn inward by rotation of a torque shaft 1064, such rotation indicated by an arrow. Rotation of the torque shaft 1064 drives a screw 1065 in the capture device 1054 which translates a nut 1066 downward within the capture device 1054. The translating nut 1066 draws the elements 1056, 1058 inward to assist in coaptation of the leaflets LF.

Figure 55:
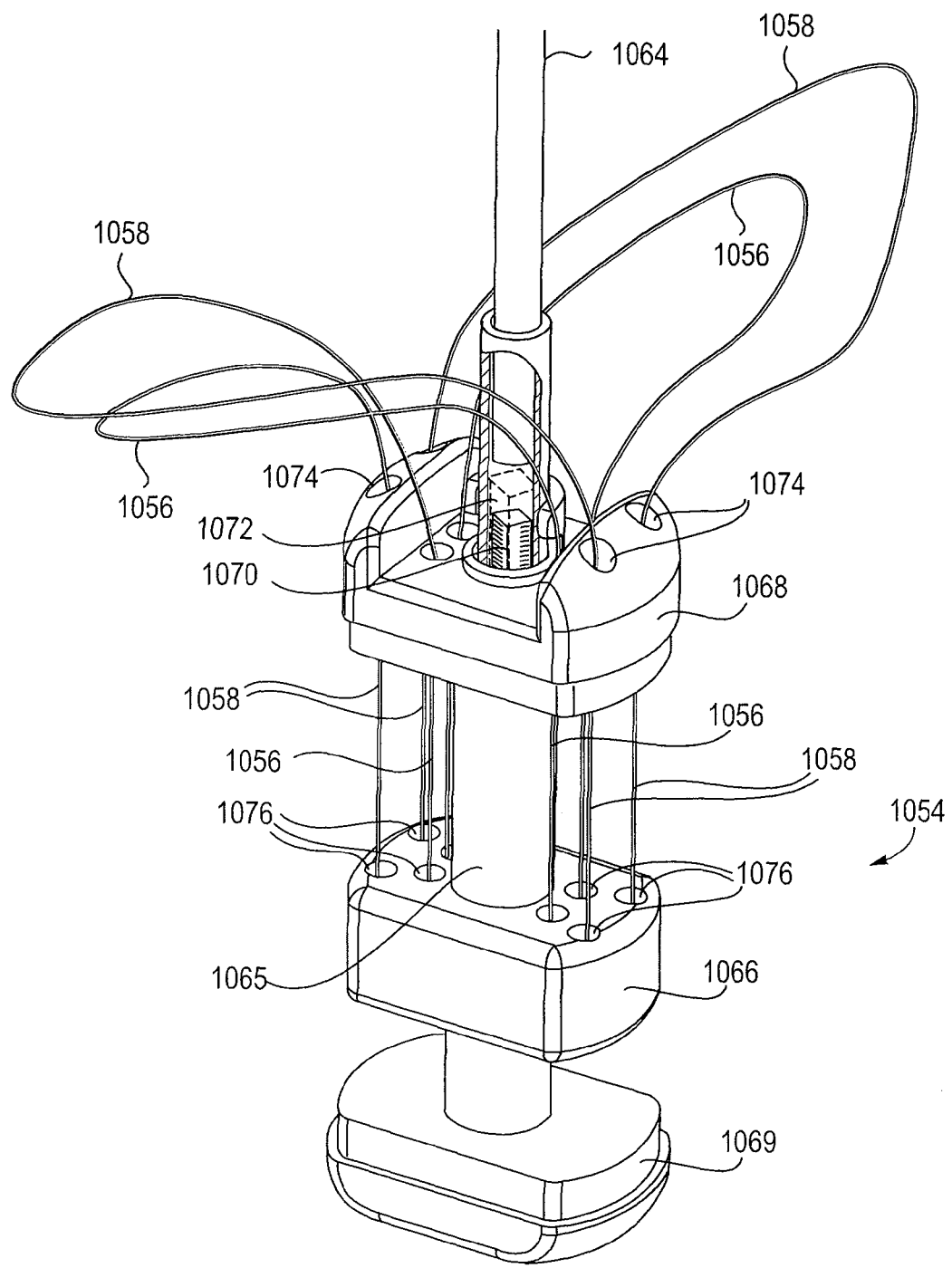

FIG. 55 more closely illustrates the workings of the capture device 1054. The nut 1066 is positioned on the screw 1065 between a top structure 1068 and a bottom structure 1069. The proximal and distal elements 1056, 1058 are fixedly attached in holes 1076 in the nut 1066 and pass through holes 1074 in the top structure 1068. The screw 1065 has a screw top 1070 which extends into a torque driver 1072. The inner diameter of the driver 1072 is square to receive the square screw top 1070. The torque shaft 1064 is attached to the driver 1072 so that rotation of the shaft 1064 rotates the screw 1065. This in turn translates the nut 1066 downward, drawing the elements 1056, 1058 inward through the holes 1074. Since the nut 1066 has flat sides, the nut 1066 will not rotate within an outer casing 1076 (shown in FIG. 54) which fits against the nut 1066.

Figure 56:
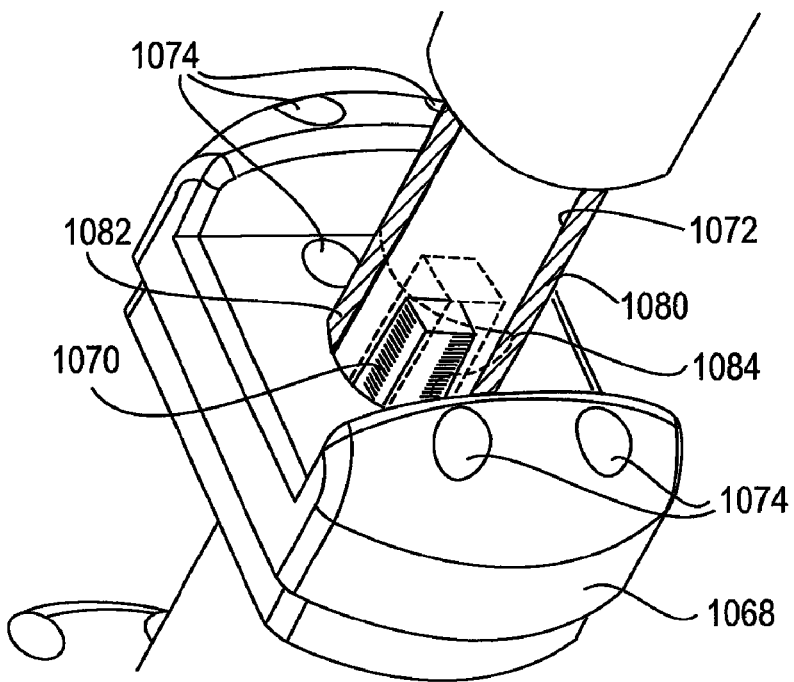
Figure 57:
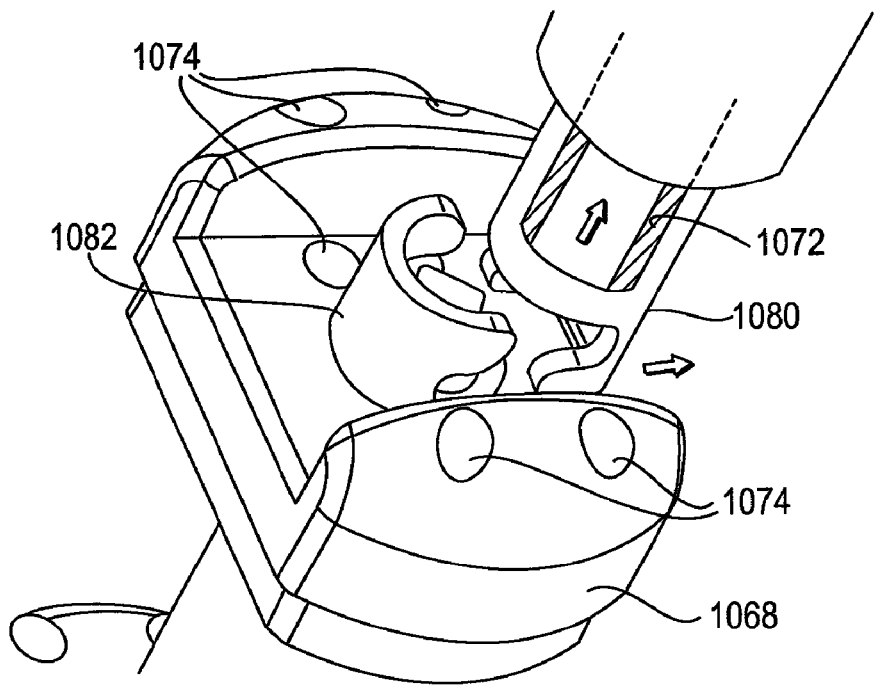
Figure 58:
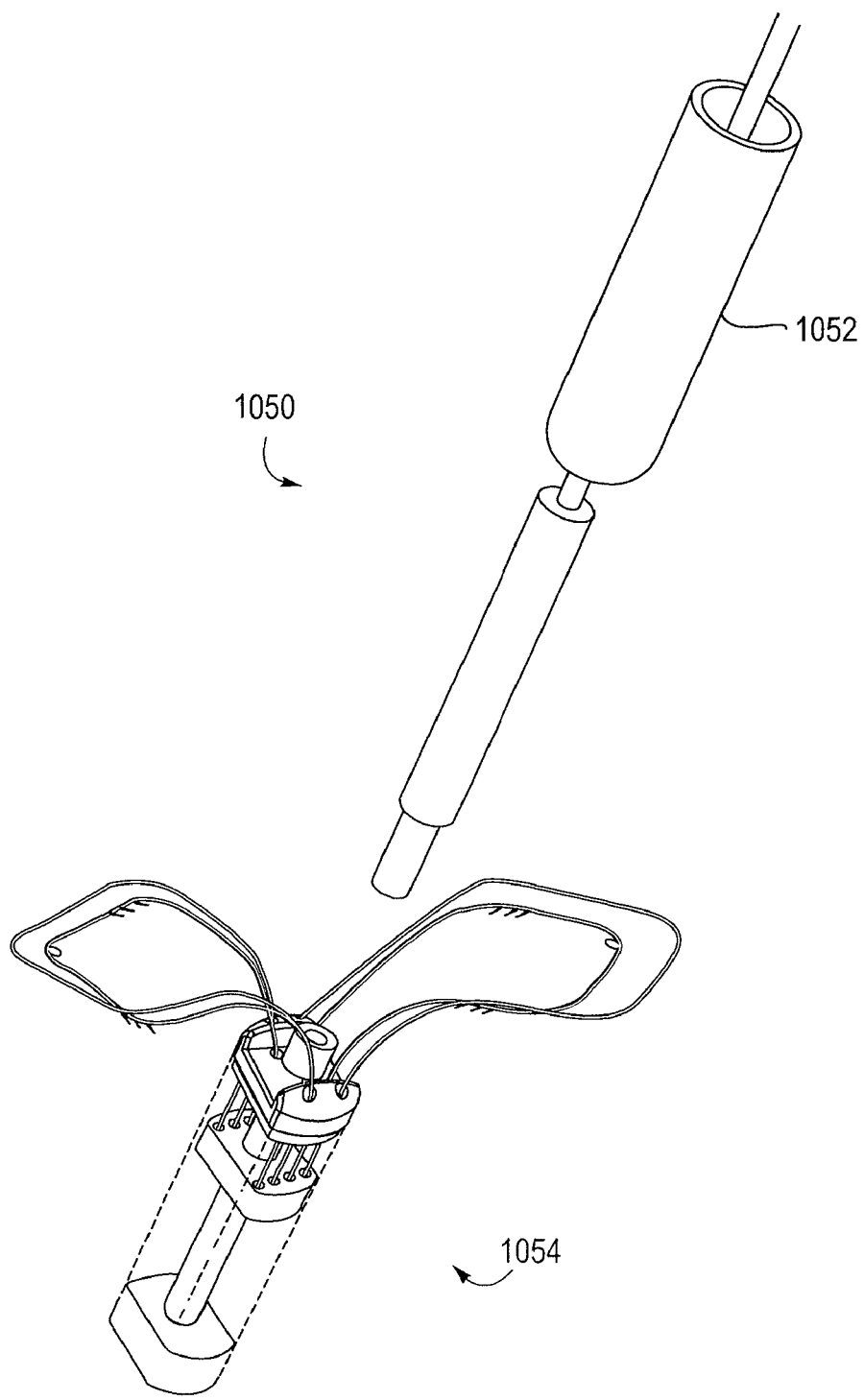

During repositioning of the leaflets LF, imaging is used to verify that coaptation and mitral regurgitation reduction is suitable. Once the leaflets LF are suitably positioned, the capture device 1054 is ready for detachment. FIGS. 56-57 illustrate an embodiment of the detachment mechanism which is similar in design and function to that previously described in relation to FIGS. 21D-21E. FIG. 56 illustrates a tubular upper shaft 1080 and a detachable lower shaft 1082 which are interlocked at a joining line 1084. Again, the joining line 1084 may have any shape or curvature which will allow or facilitate interlocking and later detachment. The torque driver 1072 bridges the joining line 1084 as shown. Such placement of the driver 1072 prevents twisting and translation of the upper and lower shafts 1080, 1082. FIG. 57 illustrates detachment of the lower shaft 1082 from the upper shaft 1080. This is achieved by retracting the driver 1072 to a position above the joining line 1084 which in turn allows the shafts 1080, 1082 to separate. Consequently, the capture device 1054 is detached from the shaft 1052 of the interventional catheter 1050, as shown in FIG. 58, and left behind as an implant to hold the leaflets LF in the desired coapted position.

Figure 59:
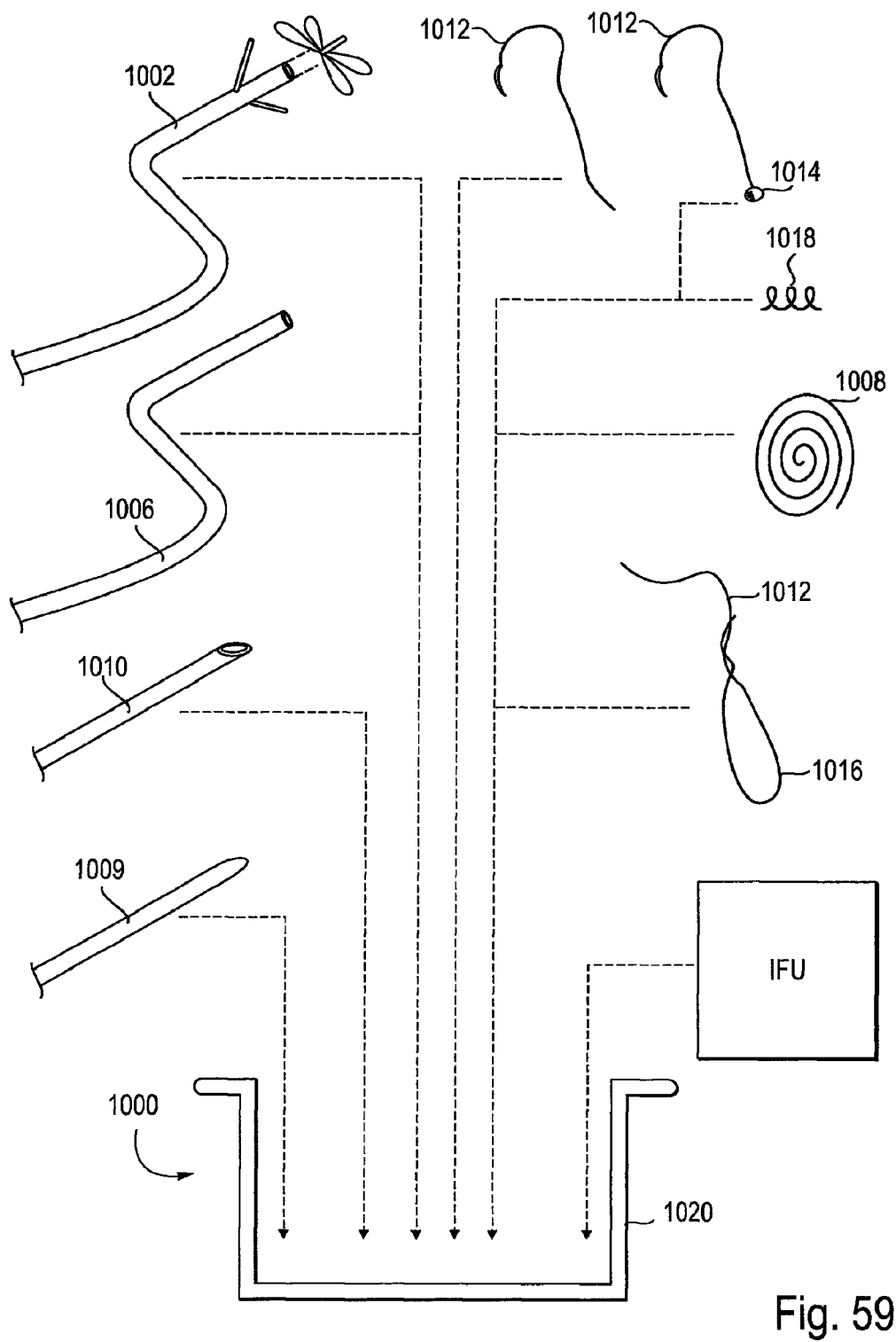
FIG. 59 illustrates a kit constructed in accordance with the principles of the present invention.

Kits 1000 according to the present invention comprise any number of items related to the devices, systems and methods described above. As shown in FIG. 59, such kits 1000 typically include at least one interventional catheter 1002 having a capture device 1004. Optionally, the capture device 1004 may be detachable and, in such a case, a number of capture devices 1004 (or fixation devices) may be included in the kit 1000. The kits 1000 also include instructions for use IFU setting forth any of the methods according to the present invention. Optionally, the kits 900 may further include any of the other system components described above, such as one or more guidecatheters 1006, guide wires 1008, dilators 1009, penetration devices 1010, sutures 1012, anchors 1014 optionally having sutures 1012 attached, snares 1016 optionally having sutures 1012 attached, and fasteners 1018 to fix sutures together, to name a few. Some or all kit components will usually be packaged together in a pouch 1020 or other conventional medical device packaging. Usually, those kit components which will be used in performing the procedure on the patient will be sterilized and maintained within the kit. Optionally, separate pouches, bags, trays or other packaging may be provided within a larger package, where the smaller packs may be opened separately to separately maintain the components in a sterile fashion.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A device for repairing a cardiac valve, said device comprising:
   an interventional catheter adapted to pass from the remote vasculature of a patient to a position within a heart of the patient adjacent to the cardiac valve; and
   a capture device on the interventional catheter comprising at least one distal element coupled to the catheter, wherein the distal element is protrudable radially outward and is adapted to press against a downstream surface of at least one leaflet,
   wherein the interventional catheter further comprises at least one fixation tool for fixing the valve leaflet to a second valve leaflet,
   the fixation tool comprising a penetrating device which has a suture and an anchor coupled with the suture,
   wherein the anchor has a first profile adapted to be housed at least partially within the penetrating device and a second profile larger than the first profile, the second profile adapted to engage the downstream surface of the at least one leaflet thereby anchoring the suture to the at least one leaflet,
   wherein the anchor comprises a tubular structure adapted to radially expand upon delivery of the anchor through the valve leaflet, and
   wherein the tubular structure expands radially outward when axially compressed.

2. The device as in claim 1, wherein the penetrating device is adapted to penetrate an atrial surface of the valve leaflet and pass therethrough so as to emerge on a ventricular surface of the valve leaflet.

3. The device of claim 1, wherein the second profile expands from the first profile which is in a compressed state.

4. The device of claim 1, wherein the anchor comprises one of a stainless steel, nitinol or a shape memory material.

5. The device of claim 1, wherein the anchor self-expands from the first profile to the second profile.

6. A device for repairing a cardiac valve, said device comprising:
   an interventional catheter adapted to pass from the remote vasculature of a patient to a position within a heart of the patient adjacent to the cardiac valve; and
   a capture device on the interventional catheter comprising at least one distal element coupled to the catheter, wherein the distal element is protrudable radially outward and is adapted to press against a downstream surface of at least one leaflet,
   wherein the interventional catheter further comprises at least one fixation tool for fixing the valve leaflet to a second valve leaflet,
   the fixation tool comprising a penetrating device which has a suture and an anchor coupled with the suture, and
   wherein the anchor has a first profile adapted to be housed at least partially within the penetrating device and a second profile larger than the first profile, the second profile adapted to engage the downstream surface of the at least one leaflet thereby anchoring the suture to the at least one leaflet,
   wherein the anchor comprises two parts, the two parts positionable on opposite sides of the valve leaflet thereby capturing the valve leaflet therebetween,
   wherein the first part comprises one or more spikes and the second part comprises one or more receptacles, the spikes being adapted to penetrate the valve leaflet and interlock the receptacles.

7. A device for repairing a cardiac valve, said device comprising:
   an interventional catheter adapted to pass from the remote vasculature of a patient to a position within a heart of the patient adjacent to the cardiac valve; and
   a capture device on the interventional catheter comprising at least one distal element coupled to the catheter, wherein the distal element is protrudable radially outward and is adapted to press against a downstream surface of at least one leaflet,
   wherein the interventional catheter further comprises at least one fixation tool for fixing the valve leaflet to a second valve leaflet,
   the fixation tool comprising a penetrating device which has a suture and an anchor coupled with the suture, and
   wherein the anchor has a first profile adapted to be housed at least partially within the penetrating device and a second profile larger than the first profile, the second profile adapted to engage the downstream surface of the at least one leaflet thereby anchoring the suture to the at least one leaflet,
   wherein the anchor comprises a tubular structure adapted to radially expand upon delivery of the anchor through the valve leaflet, and
   wherein the tubular structure comprises a plurality of longitudinal slits.

8. The device of claim 1, wherein the anchor comprises two or more beams, the beams adapted to expand radially outward.

9. A device for repairing a cardiac valve, said device comprising:
   an interventional catheter adapted to pass from the remote vasculature of a patient to a position within a heart of the patient adjacent to the cardiac valve; and
   a capture device on the interventional catheter comprising at least one distal element coupled to the catheter, wherein the distal element is protrudable radially outward and is adapted to press against a downstream surface of at least one leaflet,
   wherein the interventional catheter further comprises at least one fixation tool for fixing the valve leaflet to a second valve leaflet,
   the fixation tool comprising a penetrating device which has a suture and an anchor coupled with the suture,
   wherein the anchor has a first profile adapted to be housed at least partially within the penetrating device and a second profile larger than the first profile, the second profile adapted to engage the downstream surface of the at least one leaflet thereby anchoring the suture to the at least one leaflet, and
   wherein the anchor comprises a tubular structure having a plurality of axial arms adapted to be bent outwardly.

* * * * *